United States Patent
Fleury et al.

(10) Patent No.: US 9,585,882 B2
(45) Date of Patent: *Mar. 7, 2017

(54) NEPRILYSIN INHIBITORS

(71) Applicants: Melissa Fleury, San Francisco, CA (US); Anne-Marie Beausoliel, San Mateo, CA (US); Adam D. Hughes, Belmont, CA (US); Daniel D. Long, San Francisco, CA (US); Donna A. A. Wilton, San Francisco, CA (US)

(72) Inventors: Melissa Fleury, San Francisco, CA (US); Anne-Marie Beausoliel, San Mateo, CA (US); Adam D. Hughes, Belmont, CA (US); Daniel D. Long, San Francisco, CA (US); Donna A. A. Wilton, San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/608,405

(22) Filed: Jan. 29, 2015

(65) Prior Publication Data
US 2015/0209352 A1    Jul. 30, 2015

Related U.S. Application Data

(60) Provisional application No. 61/933,402, filed on Jan. 30, 2014.

(51) Int. Cl.
| | |
|---|---|
| A61K 31/505 | (2006.01) |
| A61K 31/4192 | (2006.01) |
| A61K 45/06 | (2006.01) |
| A61K 31/415 | (2006.01) |
| C07C 229/08 | (2006.01) |
| C07C 271/22 | (2006.01) |
| C07D 231/14 | (2006.01) |
| C07D 263/34 | (2006.01) |
| C07D 249/10 | (2006.01) |
| C07D 307/24 | (2006.01) |
| C07D 207/16 | (2006.01) |
| C07D 249/04 | (2006.01) |
| A61K 31/421 | (2006.01) |
| C07D 271/07 | (2006.01) |
| A61K 31/4245 | (2006.01) |

(Continued)

(52) U.S. Cl.
CPC .......... *A61K 31/505* (2013.01); *A61K 31/415* (2013.01); *A61K 31/4192* (2013.01); *A61K 31/4196* (2013.01); *A61K 31/421* (2013.01); *A61K 31/4245* (2013.01); *A61K 31/44* (2013.01); *A61K 45/06* (2013.01); *C07C 229/08* (2013.01); *C07C 271/22* (2013.01); *C07D 207/16* (2013.01); *C07D 213/56* (2013.01); *C07D 213/81* (2013.01); *C07D 231/14* (2013.01); *C07D 239/28* (2013.01); *C07D 239/42* (2013.01); *C07D 249/04* (2013.01); *C07D 249/10* (2013.01); *C07D 249/14* (2013.01); *C07D 261/10* (2013.01); *C07D 263/34* (2013.01); *C07D 271/07* (2013.01); *C07D 307/24* (2013.01); *C07D 403/12* (2013.01); *C07D 405/12* (2013.01)

(58) Field of Classification Search
None
See application file for complete search history.

(56) References Cited

U.S. PATENT DOCUMENTS

| | | |
|---|---|---|
| 4,189,604 A | 2/1980 | Umezawa et al. |
| 4,206,232 A | 6/1980 | Ondetti et al. |

(Continued)

OTHER PUBLICATIONS

Ksander et al., "Dicarboxylic acid dipeptide neutral endopeptidase inhibitors", Journal of Medicinal Chemistry, 38(10): 1689-1700 (1995).
Misawa et al., "Structure-based design of dipeptide derivatives for the human neutral endopeptidase", Bioorganic & Medicinal Chemistry, 19: 5935-5947 (2011).

(Continued)

*Primary Examiner* — Kamal Saeed
(74) *Attorney, Agent, or Firm* — Jeffrey A. Hagenah; Wendy Petka

(57) ABSTRACT

In one aspect, the invention relates to compounds having the formula I:

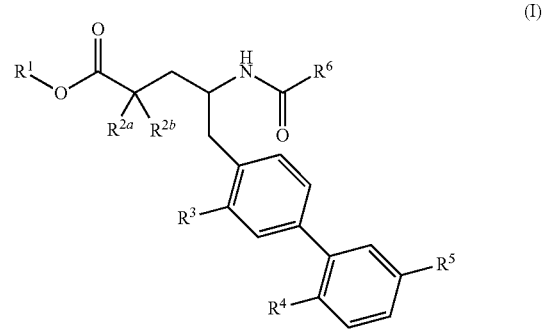

where $R^1$, $R^{2a}$, $R^{2b}$, and $R^3$-$R^6$ are as defined in the specification, or a pharmaceutically acceptable salt thereof. These compounds have neprilysin inhibition activity. In another aspect, the invention relates to pharmaceutical compositions comprising these compounds; methods of using these compounds; and processes and intermediates for preparing these compounds.

24 Claims, No Drawings

(51) Int. Cl.
  *C07D 213/81* (2006.01)
  *A61K 31/44* (2006.01)
  *C07D 239/28* (2006.01)
  *A61K 31/4196* (2006.01)
  *C07D 405/12* (2006.01)
  *C07D 403/12* (2006.01)
  *C07D 239/42* (2006.01)
  *C07D 249/14* (2006.01)
  *C07D 261/10* (2006.01)
  *C07D 213/56* (2006.01)

(56) References Cited

U.S. PATENT DOCUMENTS

| | | | |
|---|---|---|---|
| 4,374,829 A | 2/1983 | Harris et al. |
| 4,513,009 A | 4/1985 | Roques et al. |
| 4,722,810 A | 2/1988 | Delaney et al. |
| 4,906,615 A | 3/1990 | Berger |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Barnish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |
| 5,508,272 A | 4/1996 | Robl |
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 12/2003 | Challenger et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |
| 8,586,536 B2 | 11/2013 | Gendron et al. |
| 8,686,184 B2 | 4/2014 | Fleury et al. |
| 8,691,868 B2 | 4/2014 | Hughes et al. |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0046397 A1 | 2/2011 | Hook et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0289710 A1 | 11/2012 | Hook et al. |
| 2012/0309724 A1 | 12/2012 | Fleury et al. |
| 2013/0323271 A1 | 12/2013 | Mammen et al. |
| 2013/0330365 A1 | 12/2013 | Hughes et al. |
| 2013/0330366 A1 | 12/2013 | Hughes et al. |
| 2014/0045906 A1 | 2/2014 | Fleury et al. |
| 2014/0256702 A1 | 9/2014 | Fenster et al. |
| 2015/0210690 A1* | 7/2015 | Fleury ............... C07D 471/04 514/210.2 |

OTHER PUBLICATIONS

The International Search Report and the Written Opinion for PCT application PCT/US2015/013420 dated Mar. 12, 2015.
U.S. Appl. No. 14/608,686, Fleury et al.

\* cited by examiner

NEPRILYSIN INHIBITORS

CROSS-REFERENCE TO RELATED APPLICATIONS

This application claims the benefit of U.S. Provisional Application No. 61/933,402 filed on Jan. 30, 2014; the entire disclosure of which is incorporated herein by reference.

BACKGROUND OF THE INVENTION

Field of the Invention

The present invention relates to novel compounds having neprilysin-inhibition activity. The invention also relates to pharmaceutical compositions comprising these compounds, processes and intermediates for preparing these compounds and methods of using these compounds to treat diseases such as hypertension, heart failure, pulmonary hypertension, and renal disease.

State of the Art

Neprilysin (neutral endopeptidase, EC 3.4.24.11) (NEP), is an endothelial membrane bound $Zn^{2+}$ metallopeptidase found in many organs and tissues, including the brain, kidneys, lungs, gastrointestinal tract, heart, and the peripheral vasculature. NEP degrades and inactivates a number of endogenous peptides, such as enkephalins, circulating bradykinin, angiotensin peptides, and natriuretic peptides, the latter of which have several effects including, for example, vasodilation and natriuresis/diuresis, as well as inhibition of cardiac hypertrophy and ventricular fibrosis. Thus, NEP plays an important role in blood pressure homeostasis and cardiovascular health.

NEP inhibitors, such as thiorphan, candoxatril, and candoxatrilat, have been studied as potential therapeutics. Compounds that inhibit both NEP and angiotensin-I converting enzyme (ACE) are also known, and include omapatrilat, gempatrilat, and sampatrilat. Referred to as vasopeptidase inhibitors, this latter class of compounds is described in Robl et al. (1999) *Exp. Opin. Ther. Patents* 9(12): 1665-1677.

In spite of these compounds however, there remains a need for NEP inhibitors that have improved potency, different metabolic and cleavage properties, and/or having improved oral absorption. This invention is directed to that need.

SUMMARY OF THE INVENTION

The present invention provides novel compounds that have been found to possess neprilysin (NEP) enzyme inhibition activity. Accordingly, compounds of the invention are expected to be useful and advantageous as therapeutic agents for treating conditions such as hypertension and heart failure.

One aspect of the invention relates to a compound of formula I:

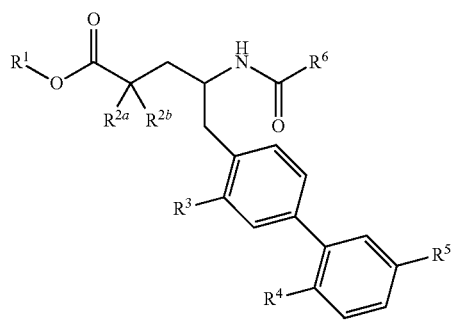

(I)

where:
$R^1$ is H, —$C_{1-8}$alkyl, —CH(CH_3)OC(O)—O-cyclohexyl, —(CH_2)_2-morpholinyl, or —CH_2-5-methyl-[1,3]dioxol-2-one;
$R^{2a}$ is —$C_{1-2}$alkyl and $R^{2b}$ is —$C_{0-2}$alkylene-NH_2, —C(O)NH_2, —COOH, —CH_2—O—$C_{1-6}$alkyl, —CN, or pyridine; or $R^{2a}$ is —CH_2OH and $R^{2b}$ is —CH_2CH_3, —(CH_2)_2CH_3, —$C_{1-2}$alkylene-OH, —(CH_2)_2NH_2, —(CH_2)_2—NHC(O)CH_3, or —CH_2CH=CH_2; or $R^{2a}$ and $R^{2b}$ are taken together to form —O—(CH_2)_2—, —(CH_2)_2—O—CH_2—, —CH_2—NH—CH_2—, —NH—(CH_2)_2—, —(CH_2)—NH—(CH_2)_2—, or —(CH_2)—N[C(O)CH_3]—(CH_2)_2—;
$R^3$, $R^4$ and $R^5$ are independently H or halo; and
$R^6$ is a heterocycle selected from the group consisting of 3H-oxazol-2-one, [1,2,4]oxadiazol-5-one, [1,2,3,5]oxatriazole, [1,2,4]triazolo[1,5-α]pyridine, triazole, pyrazole, imidazole, oxazole, isoxazole, isothiazole, pyridine, oxadiazole, and pyrimidine; the heterocycle is attached at a carbon atom; and each nitrogen atom in the heterocycle is unsubstituted or substituted with an $R^{60}$ group selected from the group consisting of —OH, —(CH_2)_2OH, —$C_{0-2}$alkylene-O—$C_{1-6}$alkyl, —$C_{1-6}$alkyl, —CHF_2, and —CF_3; and each carbon atom in the heterocycle is unsubstituted or substituted with an $R^{61}$ group independently selected from the group consisting of halo, —OH, —$C_{1-6}$alkyl, —$C_{0-2}$alkylene-O—$C_{1-6}$alkyl, —C(O)CH_3, —C(O)NH(CH_3), —C(O)N(CH_3)_2, —$C_{3-6}$cycloalkyl, —CF_3, —CH_2SO_2CH_3, —NH_2, —CH_2NH_2, —CH_2N(CH_3)_2, and phenyl substituted with methyl or halo;
with the proviso that when $R^{2a}$ is —CH_3 and $R^{2b}$ is —CH_2—O—$C_{1-6}$alkyl, then $R^6$ is not unsubstituted 3H-oxazol-2-one; unsubstituted [1,2,3]triazole; [1,2,3]triazole substituted with an $R^{60}$ group selected from the group consisting of —OH, —$C_{0-2}$alkylene-O—$C_{1-6}$alkyl, and —$C_{1-6}$alkyl; [1,2,4]triazole substituted with an $R^{61}$ group selected from the group consisting of halo and —OH; pyrazole substituted with an $R^{60}$ group that is —$C_{1-6}$alkyl; pyrazole substituted with an $R^{61}$ group selected from the group consisting of —OH, —$C_{1-6}$alkyl, —$C_{0-2}$alkylene-O—$C_{1-6}$alkyl, and —C(O)CH_3; or isoxazole substituted with an $R^{61}$ group selected from the group consisting of —OH, —$C_{1-6}$alkyl, and —$C_{0-2}$alkylene-O—$C_{1-6}$alkyl;
or a pharmaceutically acceptable salt thereof.

Another aspect of the invention relates to pharmaceutical compositions comprising a pharmaceutically acceptable carrier and a compound of the invention. Such compositions may optionally contain other therapeutic agents.

Compounds of the invention possess NEP enzyme inhibition activity, and are therefore expected to be useful as therapeutic agents for treating patients suffering from a disease or disorder that is treated by inhibiting the NEP enzyme or by increasing the levels of its peptide substrates. Thus, one aspect of the invention relates to a method of treating patients suffering from a disease or disorder that is treated by inhibiting the NEP enzyme, comprising administering to a patient a therapeutically effective amount of a compound of the invention. Another aspect of the invention relates to a method of treating hypertension, heart failure, or renal disease, comprising administering to a patient a therapeutically effective amount of a compound of the invention. Still another aspect of the invention relates to a method for inhibiting a NEP enzyme in a mammal comprising administering to the mammal, a NEP enzyme-inhibiting amount of a compound of the invention.

Since compounds of the invention possess NEP inhibition activity, they are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Yet another aspect of the invention relates to processes and intermediates useful for preparing compounds of the invention. Accordingly, another aspect of the invention relates to a process of preparing compounds of formula I, comprising the step of coupling a compound of formula 1 with a compound of formula 2:

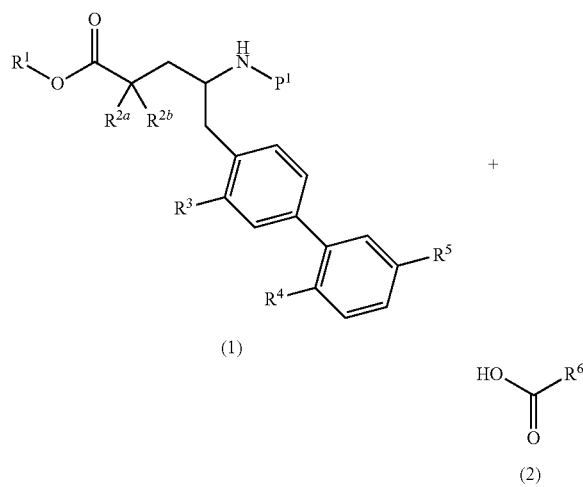

to produce a compound of formula I; where $P^1$ is H or an amino-protecting group selected from the group consisting of t-butoxycarbonyl, trityl, benzyloxycarbonyl, 9-fluorenylmethoxycarbonyl, formyl, trimethylsilyl, and t-butyldimethylsilyl; and where the process further comprises deprotecting the compound of formula 1 when $P^1$ is an amino protecting group; and where $R^1$, $R^{2a}$, $R^{2b}$, and $R^3$-$R^6$ are as defined for formula I. In other aspects, the invention relates to products prepared by any of the processes described herein, as well as novel intermediates used in such process. In one aspect of the invention novel intermediates have formula 1, or a salt thereof, as defined herein.

Yet another aspect of the invention relates to the use of a compound of formula I or a pharmaceutically acceptable salt thereof, for the manufacture of a medicament, especially for the manufacture of a medicament useful for treating hypertension, heart failure, or renal disease. Another aspect of the invention relates to use of a compound of the invention for inhibiting a NEP enzyme in a mammal Still another aspect of the invention relates to the use of a compound of the invention as a research tool. Other aspects and embodiments of the invention are disclosed herein.

DETAILED DESCRIPTION OF THE INVENTION

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —$C_{1-6}$alkyl, meaning an alkyl group having from 1 to 6 carbon atoms where the carbon atoms are in any acceptable configuration. Representative alkyl groups include, by way of example, methyl, ethyl, n-propyl, isopropyl, n-butyl, s-butyl, isobutyl, t-butyl, n-pentyl, n-hexyl, and the like.

The term "alkylene" means a divalent saturated hydrocarbon group that may be linear or branched. Unless otherwise defined, such alkylene groups typically contain from 0 to 10 carbon atoms and include, for example, —$C_{0-1}$alkylene-, —$C_{0-2}$alkylene-, —$C_{1-2}$alkylene-, —$C_{1-6}$alkylene-, and so form. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —$C_{0-2}$alkylene-, such terms are intended to include the absence of carbon atoms, that is, the alkylene group is not present except for a covalent bond attaching the groups separated by the alkylene term.

The term "cycloalkyl" means a monovalent saturated carbocyclic hydrocarbon group. Unless otherwise defined, such cycloalkyl groups typically contain from 3 to 10 carbon atoms and include, for example, —$C_{3-5}$cycloalkyl, —$C_{3-6}$cycloalkyl and —$C_{3-7}$cycloalkyl. Representative cycloalkyl groups include, by way of example, cyclopropyl, cyclobutyl, cyclopentyl, cyclohexyl and the like.

The term "halo" means fluoro, chloro, bromo and iodo.

The term "heterocycle" is intended to include monovalent unsaturated (aromatic) heterocycles having a single ring or two fused rings as well as monovalent saturated and partially unsaturated groups having a single ring or multiple condensed rings. The heterocycle ring can contain from 3 to 15 total ring atoms, of which 1 to 14 are ring carbon atoms (e.g., —$C_{1-7}$heterocycle, —$C_{3-5}$heterocycle, —$C_{2-6}$heterocycle, —$C_{3-12}$heterocycle, —$C_{5-9}$heterocycle, —$C_{1-9}$heterocycle, —$C_{1-11}$heterocycle, and —$C_{1-14}$heterocycle), and 1 to 4 are ring heteroatoms selected from nitrogen, oxygen or sulfur.

Typically, however, the heterocycle ring contains from 3 to 10 total ring atoms, of which 1 to 9 are ring carbon atoms, and 1 to 4 are ring heteroatoms. Exemplary heterocycles include, for example, —$C_{1-7}$heterocycle, —$C_{3-5}$heterocycle, —$C_{2-6}$heterocycle, —$C_{3-12}$heterocycle, —$C_{5-9}$heterocycle, —$C_{1-9}$heterocycle, —$C_{1-11}$heterocycle, and —$C_{1-14}$heterocyle. Exemplary heterocycles include 3H-oxazol-2-one, 4H-[1,2,4]oxadiazol-5-one, [1,2,3,5]oxatriazole, triazole, pyrazole, oxazole, isoxazole, isothiazole, pyridine, oxadiazole, and pyrimidine.

When a heterocycle is described as being "attached at a carbon atom," it means that the point of attachment is at any available carbon ring atom. Examples of heterocycles attached at a carbon atom are the triazole rings illustrated below:

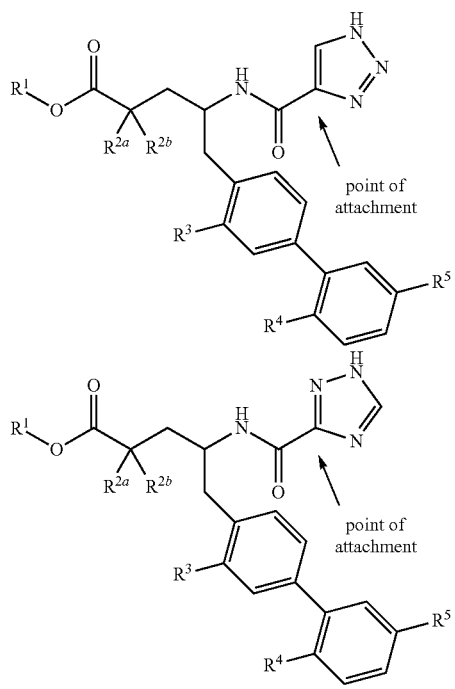

The term "optionally substituted" means that group in question may be unsubstituted or it may be substituted one or several times, such as 1 to 3 times, or 1 to 5 times, or 1 to 8 times. For example, a heterocycle that is "optionally substituted" with one or two halo or hydroxyl groups, may be unsubstituted, or it may contain one halo group, one hydroxyl group, two halo groups, two hydroxyl group, or one halo group and one hydroxyl group. Generally, such groups can be positioned on any available atom provided that the normal valency of the designated atom is not exceeded and that the substitution results in a stable moiety. Such groups may be specified as being on an available nitrogen atom or an available carbon atom.

When a nitrogen atom in a heterocycle is described as being "substituted," it means that the hydrogen atom on the nitrogen is replaced with a selected moiety, provided that the normal valency of the nitrogen is not exceeded, and that the substitution results in a stable ring. Similarly, when a nitrogen atom in a heterocycle is described as being "unsubstituted," it means that a hydrogen atom is on the nitrogen or the valency of the nitrogen has already been met without substitution (for example the nitrogen atom in a pyridine ring). For example, triazole has three nitrogen atoms present. The first triazole depicted has all unsubstituted nitrogen atoms since two nitrogen atoms have their valency met without substitution and one nitrogen atom has a hydrogen present. On the other hand, the second triazole depicted is substituted on the nitrogen atom with an $R^{60}$ group:

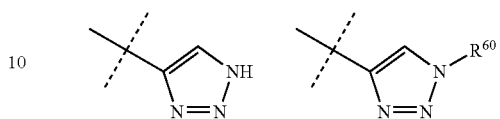

There are instances where the heterocycle will not be substituted with an $R^{60}$ group. For example, pyridine has one nitrogen atom present, but the valency of the nitrogen atom is met without substitution:

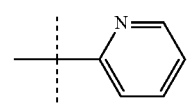

Similarly, triazole has two carbon atoms present, with one forming the point of attachment to the remainder of the compound. The first triazole has an "unsubstituted" carbon atom, while the second triazole is substituted on the carbon atom with an $R^{61}$ group, and the third triazole is substituted on the carbon atom with an $R^{61}$ group and on the nitrogen atom with an $R^{60}$ group:

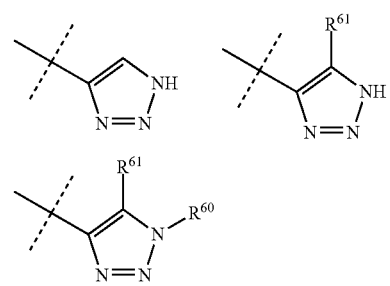

When a carbon atom in a heterocycle is described as being "substituted," it means that the hydrogen atom on the carbon is replaced with a selected moiety, provided that the normal valency of the carbon is not exceeded, and that the substitution results in a stable ring. Similarly, when a carbon atom in a heterocycle is described as being "unsubstituted," it means that a hydrogen atom is on the carbon atom or its valency has already been met without substitution (for example the oxo group on 4H-[1,2,4]oxadiazol-5-one). For example, pyrazole has three carbon atoms present, with one forming the point of attachment to the remainder of the compound, such that it is not available for substitution. The first pyrazole has two "unsubstituted" carbon atoms, while the second pyrazole has a first "unsubstituted" carbon atom and a second carbon atom that is substituted with an $R^{61}$ group, the third pyrazole is substituted on both carbon atoms with an $R^{61}$ group (which may be the same or different; depicted at $R^{61a}$ and $R^{61b}$), and the fourth pyrazole is substituted on both carbon atoms with an $R^{61}$ group:

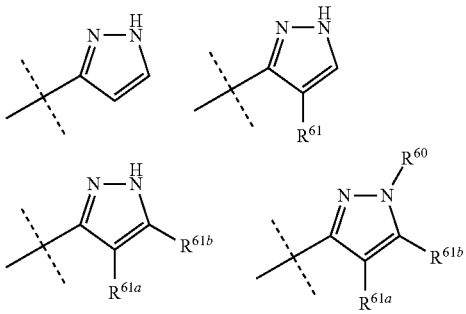

There are instances where the heterocycle will not be substituted with an $R^{61}$ group. For example, although 4H-[1,2,4]oxadiazol-5-one has two carbon atoms present, one carbon atom forms the point of attachment to the remainder of the compound and the other carbon atom is already substituted with an oxo group and so is not available for substitution with an $R^{61}$ group:

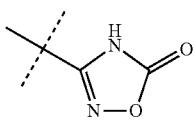

Similarly, [1,2,3,5]oxatriazole has one carbon atom present, but it forms the point of attachment to the remainder of the compound:

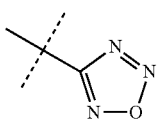

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which the crystalline compound is being evaluated or being used in an assay, for example an animal model.

All other terms used herein are intended to have their ordinary meaning as understood by those of ordinary skill in the art to which they pertain.

In one aspect, the invention relates to compounds of formula I:

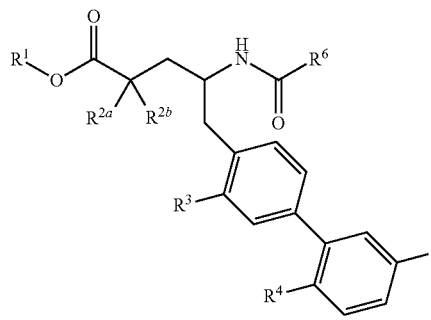

(I)

or a pharmaceutically acceptable salt thereof.

As used herein, the term "compound of the invention" includes all compounds encompassed by formula I and species thereof. Similarly, reference to compound of a given formula is intended to include all species. In addition, the compounds of the invention may also contain several basic or acidic groups (for example, amino or carboxyl groups) and therefore, such compounds can exist as a free base, free acid, or in various salt forms. All such salt forms are included within the scope of the invention. Furthermore, the compounds of the invention may also exist as prodrugs. Accordingly, those skilled in the art will recognize that reference to a compound herein, for example, reference to a "compound of the invention" or a "compound of formula I" includes a compound of formula I as well as pharmaceutically acceptable salts and prodrugs of that compound unless otherwise indicated. Further, the term "or a pharmaceutically acceptable salt and/or prodrug thereof" is intended to include all permutations of salts and prodrugs, such as a pharmaceutically acceptable salt of a prodrug. Furthermore, solvates of compounds of formula I are included within the scope of this invention.

The compounds of the invention contain one or more chiral centers and therefore, these compounds may be prepared and used in various stereoisomeric forms. In some embodiments, in order to optimize the therapeutic activity of the compounds of the invention, e.g., to treat hypertension, it may be desirable that the carbon atoms have a particular (R,R), (S,S), (S,R), or (R,S) configuration or are enriched in a stereoisomeric form having such configuration. In other embodiments, the compounds of the invention are present as racemic mixtures. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Thus, for example, the term "compound of formula I" is intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified. For example, if triazole is depicted as ($R^{60}$ being hydrogen):

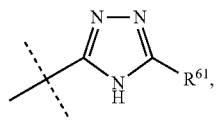

it is understood that the compound may also exist in a tautomeric form such as:

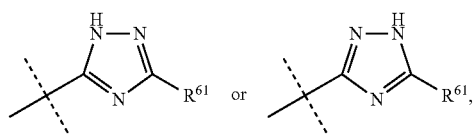

and that all such forms are covered by the invention.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^{2}H$, $^{3}H$, $^{13}C$, $^{14}C$, $^{15}N$, $^{18}O$, $^{17}O$, $^{35}S$, $^{36}Cl$, and $^{18}F$. Of particular interest are compounds of formula I enriched in tritium or carbon-14 which can be used, for example, in tissue distribution studies;

compounds of the invention enriched in deuterium especially at a site of metabolism resulting, for example, in compounds having greater metabolic stability; and compounds of formula I enriched in a positron emitting isotope, such as $^{11}C$, $^{18}F$, $^{15}O$ and $^{13}N$, which can be used, for example, in Positron Emission Topography (PET) studies.

The nomenclature used herein to name the compounds of the invention is illustrated in the Examples herein. This nomenclature has been derived using the commercially available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, this invention relates to compounds of formula I:

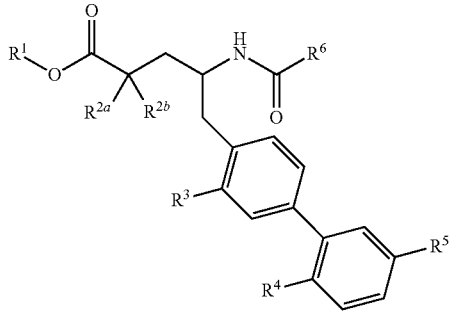

$R^1$ is selected from the group consisting of H, —$C_{1-8}$alkyl, —CH(CH$_3$)OC(O)—O—cyclohexyl, —(CH$_2$)$_2$-morpholinyl, and —CH$_2$-5-methyl-[1,3]dioxol-2-one. In one embodiment, $R^1$ is H. In one embodiment, $R^1$ is —$C_{1-8}$alkyl, for example —CH$_2$CH$_3$, —CH(CH$_3$)$_2$, —(CH$_2$)$_3$CH$_3$, and —(CH$_2$)$_5$CH$_3$. When $R^1$ is —$C_{1-8}$alkyl, the compound of formula I can be referred to as an alkyl ester, for example an ethyl ester. In one embodiment, $R^1$ is —CH(CH$_3$)OC(O)—O-cyclohexyl:

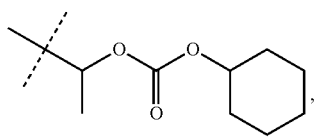

and the compound of formula I can be referred to as a cilexetil ester. In another embodiment, $R^1$ is —(CH$_2$)$_2$-morpholinyl:

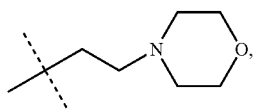

and the compound of formula I can be referred to as a 2-morpholinoethyl or mofetil ester. In yet another one embodiment, $R^1$ is —CH$_2$-5-methyl-[1,3]dioxol-2-one:

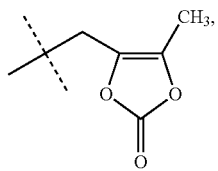

and the compound of formula I can be referred to as a medoxomil ester.

$R^{2a}$ is —$C_{1-2}$alkyl and $R^{2b}$ is —$C_{0-2}$alkylene-NH$_2$, —C(O)NH$_2$, —COOH, —CH$_2$—O—$C_{1-6}$alkyl, —CN, or pyridine; or $R^{2a}$ is —CH$_2$OH and $R^{2b}$ is —CH$_2$CH$_3$, —(CH$_2$)$_2$CH$_3$, —$C_{1-2}$alkylene-OH, —(CH$_2$)$_2$NH$_2$, —(CH$_2$)$_2$—NHC(O)CH$_3$, or —CH$_2$CH=CH$_2$; or $R^{2a}$ and $R^{2b}$ are taken together to form —O—(CH$_2$)$_2$—, —(CH$_2$)$_2$—O—CH$_2$—, —CH$_2$—NH—CH$_2$—, —NH—(CH$_2$)$_2$—, —(CH$_2$)$_2$—NH—CH$_2$—, or —(CH$_2$)$_2$—N(C(O)CH$_3$)—CH$_2$—.

In one embodiment, $R^{2a}$ is —$C_{1-2}$alkyl and $R^{2b}$ is —$C_{0-2}$alkylene-NH$_2$ (e.g., —NH$_2$, —CH$_2$NH$_2$, and —(CH$_2$)$_2$NH$_2$), —C(O)NH$_2$, —COOH, —CH$_2$—O—$C_{1-6}$alkyl (e.g., —CH$_2$—O—CH$_3$ or —CH$_2$—O—CH$_2$CH$_3$), —CN, or pyridine. Examples of the $R^{2b}$ pyridine group include:

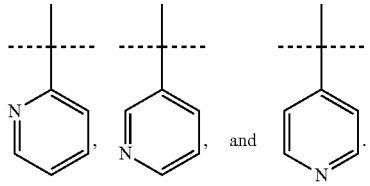

In more specific embodiments $R^{2a}$ is —CH$_3$ and $R^{2b}$ is —NH$_2$, —CH$_2$NH$_2$, —C(O)NH$_2$, —COOH, —CH$_2$—O—CH$_3$, —CH$_2$—O—CH$_2$CH$_3$, or —CN; or $R^{2a}$ is —CH$_2$CH$_3$ and $R^{2b}$ is —CN.

In another embodiment, $R^{2a}$ is —CH$_2$OH and $R^{2b}$ is —CH$_2$CH$_3$, —(CH$_2$)$_2$CH$_3$, —$C_{1-2}$alkylene-OH (e.g., —(CH$_2$)$_2$—OH), —(CH$_2$)$_2$NH$_2$, —(CH$_2$)$_2$—NHC(O)CH$_3$, or —CH$_2$CH=CH$_2$.

In still another embodiment, $R^{2a}$ and $R^{2b}$ are taken together to form —O—(CH$_2$)$_2$—, —(CH$_2$)$_2$—O—CH$_2$—, —CH$_2$—N—CH$_2$—, —N—(CH$_2$)$_2$—, —(CH$_2$)—NH—(CH$_2$)$_2$—, or —(CH$_2$)—N[C(O)CH$_3$]—(CH$_2$)$_2$—.

$R^3$ is selected from the group consisting of H and halo, and in one embodiment, $R^3$ is H. $R^4$ is selected from the group consisting of H and halo, and in one embodiment, $R^4$ is F. $R^5$ is selected from the group consisting of H and halo, and in one embodiment, $R^5$ is H, Br, or Cl, and in another embodiment $R^5$ is Cl. In other embodiments, $R^3$ is H, $R^4$ is F, and $R^5$ is Cl; or $R^3$ and $R^4$ are H and $R^5$ is Br or Cl; or $R^3$, $R^4$, and $R^5$ are H; or $R^3$ is Cl, $R^4$ is F, and $R^5$ is Cl; or $R^3$ is H, $R^4$ is F, and $R^5$ is H.

$R^6$ is a heterocycle selected from the group consisting of 3H-oxazol-2-one, [1,2,4]oxadiazol-5-one, [1,2,3,5]oxatriazole, [1,2,4]triazolo[1,5-α]pyridine, triazole, pyrazole, imidazole, oxazole, isoxazole, isothiazole, pyridine, oxadiazole, and pyrimidine, where the heterocycle is attached at a carbon atom. However, when $R^{2a}$ is —CH$_3$ and $R^{2b}$ is —CH$_2$—O—$C_{1-6}$alkyl, then $R^6$ is not unsubstituted 3H-oxazol-2-one; unsubstituted [1,2,3]triazole; [1,2,3]triazole substituted with an $R^{60}$ group selected from the group consisting of —OH, —$C_{0-2}$alkylene-O—$C_{1-6}$alkyl, and —$C_{1-6}$alkyl; [1,2,4]triazole substituted with an $R^{61}$ group selected from the group consisting of halo and —OH;

pyrazole substituted with an $R^{60}$ group that is —$C_{1-6}$alkyl; pyrazole substituted with an $R^{61}$ group selected from the group consisting of —OH, —$C_{1-6}$alkyl, —$C_{0-2}$alkylene-O—$C_{1-6}$alkyl, and —C(O)CH$_3$; or isoxazole substituted with an $R^{61}$ group selected from the group consisting of —OH, —$C_{1-6}$alkyl, and —$C_{0-2}$alkylene-O—$C_{1-6}$alkyl.

In one embodiment, $R^6$ is 3H-oxazol-2-one, 4H-[1,2,4]oxadiazol-5-one, [1,2,3,5]oxatriazole, [1,2,3]triazole, [1,2,4]triazole, pyrazole, imidazole, oxazole, isoxazole, isothiazole, pyridine, oxadiazole, or pyrimidine; and in one particular embodiment, $R^6$ is 4H-[1,2,4]oxadiazol-5-one, [1,2,3]triazole, [1,2,4]triazole, pyrazole, oxazole, pyridine, or pyrimidine.

Each nitrogen atom in the heterocycle is unsubstituted or substituted with an $R^{60}$ group selected from the group consisting of —OH, —(CH$_2$)$_2$OH, —$C_{0-2}$alkylene-O—$C_{1-6}$alkyl (e.g., —OCH$_3$ or —OCH$_2$CH$_3$), —$C_{1-6}$alkyl (e.g., —CH$_3$), —CHF$_2$, and —CF$_3$. In one embodiment, the nitrogen atoms in the heterocycle are unsubstituted. In another embodiment, $R^{60}$ is —OH, —(CH$_2$)$_2$OH, —OCH$_3$, —OCH$_2$CH$_3$, —CH$_3$, —CHF$_2$, and —CF$_3$; and in yet another embodiment, one nitrogen atom in the heterocycle is substituted with an $R^{60}$ moiety. In one particular embodiment, $R^{60}$ is —(CH$_2$)$_2$OH, —OCH$_3$, —OCH$_2$CH$_3$, or —CHF$_2$.

Each carbon atom in the heterocycle is unsubstituted or substituted with an $R^{61}$ group independently selected from the group consisting of halo, —OH, —$C_{1-6}$alkyl, —$C_{0-2}$alkylene-O—$C_{1-6}$alkyl, —C(O)CH$_3$, —C(O)NH(CH$_3$), —C(O)N(CH$_3$)$_2$, —$C_{3-6}$cycloalkyl (e.g., cyclopropyl, cyclobutyl, cyclopentyl, and cyclohexyl), —CF$_3$, —CH$_2$SO$_2$CH$_3$, —NH$_2$, —CH$_2$NH$_2$, —CH$_2$N(CH$_3$)$_2$, and phenyl substituted with methyl. In one embodiment, the carbon atoms in the heterocycle are unsubstituted; and in another embodiment, one carbon atom in the heterocycle is substituted with an $R^{61}$ group. In another embodiment, $R^{61}$ is chloro, —OH, —CH$_3$, —CH$_2$CH$_3$, —(CH$_2$)$_2$CH$_3$, —CH(CH$_3$)$_2$, —OCH$_3$, —OCH$_2$CH$_3$, —CH$_2$—OCH$_3$, —C(O)CH$_3$, —C(O)NH(CH$_3$), —C(O)N(CH$_3$)$_2$, cyclopropyl, —CF$_3$, —CH$_2$SO$_2$CH$_3$, —NH$_2$, —CH$_2$NH$_2$, —CH$_2$N(CH$_3$)$_2$, or phenyl substituted with methyl or fluoro. In another embodiment, two carbon atoms in the heterocycle are substituted with $R^{61}$ groups, which may be the same or different; and in one specific embodiment, the $R^{61}$ moiety on a first carbon is fluoro, —OH, —CH$_3$, —$C_{0-2}$alkylene-O—$C_{1-6}$alkyl, —C(O)CH$_3$, —$C_{3-6}$cycloalkyl, —CF$_3$, —CH$_2$SO$_2$CH$_3$, —NH$_2$, or —CH$_2$N(CH$_3$)$_2$ and the $R^{61}$ moiety on a second carbon is halo, —OH, —CH$_3$, —O—CH$_2$CH$_3$, —C(O)CH$_3$, cyclopropyl, —CF$_3$, —CH$_2$SO$_2$CH$_3$, —NH$_2$, —CH$_2$N(CH$_3$)$_2$, or phenyl substituted with methyl or halo. In one particular embodiment, $R^{61}$ is chloro, —CH$_3$, —C(O)CH$_3$, cyclopropyl, or —CF$_3$.

In one embodiment, $R^6$ is 3H-oxazol-2-one, for example:

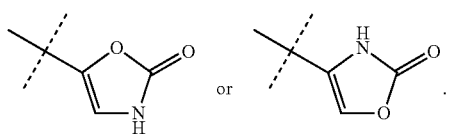

In one embodiment, $R^6$ is [1,2,4]oxadiazol-5-one, for example 4H-[1,2,4]oxadiazol-5-one or 2H-[1,2,4]oxadiazol-5-one:

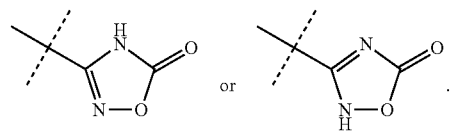

In one embodiment, $R^6$ is [1,2,3,5]oxatriazole, for example:

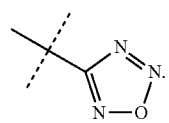

In one embodiment, $R^6$ is [1,2,4]triazolo[1,5-α]pyridine, for example:

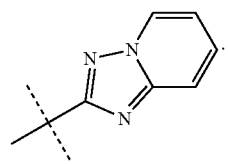

In one particular embodiment, $R^6$ is a [1,2,4]triazolo[1,5-α]pyridine ring such as:

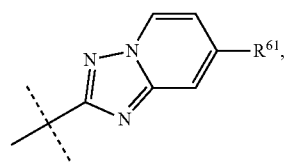

specific examples of which include:

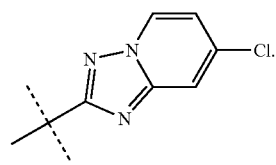

In one embodiment, $R^6$ is [1,2,3]triazole or [1,2,4]triazole, for example:

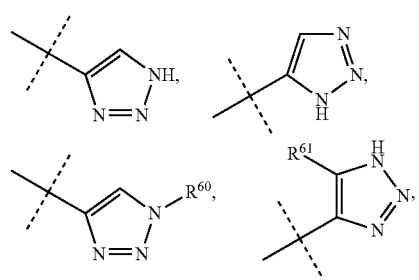

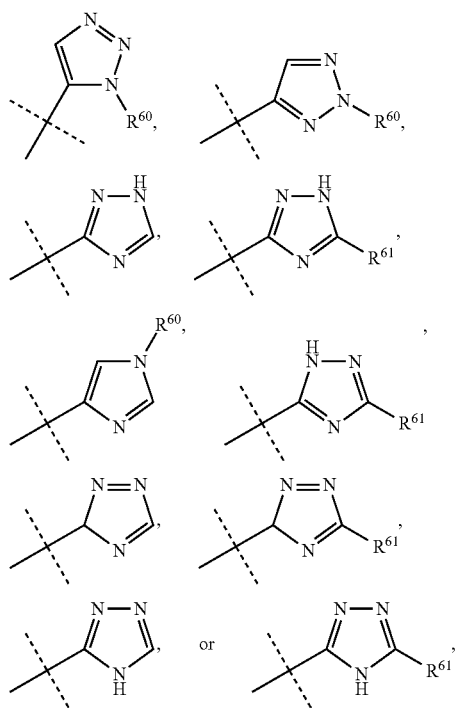
specific examples of which include:
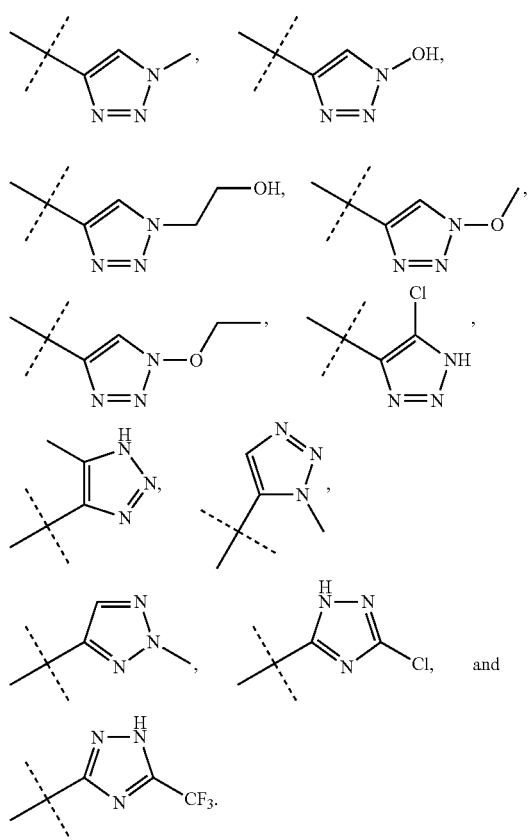
In one particular embodiment, $R^6$ is a triazole ring such as:
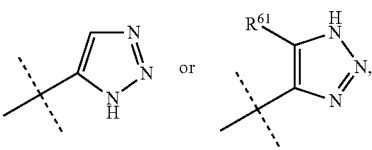
specific examples of which include:
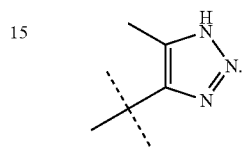
In one embodiment, $R^6$ is a pyrazole ring, for example:
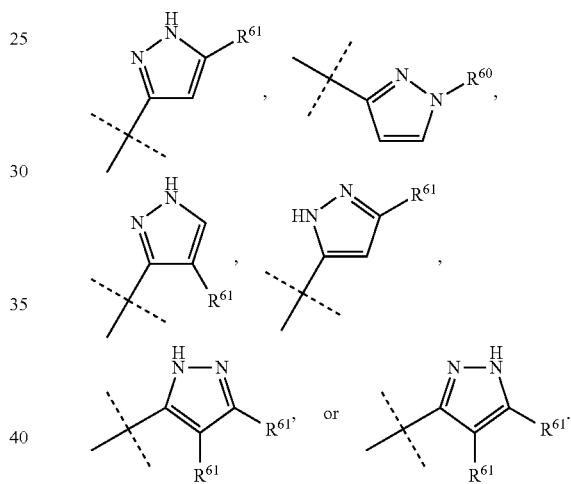
In one particular embodiment, $R^6$ is a pyrazole ring such as:
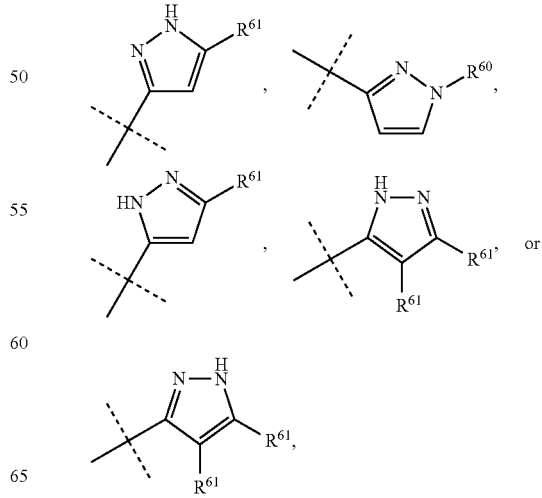

specific examples of which include:
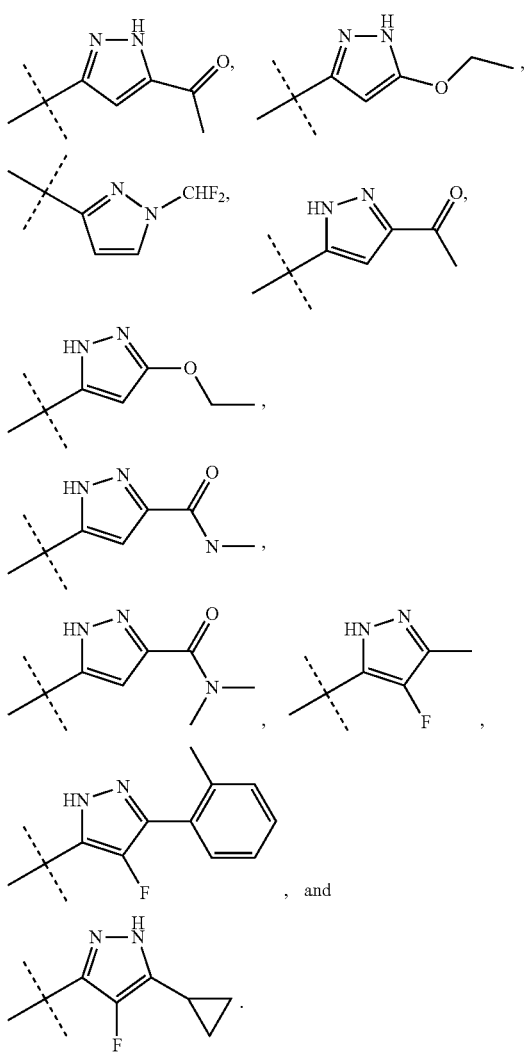
In one embodiment, $R^6$ is an imidazole ring, for example:
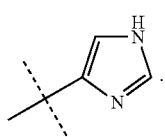
In one particular embodiment, $R^6$ is an imidazole ring such as:
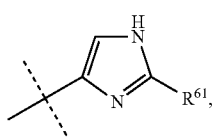
specific examples of which include:
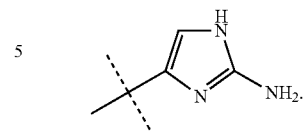
In one embodiment, $R^6$ is an oxazole ring, for example:
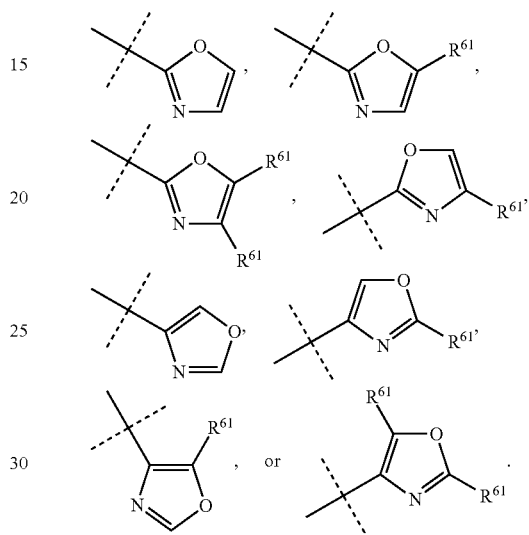
In one particular embodiment, $R^6$ is an oxazole ring such as:
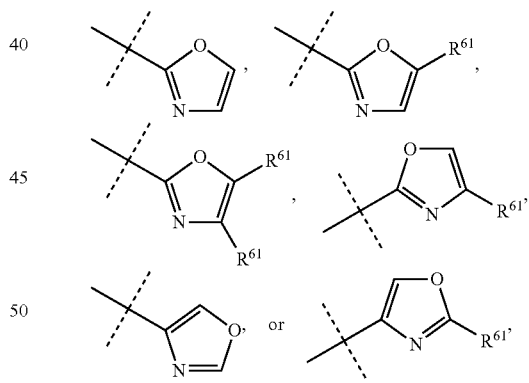
specific examples of which include:
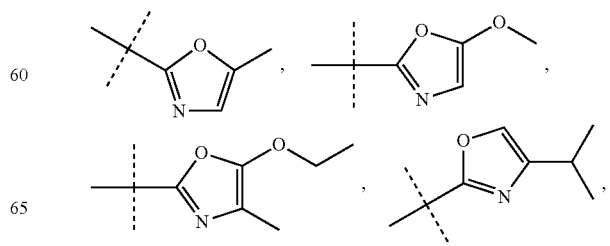

-continued

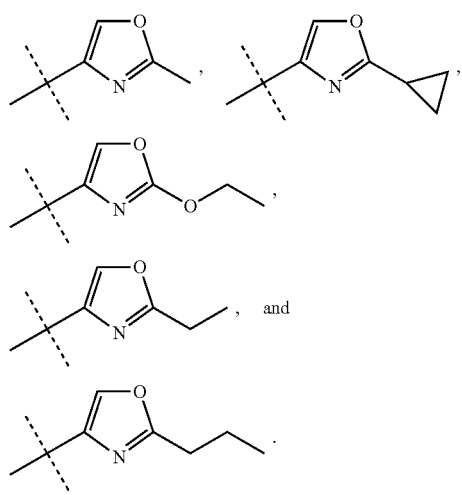

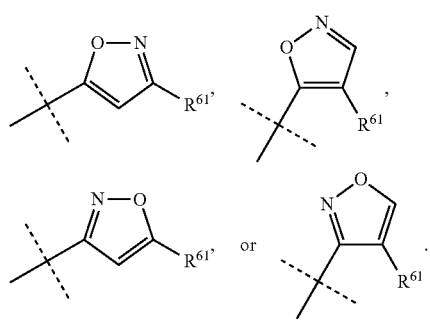

In one embodiment, R⁶ is an isoxazole ring, for example:

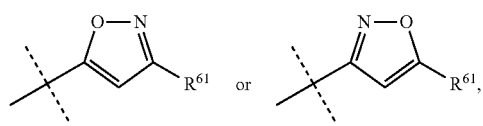

In one particular embodiment, R⁶ is an isoxazole ring such as:

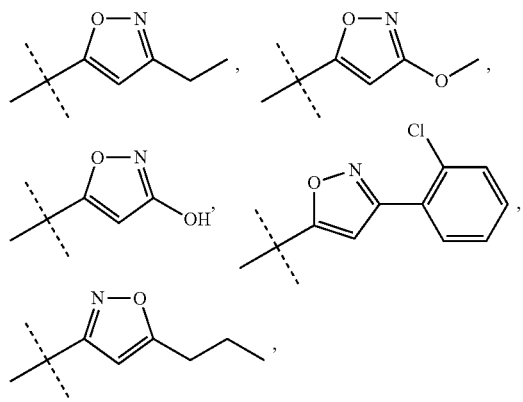

specific examples of which include:

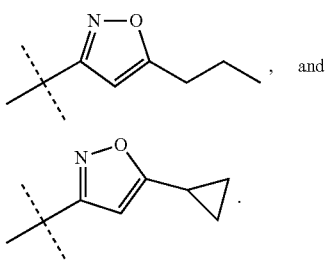

In one embodiment, R⁶ is an isothiazole ring, for example:

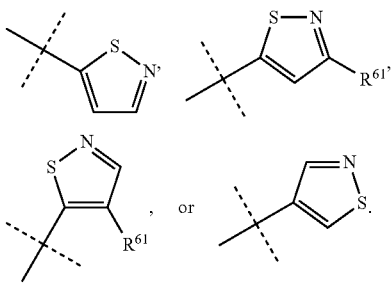

In one particular embodiment, R⁶ is an isothiazole ring such as:

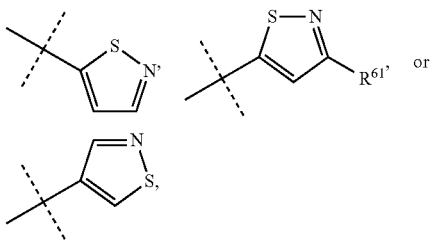

specific examples of which include:

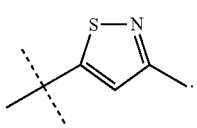

In one embodiment, R⁶ is a pyridine ring, for example:

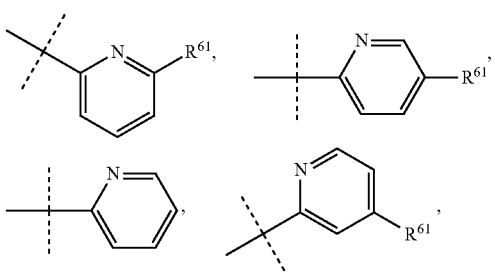

-continued

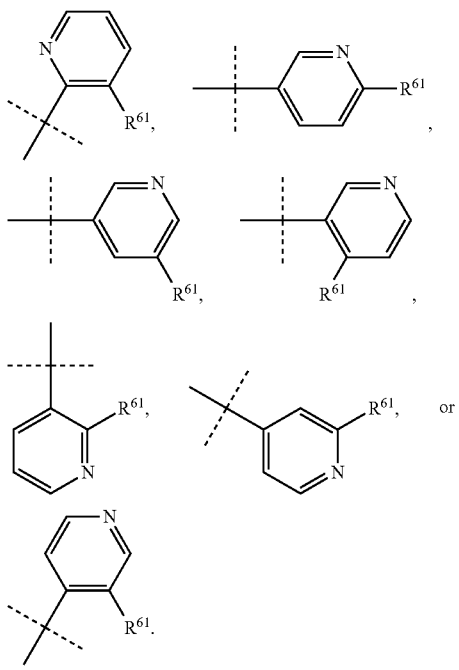

In one particular embodiment, $R^6$ is a pyridine ring such as:

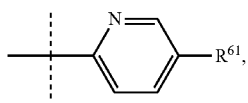

specific examples of which include:

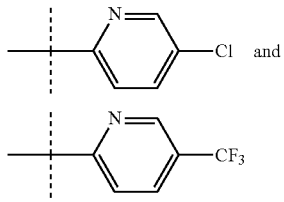

In one embodiment, $R^6$ is oxadiazole, for example [1,2,4]oxadiazole or [1,3,4]oxadiazole:

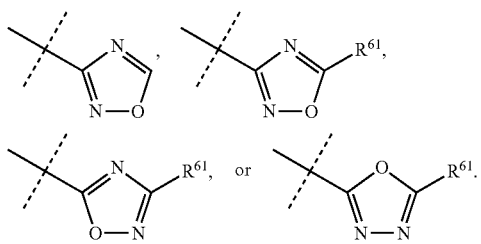

In one embodiment, $R^6$ is a pyrimidine ring, for example:

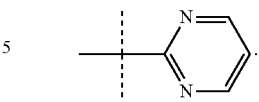

In another embodiment of the invention, $R^{2a}$ is —CH$_3$ and $R^{2b}$ is —C$_{0-2}$alkylene-NH$_2$, —C(O)NH$_2$, or —COOH; or $R^{2a}$ is —CH$_2$OH and $R^{2b}$ is —CH$_2$CH$_3$, —(CH$_2$)$_2$CH$_3$, —C$_{1-2}$alkylene-OH, —(CH$_2$)$_2$NH$_2$, —(CH$_2$)$_2$—NHC(O)CH$_3$, or —CH$_2$CH=CH$_2$; or $R^{2a}$ and $R^{2b}$ are taken together to form —O—(CH$_2$)$_2$—, —(CH$_2$)$_2$—O—CH$_2$—, —CH$_2$—N—CH$_2$—, —N—(CH$_2$)$_2$—, —(CH$_2$)—NH—(CH$_2$)$_2$—, or —(CH$_2$)—N(COOH)—(CH$_2$)$_2$—; $R^6$ is a heterocycle selected from the group consisting of 3H-oxazol-2-one, [1,2,4]oxadiazol-5-one, [1,2,3,5]oxatriazole, [1,2,4]triazolo[1,5-α]pyridine, triazole, pyrazole, imidazole, oxazole, isoxazole, isothiazole, pyridine, oxadiazole, and pyrimidine; the heterocycle is attached at a carbon atom; and each nitrogen atom in the heterocycle is unsubstituted or substituted with an $R^{60}$ group selected from the group consisting of —OH, —(CH$_2$)$_2$OH, —C$_{0-2}$alkylene-O—C$_{1-6}$alkyl, —C$_{1-6}$alkyl, —CHF$_2$, and —CF$_3$; and each carbon atom in the heterocycle is unsubstituted or substituted with an $R^{61}$ group independently selected from the group consisting of halo, —OH, —C$_{1-6}$alkyl, —C$_{0-2}$alkylene-O—C$_{1-6}$alkyl, —C(O)CH$_3$, —C(O)NH(CH$_3$), —C(O)N(CH$_3$)$_2$, —C$_{3-6}$cycloalkyl, —CF$_3$, —CH$_2$SO$_2$CH$_3$, —NH$_2$, —CH$_2$N(CH$_3$)$_2$, and phenyl substituted with methyl or halo; and $R^1$, $R^3$, $R^4$ and $R^5$, are as defined for the compounds of formula I.

In still another embodiment of the invention, $R^{2a}$ is —CH$_3$ and $R^{2b}$ is —CH$_2$—O—C$_{1-6}$alkyl; $R^6$ is a heterocycle selected from the group consisting of 3H-oxazol-2-one, [1,2,4]oxadiazol-5-one, [1,2,3,5]oxatriazole, [1,2,4]triazolo[1,5-α]pyridine, triazole, pyrazole, imidazole, oxazole, isoxazole, isothiazole, pyridine, oxadiazole, and pyrimidine; the heterocycle is attached at a carbon atom; and each nitrogen atom in the heterocycle is unsubstituted or substituted with an $R^{60}$ group selected from the group consisting of —OH, —(CH$_2$)$_2$OH, —C$_{0-2}$alkylene-O—C$_{1-6}$alkyl, —C$_{1-6}$alkyl, —CHF$_2$, and —CF$_3$; and each carbon atom in the heterocycle is unsubstituted or substituted with an $R^{61}$ group independently selected from the group consisting of halo, —OH, —C$_{1-6}$alkyl, —C$_{0-2}$alkylene-O—C$_{1-6}$alkyl, —C(O)CH$_3$, —C(O)NH(CH$_3$), —C(O)N(CH$_3$)$_2$, —C$_{3-6}$cycloalkyl, —CF$_3$, —CH$_2$SO$_2$CH$_3$, —NH$_2$, —CH$_2$N(CH$_3$)$_2$, and phenyl substituted with methyl or halo; with the proviso that $R^6$ is not unsubstituted 3H-oxazol-2-one; unsubstituted [1,2,3]triazole; [1,2,3]triazole substituted with an $R^{60}$ group selected from the group consisting of —OH, —C$_{0-2}$alkylene-O—C$_{1-6}$alkyl, and —C$_{1-6}$alkyl; [1,2,4]triazole substituted with an $R^{61}$ group selected from the group consisting of halo and —OH; pyrazole substituted with an $R^{60}$ group that is —C$_{1-6}$alkyl; pyrazole substituted with an $R^{61}$ group selected from the group consisting of —OH, —C$_{1-6}$alkyl, —C$_{0-2}$alkylene-O—C$_{1-6}$alkyl, and —C(O)CH$_3$; or isoxazole substituted with an $R^{61}$ group selected from the group consisting of —OH, —C$_{1-6}$alkyl, and —C$_{0-2}$alkylene-O—C$_{1-6}$alkyl; and $R^1$, $R^3$, $R^4$ and $R^5$, are as defined for the compounds of formula I.

In addition, particular compounds of formula I that are of interest include those set forth in the Examples below, as well as pharmaceutically acceptable salts thereof.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. In some instances, reactions were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, reactions were conducted at room temperature and the temperature was actually measured and recorded. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Fourth Edition, Wiley, New York, 2006, and references cited therein.

Carboxy-protecting groups are suitable for preventing undesired reactions at a carboxy group, and examples include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Amino-protecting groups are suitable for preventing undesired reactions at an amino group, and examples include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Hydroxyl-protecting groups are suitable for preventing undesired reactions at a hydroxyl group, and examples include, but are not limited to, $C_{1-6}$alkyls, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenylmethyl (Fm), and diphenylmethyl (benzhydryl, DPM); and the like.

Standard deprotection techniques and reagents are used to remove the protecting groups, and may vary depending upon which group is used. For example, a BOC amino-protecting group can be removed using an acidic reagent such as TFA in DCM or HCl in 1,4-dioxane, while a Cbz amino-protecting group can be removed by employing catalytic hydrogenation conditions such as $H_2$ (1 atm) and 10% Pd/C in an alcoholic solvent ("$H_2$/Pd/C").

Suitable bases for use in these schemes include, by way of illustration and not limitation, potassium carbonate, calcium carbonate, sodium carbonate, triethylamine ($Et_3N$), pyridine, 1,8-diazabicyclo-[5.4.0]undec-7-ene (DBU), N,N-diisopropylethylamine (DIPEA), 4-methylmorpholine, sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), N,N-dimethylacetamide (DMA), dimethyl sulfoxide (DMSO), toluene, dichloromethane (DCM), chloroform ($CHCl_3$), carbon tetrachloride ($CCl_4$), 1,4-dioxane, methanol, ethanol, water, diethyl ether, acetone, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), N,N,N',N'-tetramethyl-O-(7-azabenzotriazol-1-yl)uronium hexafluorophosphate (HATU), 1,3-dicyclohexylcarbodiimide (DCC), N-(3-dimethylaminopropyl)-N'-ethylcarbodiimide (EDC), carbonyldiimidazole (CDI), 1-hydroxybenzotriazole (HOBt), and the like. Coupling reactions are conducted in an inert diluent in the presence of a base such as DIPEA, and are performed under conventional amide bond-forming conditions.

All reactions are typically conducted at a temperature within the range of about −78 C to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, chloroform); washing (for example, with saturated aqueous NaCl, saturated aqueous $NaHCO_3$, $Na_2CO_3$ (5%), $CHCl_3$ or 1M NaOH); drying (for example, over $MgSO_4$, over $Na_2SO_4$, or in vacuo); filtering; crystallizing (for example, from EtOAc and hexanes); being concentrated (for example, in vacuo); and/or purification (e.g., silica gel chromatography, flash chromatography, preparative HPLC, reverse phase-HPLC, or crystallization).

By way of illustration, compounds of formula I, as well as their salts, can be prepared as shown in Schemes I and II.

Scheme I

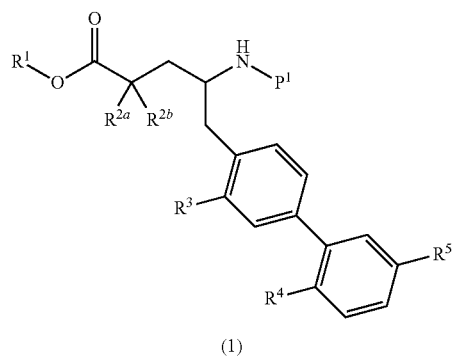

(1)

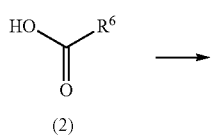

(2)

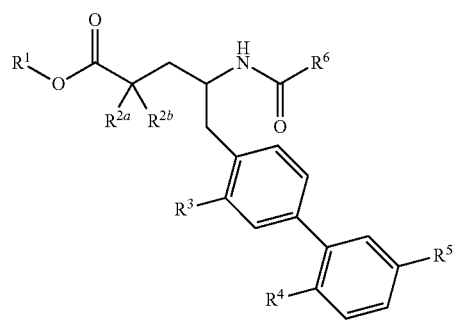

Scheme I is a is a coupling reaction between a compound of formula 1 ($R^1$, $R^{2a}$, $R^{2b}$, and $R^3$-$R^5$ are as defined for formula I and $P^1$ is H or a suitable amino-protecting group) and a compound of formula 2 ($R^6$ is as defined for formula I). When $P^1$ is an amino protecting group, the process further comprises deprotecting the compound, before or in situ with the coupling step. Exemplary coupling reagents include HATU, and HOBt with EDC. Generally, this reaction is conducted in the presence of a base such as DIPEA or 4-methylmorpholine, and an inert diluent or solvents such as DMF or DMA. Preparation of various amine starting materials (Compound 1) are illustrated in the Examples. The carboxylic acid starting materials (Compound 2) are generally commercially available or can be prepared using procedures that are known in the art.

Scheme II

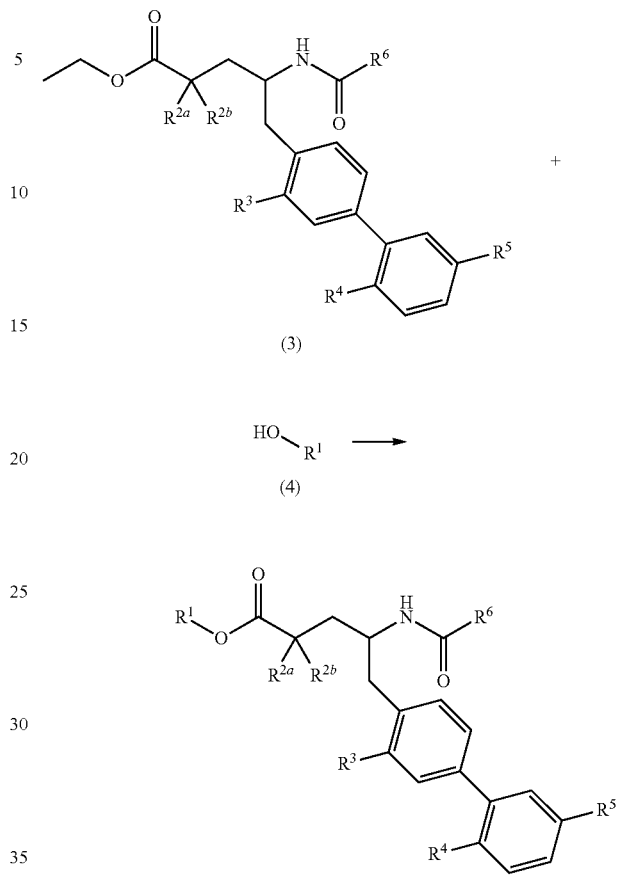

Scheme II is a transesterification reaction. Generally, this reaction involves reacting the ester compound of formula 3 ($R^{2a}$, $R^{2b}$, and $R^3$-$R^6$ are as defined for formula I) with the desired alcohol compound of formula 4 ($R^1$ is as defined for formula I) and a suitable acid catalyst, for example hydrochloric acid. Preparation of the compound of formula 3 from the acid (the compound of formula I) is known in the art or is described herein. The HO—$R^1$ alcohols are either commercially available or can be prepared by techniques that are known in the art or described herein. Exemplary HO—$R^1$ groups include:

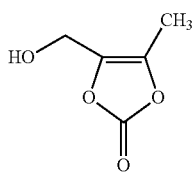

Certain intermediates described herein are believed to be novel and accordingly, such compounds are provided as further aspects of the invention including, for example, the compounds of formula 5 or a salt thereof:

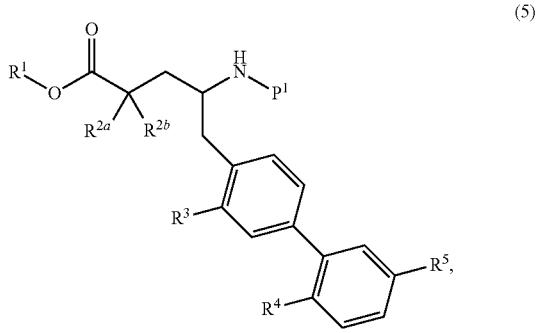

(5)

where $R^1$ and $R^3$-$R^5$ are as defined for formula I; $R^{2a}$ is —$C_{1-2}$alkyl and $R^{2b}$ is —$C_{0-2}$alkylene-NH$_2$, —C(O)NH$_2$, —COOH, —CN, or pyridine; or $R^{2a}$ is —CH$_2$OH and $R^{2b}$ is —CH$_2$CH$_3$, —(CH$_2$)$_2$CH$_3$, —C$_{1-2}$alkylene-OH, —(CH$_2$)$_2$NH$_2$, —(CH$_2$)$_2$—NHC(O)CH$_3$, or —CH$_2$CH=CH$_2$; or $R^{2a}$ and $R^{2b}$ are taken together to form —O—(CH$_2$)$_2$—, —(CH$_2$)$_2$—O—CH$_2$—, —CH$_2$—NH—CH$_2$—, —NH—(CH$_2$)$_2$—, —(CH$_2$)—NH—(CH$_2$)$_2$—, or —(CH$_2$)—N[C(O)CH$_3$]—(CH$_2$)$_2$—; and $P^1$ is H or an amino-protecting group selected from the group consisting of t-butoxycarbonyl, trityl, benzyloxycarbonyl, 9-fluorenylmethoxycarbonyl, formyl, trimethylsilyl, and t-butyldimethylsilyl; or a salt thereof.

Further details regarding specific reaction conditions and other procedures for preparing representative compounds of the invention or intermediates thereof are described in the Examples set forth below.

Utility

Compounds of the invention possess neprilysin (NEP) inhibition activity, that is, the compounds are able to inhibit enzyme-catalytic activity. In another embodiment, the compounds do not exhibit significant inhibitory activity of the angiotensin-converting enzyme. One measure of the ability of a compound to inhibit NEP activity is the inhibition constant (pK$_i$). The pK$_i$ value is the negative logarithm to base 10 of the dissociation constant (K$_i$), which is typically reported in molar units. Compounds of the invention of particular interest are those having a pK$_i$ at NEP greater than or equal to 7.0, and even more particularly those having a pK$_i$ greater than or equal to 8.0; and in still another embodiment, compounds of interest have a pK$_i$ in the range of greater than or equal to 9.0. Such values can be determined by techniques that are well known in the art, as well as in the assays described herein.

Another measure of the ability of a compound to inhibit NEP activity is the apparent inhibition constant (IC$_{50}$), which is the molar concentration of compound that results in half-maximal inhibition of substrate conversion by the NEP enzyme. The pIC$_{50}$ value is the negative logarithm to base 10 of the IC$_{50}$. Compounds of the invention that are of particular interest, include those that exhibit a pIC$_{50}$ for NEP greater than or equal to about 7.0. In another embodiment, compounds of interest have a pIC$_{50}$ for NEP within the range of about 7.0-10.0.

It is noted that in some cases, compounds of the invention may possess weak NEP inhibition activity. In such cases, those of skill in the art will recognize that these compounds still have utility as research tools.

Exemplary assays to determine properties of compounds of the invention, such as the NEP inhibiting activity, are described in the Examples and include by way of illustration and not limitation, assays that measure NEP inhibition (described in Assay 1). Useful secondary assays include assays to measure ACE inhibition (also described in Assay 1) and aminopeptidase P (APP) inhibition (described in Sulpizio et al. (2005) *JPET* 315:1306-1313). A pharmacodynamic assay to assess the in vivo inhibitory potencies for ACE and NEP in anesthetized rats is described in Assay 2 (see also Seymour et al. (1985) *Hypertension* 7(Suppl I):I-35-I-42 and Wigle et al. (1992) *Can. J. Physiol. Pharmacol.* 70:1525-1528), where ACE inhibition is measured as the percent inhibition of the angiotensin I pressor response and NEP inhibition is measured as increased urinary cyclic guanosine 3',5'-monophosphate (cGMP) output.

There are many in vivo assays that can be used to ascertain further utilities of the compounds of the invention. The conscious spontaneously hypertensive rat (SHR) model is a renin dependent hypertension model, and is described in Assay 3. See also Intengan et al. (1999) *Circulation* 100 (22):2267-2275 and Badyal et al. (2003) *Indian Journal of Pharmacology* 35:349-362. The conscious desoxycorticosterone acetate-salt (DOCA-salt) rat model is a volume dependent hypertension model that is useful for measuring NEP activity, and is described in Assay 4. See also Trapani et al. (1989) *J. Cardiovasc. Pharmacol.* 14:419-424, Intengan et al. (1999) *Hypertension* 34(4):907-913, and Badyal et al. (2003) supra). The DOCA-salt model is particularly useful for evaluating the ability of a test compound to reduce blood pressure as well as to measure a test compound's ability to prevent or delay a rise in blood pressure. The Dahl salt-sensitive (DSS) hypertensive rat model is a model of hypertension that is sensitive to dietary salt (NaCl), and is described in Assay 5. See also Rapp (1982) *Hypertension* 4:753-763. The rat monocrotaline model of pulmonary arterial hypertension described, for example, in Kato et al. (2008) *J. Cardiovasc. Pharmacol.* 51(1):18-23, is a reliable predictor of clinical efficacy for the treatment of pulmonary arterial hypertension. Heart failure animal models include the DSS rat model for heart failure and the aorto-caval fistula model (AV shunt), the latter of which is described, for example, in Norling et al. (1996) *J. Amer. Soc. Nephrol.* 7:1038-1044. Other animal models, such as the hot plate, tail-flick and formalin tests, can be used to measure the analgesic properties of compounds of the invention, as well as the spinal nerve ligation (SNL) model of neuropathic pain. See, for example, Malmberg et al. (1999) *Current Protocols in Neuroscience* 8.9.1-8.9.15. Other properties and utilities of the compounds can be demonstrated using various in vitro and in vivo assays well known to those skilled in the art.

Depending upon the intended route of administration, oral bioavailability may be an important characteristic, as well as potency as a neprilysin inhibitor. One means of measuring oral bioavailability is by the rat PO cassette assay, where the % F is a measure of the amount of the oral drug dose that actually gets into the blood stream; an exemplary assay is described in Assay 6. Compounds tested in this assay and having a % F<10% are likely to be poorly absorbed. Similarly, compounds tested in this assay and having a % F>10% are likely to be better absorbed. Therefore, compounds of the invention having a % F>10% are of particular interest as orally administered drugs.

Compounds of the invention are expected to inhibit the NEP enzyme in any of the assays listed above, or assays of a similar nature. Thus, the aforementioned assays are useful in determining the therapeutic utility of compounds of the invention, for example, their utility as antihypertensive agents or antidiarrheal agents. Other properties and utilities of compounds of the invention can be demonstrated using other in vitro and in vivo assays well-known to those skilled in the art. Compounds of formula I may be active drugs as well as prodrugs. Thus, when discussing the activity of compounds of the invention, it is understood that any such prodrugs may not exhibit the expected activity in an assay, but are expected to exhibit the desired activity once metabolized.

Compounds of the invention are expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of a compound of the invention. For example, by inhibiting NEP, the compounds are expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, these compounds are expected to have other physiological actions, for example, on the renal, central nervous, reproductive and gastrointestinal systems.

Cardiovascular Diseases

By potentiating the effects of vasoactive peptides like the natriuretic peptides and bradykinin, compounds of the invention are expected to find utility in treating and/or preventing medical conditions such as cardiovascular diseases. See, for example, Rogues et al. (1993) *Pharmacol. Rev.* 45:87-146 and Dempsey et al. (2009) *Amer. J. of Pathology* 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure. Thus, one embodiment of the invention relates to a method for treating hypertension, particularly primary hypertension or pulmonary arterial hypertension, comprising administering to a patient a therapeutically effective amount of a compound of the invention.

For treatment of primary hypertension, the therapeutically effective amount is typically the amount that is sufficient to lower the patient's blood pressure. This would include both mild-to-moderate hypertension and severe hypertension. When used to treat hypertension, the compound may be administered in combination with other therapeutic agents such as aldosterone antagonists, aldosterone synthase inhibitors, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $β_1$-adrenergic receptor antagonists, dual-acting β-adrenergic receptor antagonist/$α_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, a compound of the invention is combined with an $AT_1$ receptor antagonist, a calcium channel blocker, a diuretic, or a combination thereof, and used to treat primary hypertension. In another particular embodiment of the invention, a compound of the invention is combined with an $AT_1$ receptor antagonist, and used to treat hypertension with accompanying renal disease. When used to treat resistant hypertension, the compound may be administered in combination with other therapeutic agents such as aldosterone synthase inhibitors.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension the compound may be administered in combination with other therapeutic agents such as α-adrenergic receptor antagonists, $β_1$-adrenergic receptor antagonists, $β_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, a compound of the invention is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of a compound of the invention. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, the compound may be administered in combination with other therapeutic agents such as adenosine receptor antagonists, advanced glycation end product breakers, aldosterone antagonists, $AT_1$ receptor antagonists, $β_1$-adrenergic receptor antagonists, dual-acting β-adrenergic receptor antagonist/$α_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, a compound of the invention is combined with an aldosterone antagonist, a β$_1$-adrenergic receptor antagonist, an AT$_1$ receptor antagonist, or a diuretic, and used to treat congestive heart failure.

Diarrhea

As NEP inhibitors, compounds of the invention are expected to inhibit the degradation of endogenous enkephalins and thus such compounds may also find utility for the treatment of diarrhea, including infectious and secretory/watery diarrhea. See, for example, Baumer et al. (1992) *Gut* 33:753-758; Farthing (2006) *Digestive Diseases* 24:47-58; and Marøais-Collado (1987) *Eur. J. Pharmacol.* 144(2): 125-132. When used to treat diarrhea, compounds of the invention may be combined with one or more additional antidiarrheal agents.

Renal Diseases

By potentiating the effects of vasoactive peptides like the natriuretic peptides and bradykinin, compounds of the invention are expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases. Renal diseases of particular interest include diabetic nephropathy, chronic kidney disease, proteinuria, and particularly acute kidney injury (caused, for example, by cardiovascular surgery, chemotherapy, or the use of contrast dyes in medical imaging) or acute renal failure (see Sharkovska et al. (2011) *Clin. Lab.* 57:507-515 and Newaz et al. (2010) *Renal Failure* 32:384-390). When used to treat renal disease, the compound may be administered in combination with other therapeutic agents such as angiotensin-converting enzyme inhibitors, AT$_1$ receptor antagonists, and diuretics.

Preventative Therapy

By potentiating the effects of the natriuretic peptides, compounds of the invention are also expected to be useful in preventative therapy, due to the antihypertrophic and anti-fibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, compounds of the invention are expected to be useful to treat glaucoma. See, for example, Diestelhorst et al. (1989) *International Ophthalmology* 12:99-101. When used to treat glaucoma, compounds of the invention may be combined with one or more additional antiglaucoma agents.

Pain Relief

As NEP inhibitors, compounds of the invention are expected to inhibit the degradation of endogenous enkephalins and thus such compounds may also find utility as analgesics. See, for example, Rogues et al. (1980) *Nature* 288:286-288 and Thanawala et al. (2008) *Current Drug Targets* 9:887-894. When used to treat pain, the compounds of the invention may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, 5-HT$_{1D}$ serotonin receptor agonists, and tricyclic antidepressants.

Other Utilities

Due to their NEP inhibition properties, compounds of the invention are also expected to be useful as antitussive agents, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE-V inhibitors, dopamine agonists, estrogen receptor agonists and/or antagonists, androgens, and estrogens. Due to their NEP inhibition properties, compounds of the invention are also expected to have anti-inflammatory properties, and are expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to their NEP inhibition properties, compounds of the invention are also expected to be useful in providing protection from nerve impairment caused by diabetes or diet induced obesity.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Research Tools

Since compounds of the invention possess NEP enzyme inhibition activity, such compounds are also useful as research tools for investigating or studying biological systems or samples having a NEP enzyme, for example to study diseases where the NEP enzyme or its peptide substrates plays a role. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of a compound of the invention. Compounds of the invention can also be used as research tools by conducting biological assays using such compounds.

When used as a research tool, a biological system or sample comprising a NEP enzyme is typically contacted with a NEP enzyme-inhibiting amount of a compound of the invention. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., p.o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, compounds of the invention can be used as research tools for evaluating other chemical compounds, and thus are also useful in screening assays to discover, for example, new compounds having NEP-inhibiting activity. In this manner, a compound of the invention is used as a standard in an assay to allow comparison of the results obtained with a test compound and with compounds of the invention to identify those test compounds that have about equal or superior activity, if any. For example, $pK_i$ data for a test compound or a group of test compounds is compared to the $pK_i$ data for a compound of the invention to identify those test compounds that have the desired properties, for example, test compounds having a $pK_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay.

Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in Remington: The Science and Practice of Pharmacy, 20$^{th}$ Edition, Lippincott Williams & White, Baltimore, Md. (2000); and H. C. Ansel et al., Pharmaceutical Dosage Forms and Drug Delivery Systems, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

The compounds of the invention may be useful as the sole treatment of a disease or may be combined with one or more additional therapeutic agents in order to obtain the desired therapeutic effect. Thus, in one embodiment, pharmaceutical compositions of the invention contain other drugs that are co-administered with a compound of the invention. For example, the composition may further comprise one or more drugs (also referred to as "secondary agents(s)"). Such therapeutic agents are well known in the art, and include adenosine receptor antagonists, α-adrenergic receptor antagonists, $\beta_1$-adrenergic receptor antagonists, $\beta_2$-adrenergic receptor agonists, dual-acting β-adrenergic receptor antagonist/$\alpha_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). It is also contemplated that the secondary agent may be administered more than 24 hours after administration of the compound of the invention. Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, compounds of the invention are administered in combination with an adenosine receptor antagonist, representative examples of which include, but are not limited to, naxifylline, rolofylline, SLV-320, theophylline, and tonapofylline.

In one embodiment, compounds of the invention are administered in combination with an α-adrenergic receptor antagonist, representative examples of which include, but are not limited to, doxazosin, prazosin, tamsulosin, and terazosin.

Compounds of the invention may also be administered in combination with a $β_1$-adrenergic receptor antagonist ("$β_1$-blockers"). Representative $β_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $β_1$-antagonist is selected from atenolol, bisoprolol, metoprolol, propranolol, sotalol, and combinations thereof. Typically, the $β_1$-blocker will be administered in an amount sufficient to provide from about 2-900 mg per dose.

In one embodiment, compounds of the invention are administered in combination with a $β_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, vilanterol, and the like Typically, the $β_2$-adrenergic receptor agonist will be administered in an amount sufficient to provide from about 0.05-500 mg per dose.

In one embodiment, compounds of the invention are administered in combination with an advanced glycation end product (AGE) breaker, examples of which include, by way of illustration and not limitation, alagebrium (or ALT-711), and TRC4149.

In another embodiment, compounds of the invention are administered in combination with an aldosterone antagonist, representative examples of which include, but are not limited to, eplerenone, spironolactone, and combinations thereof. Typically, the aldosterone antagonist will be administered in an amount sufficient to provide from about 5-300 mg per day.

In one embodiment, compounds of the invention are administered in combination with an aminopeptidase N or dipeptidyl peptidase III inhibitor, examples of which include, by way of illustration and not limitation, bestatin and PC18 (2-amino-4-methylsulfonyl butane thiol, methionine thiol).

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof.

In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day. In another embodiment, compounds of the invention are administered in combination with a dual-acting angiotensin-converting enzyme/neprilysin (ACE/NEP) inhibitor, examples of which include, but are not limited to: AVE-0848 ((4S,7S,12bR)-7-[3-methyl-2(S)-sulfanylbutyramido]-6-oxo-1,2,3,4,6,7,8,12b-octahydro-pyrido[2,1-a][2]-benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentyl-carbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]

azepine-3-carboxylic acid); gempatrilat; MDL-101264 ((4S, 7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(5)-(mercaptomethyl)-3(R)-phenylbutyl]-L-alanine); sampatrilat; SA-898 ((2R,4R)—N-[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, compounds of the invention are administered in combination with an angiotensin-converting enzyme 2 (ACE2) activator or stimulator.

In one embodiment, compounds of the invention are administered in combination with an angiotensin-II vaccine, examples of which include, but are not limited to ATR12181 and CYT006-AngQb.

In one embodiment, compounds of the invention are administered in combination with an anticoagulant, representative examples of which include, but are not limited to: coumarins such as warfarin; heparin; and direct thrombin inhibitors such as argatroban, bivalirudin, dabigatran, and lepirudin.

In yet another embodiment, compounds of the invention are administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, compounds of the invention are administered in combination with antidiarrheal treatments. Representative treatment options include, but are not limited to, oral rehydration solutions (ORS), loperamide, diphenoxylate, and bismuth subsalicylate.

In yet another embodiment, a compound of the invention is administered in combination with an anti-glaucoma agent. Representative anti-glaucoma agents include, but are not limited to: α-adrenergic agonists such as brimonidine; $β_1$-adrenergic receptor antagonists; topical $β_1$-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, compounds of the invention are administered in combination with an anti-lipid agent. Representative anti-lipid agents include, but are not limited to: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, compounds of the invention are administered in combination with an anti-thrombotic agent. Representative anti-thrombotic agents include, but are not limited to: aspirin; anti-platelet agents such as clopidogrel, prasugrel, and ticlopidine; heparin; and combinations thereof.

In one embodiment, compounds of the invention are administered in combination with an $AT_1$ receptor antagonist, also known as angiotensin II type 1 receptor blockers (ARBs). Representative ARBs include, but are not limited to, abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoxomil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compounds of the invention may also be administered in combination with a dual-acting agent, such as an $AT_1$ receptor antagonist/neprilysin inhibitor (ARB/NEP) inhibitor, examples of which include, but are not limited to, compounds described in U.S. Publication Nos. 2008/0269305 and 2009/0023228, both to Allegretti et al. filed on Apr. 23, 2008, such as the compound, 4'-{2-ethoxy-4-ethyl-5-[(S)-2-mercapto-4-methylpentanoylamino)-methyl]imidazol-1-ylmethyl}-3'-fluorobiphenyl-2-carboxylic acid.

Compounds of the invention may also be administered in combination with multifunctional angiotensin receptor blockers as described in Kurtz & Klein (2009) *Hypertension Research* 32:826-834.

In one embodiment, compounds of the invention are administered in combination with a bradykinin receptor antagonist, for example, icatibant (HOE-140). It is expected that this combination therapy may present the advantage of preventing angioedema or other unwanted consequences of elevated bradykinin levels.

In one embodiment, compounds of the invention are administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, compounds of the invention are administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, compounds of the invention are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and Na$^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with an endothelin converting enzyme (ECE) inhibitor, examples of which include, but are not limited to, phosphoramidon, CGS 26303, and combinations thereof.

In a particular embodiment, compounds of the invention are administered in combination with an endothelin receptor antagonist. Representative endothelin receptor antagonists include, but are not limited to: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, tezosentan).

In yet another embodiment, a compound of the invention is administered in combination with one or more HMG-CoA reductase inhibitors, which are also known as statins. Representative statins include, but are not limited to, atorvastatin, fluvastatin, lovastatin, pitavastatin, pravastatin, rosuvastatin and simvastatin.

In one embodiment, compounds of the invention are administered in combination with a monoamine reuptake inhibitor, examples of which include, by way of illustration and not limitation, norepinephrine reuptake inhibitors such as atomoxetine, buprorion and the buprorion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine metabolite desmethyl norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, compounds of the invention are administered in combination with a muscle relaxant, examples of which include, but are not limited to: carisoprodol, chlorzoxazone, cyclobenzaprine, diflunisal, metaxalone, methocarbamol, and combinations thereof.

In one embodiment, compounds of the invention are administered in combination with a natriuretic peptide or analog, examples of which include but are not limited to: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, compounds of the invention are administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, compounds of the invention are administered in combination with a neprilysin (NEP) inhibitor. Representative NEP inhibitors include, but are not limited to: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 VS)-3-[3-(biphenyl-4-yl)-2-(phosphonomethylamino)propionamido]propionic acid); CGS-25155 (N-[9 (R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1(2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl) benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-(3-alanine); sialorphin; SCH-42495 (N-[2(S)-(acetylsulfanylmethyl)-3-(2-methylphenyl) propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-(3-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino] cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methyl-pentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl) ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, compounds of the invention are administered in combination with a nitric oxide donor, examples of which include, but are not limited to nicorandil; organic nitrates such as pentaerythritol tetranitrate; and sydnonimines such as linsidomine and molsidomine.

In yet another embodiment, compounds of the invention are administered in combination with a non-steroidal anti-inflammatory agent (NSAID). Representative NSAIDs include, but are not limited to: acemetacin, acetyl salicylic acid, alclofenac, alminoprofen, amfenac, amiprilose, aloxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, compounds of the invention are administered in combination with an N-methyl d-aspartate (NMDA) receptor antagonist, examples of which include, by way of illustration and not limitation, amantadine, dextromethorphan, dextropropoxyphene, ketamine, ketobemidone, memantine, methadone, and so forth.

In still another embodiment, compounds of the invention are administered in combination with an opioid receptor agonist (also referred to as opioid analgesics). Representative opioid receptor agonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, compounds of the invention are administered in combination with a phosphodiesterase (PDE) inhibitor, particularly a PDE-V inhibitor. Representative PDE-V inhibitors include, but are not limited to, avanafil, lodenafil, mirodenafil, sildenafil (Revatio®), tadalafil (Adcirca®), vardenafil (Levitra®), and udenafil.

In another embodiment, compounds of the invention are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, tafluprost, travoprost, and treprostinil, with bimatoprost, latanoprost, and tafluprost being of particular interest.

In yet another embodiment, compounds of the invention are administered in combination with a prostaglandin receptor agonist, examples of which include, but are not limited to, bimatoprost, latanoprost, travoprost, and so forth.

Compounds of the invention may also be administered in combination with a renin inhibitor, examples of which include, but are not limited to, aliskiren, enalkiren, remikiren, and combinations thereof.

In another embodiment, compounds of the invention are administered in combination with a selective serotonin reuptake inhibitor (SSRI). Representative SSRIs include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, compounds of the invention are administered in combination with a $5\text{-HT}_{1D}$ serotonin receptor agonist, examples of which include, by way of illustration and not limitation, triptans such as almotriptan, avitriptan, eletriptan, frovatriptan, naratriptan, rizatriptan, sumatriptan, and zolmitriptan.

In one embodiment, compounds of the invention are administered in combination with a sodium channel blocker, examples of which include, by way of illustration and not limitation, carbamazepine, fosphenytoin, lamotrigine, lidocaine, mexiletine, oxcarbazepine, phenytoin, and combinations thereof.

In one embodiment, compounds of the invention are administered in combination with a soluble guanylate cyclase stimulator or activator, examples of which include, but are not limited to ataciguat, riociguat, and combinations thereof.

In one embodiment, compounds of the invention are administered in combination with a tricyclic antidepressant (TCA), examples of which include, by way of illustration and not limitation, amitriptyline, amitriptylinoxide, butriptyline, clomipramine, demexiptiline, desipramine, dibenzepin, dimetacrine, dosulepin, doxepin, imipramine, impraminoxide, lofepramine, melitracen, metapramine, nitroxazepine, nortriptyline, noxiptiline, pipofezine, propizepine, protriptyline, quinupramine, and combinations thereof.

In one embodiment, compounds of the invention are administered in combination with a vasopressin receptor antagonist, examples of which include, by way of illustration and not limitation, conivaptan and tolvaptan.

Combined secondary therapeutic agents may also be helpful in further combination therapy with compounds of the invention. For example, compounds of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules For Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, a compound of the invention (30 g), a secondary agent (20 g), 440 g spray-dried lactose and 10 g magnesium stearate are thoroughly blended, and processed as described above.

Exemplary Gelatin Capsule Formulation For Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule). Alternately, a compound of the invention (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation For Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation For Oral Administration

The following ingredients are mixed to form a suspension containing 100 mg of the compound of the invention per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation For Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Injectable Formulation For Administration By Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions For Administration By Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

AcOH acetic acid
BOC t-butoxycarbonyl (—C(O)OC(CH$_3$)$_3$)
(BOC)$_2$O di-t-butyl dicarbonate
Bn benzyl
CDI N,N''-carbonyldiimidazole
CPME cyclopentyl methyl ether
DBU 1,8-diazabicyclo[5.4.0]undec-7-ene
DCC 1,3-dicyclohexylcarbodiimide
DCM dichloromethane or methylene chloride
DIAD diisopropyl azodicarboxylate
DIPE diisopropyl ether
DIPEA N,N-diisopropylethylamine
DMAP 4-dimethylaminopyridine
DMF N,N-dimethylformamide
EDC 1-(3-dimethylaminopropyl)-3-ethylcarbodiimide
EDTA ethylenediaminetetraacetic acid
Et$_3$N triethylamine
EtOH ethanol
Et$_2$O diethyl ether
EtOAc ethyl acetate
HATU N,N,N'',N'-tetramethyl-O-(7-azabenzotriazol-1-yl)uronium hexafluorophosphate
HOBt 1-hydroxybenzotriazole
MeCN acetonitrile
MeOH methanol
NaHMDS sodium bis(trimethylsilyl)amide
Pd/C palladium on carbon
Pd(dppf)$_2$Cl$_2$ 1,1-bis(diphenylphosphino)ferrocene palladium chloride
Pd(PPh$_3$)$_4$ tetrakis(triphenylphosphine)palladium(0)
PE petroleum ether
PPh$_3$ triphenylphosphine
TFA trifluoroacetic acid
THF tetrahydrofuran Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Generally, solvents used in analytical HPLC were as follows: solvent A was 98% H$_2$O/2% MeCN/1.0 mL/L TFA; solvent B was 90% MeCN/10% H$_2$O/1.0 mL/L TFA.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

It is understood that many of the compounds described in the Preparations and Examples can exist in a tautomer form, and that both forms are intended to be covered. For example, (2R,4R)-2-amino-5-(5'-chloro-2'-fluorobiphenyl-4-yl)-2-methyl-4-[(3H-[1,2,3]triazole-4-carbonyl)amino]pentanoic acid and (2S,4R)-2-amino-5-(5'-chloro-2'-fluorobiphenyl-4-yl)-2-methyl-4-[(3H-[1,2,3]triazole-4-carbonyl)amino]pentanoic acid are depicted in Example 1 (isomers a and b) but it is understood that these compounds can exist in a tautomer form, for example, as (2R,4R)-2-amino-5-(5'-chloro-2'-fluorobiphenyl-4-yl)-2-methyl-4-[(1H-[1,2,3]triazole-4-carbonyl)amino]pentanoic acid and (2S,4R)-2-amino-5-(5'-chloro-2'-fluorobiphenyl-4-yl)-2-methyl-4-[(1H-[1,2,3] triazole-4-carbonyl)amino]pentanoic acid.

Preparation 1: (3S,5R)-5-(5'-Chloro-2'-fluorobiphenyl-4-ylmethyl)-3-hydroxymethyl-3-methylpyrrolidin-2-one

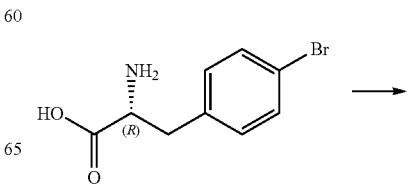

-continued

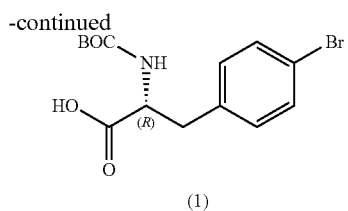

(1)

A solution of (R)-2-Amino-3-(4-bromophenyl)propionic acid (3300 g, 13.5 mol, 1.0 eq.) in MeCN (46.2 L) was charged into a reaction flask that had been purged and maintained with an inert atmosphere of nitrogen. A solution of NaOH (1081 g, 27.0 mol, 2.0 eq.) in water (46.2 L) was added in several batches at −10° C. To this was added a solution of di-t-butyl dicarbonate (2948 g, 13.51 mol, 1.0 eq.) in MeCN (6.6 L). The resulting solution was stirred overnight at room temperature, then concentrated in vacuo. The resulting solution was diluted with 45 L of water/ice. The solution pH was adjusted to 2 with HCl (1 mol/L). The resulting solution was extracted with DCM (3×50 L) and the organic layers combined. The resulting mixture was washed with saturated aqueous NaCl (50 L), then dried over $MgSO_4$ and concentrated in vacuo to yield Compound 1 (3720 g) as a white solid.

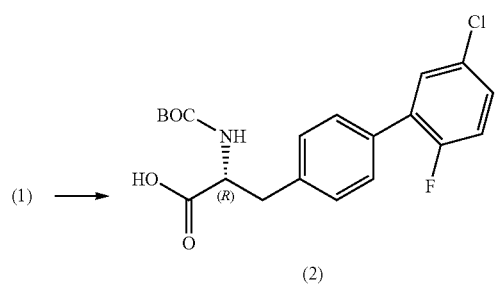

(1) →

(2)

A solution of Compound 1 (530 g, 1.54 mol, 1.0 eq.) in dioxane (9.54 L) was combined with (5-chloro-2-fluorophenyl)boronic acid (348 g, 2.0 mol, 1.3 eq.), a solution of $Na_2CO_3$ (228 g, 2.2 mol, 1.4 eq.) in water (1.1 L), and $Pd(PPh_3)_4$ (8.9 g, 7.7 mmol, 0.01 eq.) in a reaction flask that had been purged and maintained with an inert atmosphere of nitrogen. The resulting solution was heated to reflux for 2.5 hours in an oil bath, then cooled to room temperature with a water/ice bath. The resulting solution was diluted with EtOAc (15 L), washed with 1N HCl (5 L) and saturated aqueous NaCl (4×5 L). The combined organics were then dried over $MgSO_4$ and concentrated in vacuo. The residue was washed then with PE (2×1 L) to yield Compound 2 (510 g) as a brown oil.

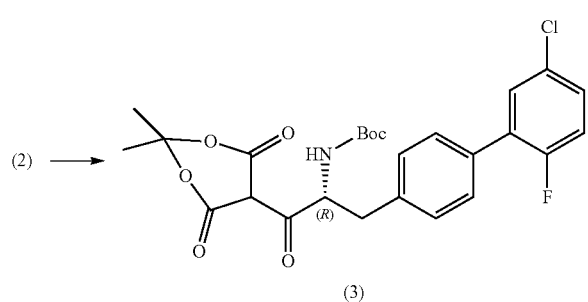

(2) →

(3)

A solution of Compound 2 (510 g, 1.3 mol, 1.0 eq.) in DCM (5 L) was combined with 2,2-dimethyl-1,3-dioxane-4,6-dione (205 g, 1.4 mol, 1.1 eq.) and 4-dimethylaminopyridine (237 g, 1.9 mol, 1.5 eq.) in a reaction flask that had been purged and maintained with an inert atmosphere of nitrogen. A solution of DCC (294 g, 1.4 mol, 1.1 eq.) in DCM (600 mL) was added dropwise with stirring at −10° C. The resulting solution was stirred overnight at room temperature. The solids were filtered, and the filtrate was washed with 1 N HCl (2 L) and saturated aqueous NaCl (3 L). The combined organics were dried over $MgSO_4$. The solids were filtered, to yield Compound 3 as the filtrate, which was used directly in the next step without further purification.

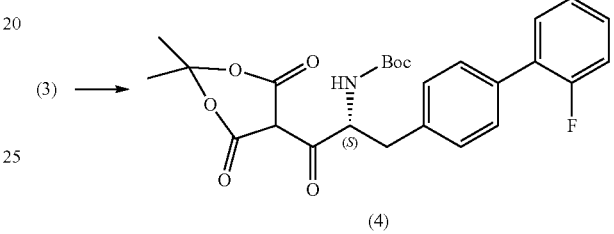

(3) →

(4)

A solution of Compound 3 in DCM (7 L, crude) was combined with AcOH (600 mL) in a reaction flask that had been purged and maintained with an inert atmosphere of nitrogen. $NaBH_4$ (88.8 g, 2.4 mol, 1.8 eq.) was added in several batches at −5° C. The resulting solution was stirred for 3 hours at −5° C. The reaction was then quenched by the dropwise addition of saturated aqueous NaCl (1 L). The resulting solution was diluted with saturated aqueous NaCl (2 L) and the resulting mixture was washed with water (2×2 L), $NaHCO_3$ (1 L), and saturated aqueous NaCl (2 L). The combined organics were dried over $MgSO_4$ and concentrated in vacuo to yield Compound 4 (520 g) as a yellow oil.

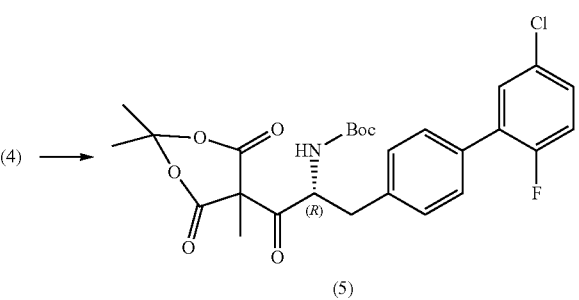

(4) →

(5)

A solution of Compound 4 (520 g, 1.0 mol, 1.0 eq.) in acetone/DMF (1:1) (5.2 L) was combined with $Na_2CO_3$ (163 g, 1.5 mol, 1.5 eq.) and methyl iodide (219 g, 1.5 mol, 1.5 eq.) in a reaction flask that had been purged and maintained with an inert atmosphere of nitrogen. The resulting solution was stirred overnight at room temperature, then diluted with water (15 L). After stirring for 1 hour the solids were collected by filtration. The residue was dissolved in DCM (5 L). The combined organics were dried over $MgSO_4$ and concentrated in vacuo to yield Compound 5 (520 g) as a yellow solid.

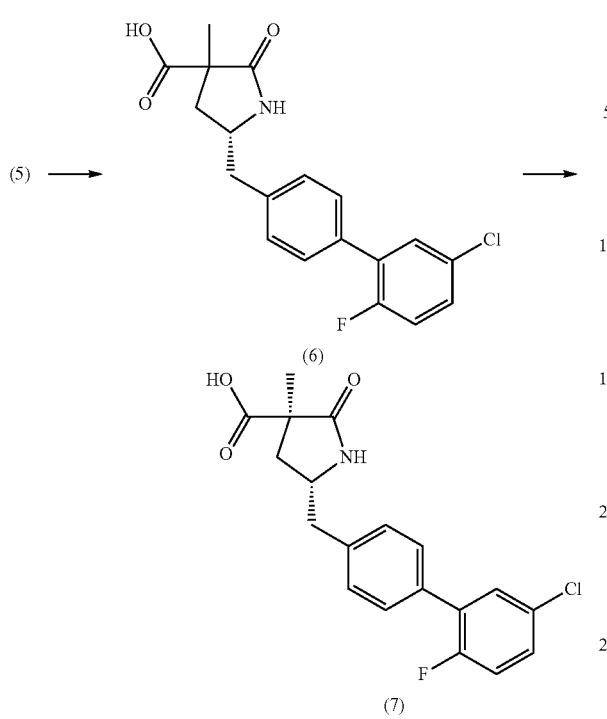

A solution of Compound 7 (218 g, 602.5 mmol, 1.0 eq.) in THF (4 L) and N-methylmorpholine (170 g, 1.7 mol, 2.8 eq.) was placed in a reaction flask that had been purged and maintained with an inert atmosphere of nitrogen. 2-methylpropyl chloroformate (164.4 g, 1.2 mol, 2.0 eq.) was added dropwise with stirring at −5° C. The resulting solution was stirred for 20 minutes at −5° C. A solution of NaBH$_4$ (91.5 g, 2.4 mol, 4.0 eq.) in water (400 mL) was then added dropwise with stirring at −5° C. The resulting solution was stirred for an additional 1 hour at room temperature. The reaction was then quenched by the dropwise addition of 1N HCl (2.6 L), and the resulting mixture was stirred for 1 hour and then concentrated in vacuo. The residual mixture was then stirred for another 1 hour, and then the solids were collected by filtration. The solids were washed with water, dissolved in THF, dried over Na$_2$SO$_4$, and concentrated in vacuo to yield the title compound (170 g) as a white solid.

Preparation 2: (2S,4R)-4-Amino-2-(benzyloxycarbonylaminomethyl)-5-(5'-chloro-2'-fluorobiphenyl-4-yl)-2-methylpentanoic Acid A solution of Compound 5 (520 g, 1.0 mol, 1.0 eq.) in CPME (2.6 L) was placed in a reaction flask that had been purged and maintained with an inert atmosphere of nitrogen. A 4N solution of HCl in CPME (2.6 L) was added at −5° C. The resulting solution was stirred overnight at room temperature, then concentrated to half of the volume in vacuo (yielding Compound 6). The solids were collected by filtration, then washed with a 1:2 mixture of EtOAc and DIPE to yield Compound 7 (220 g) as an off-white solid.

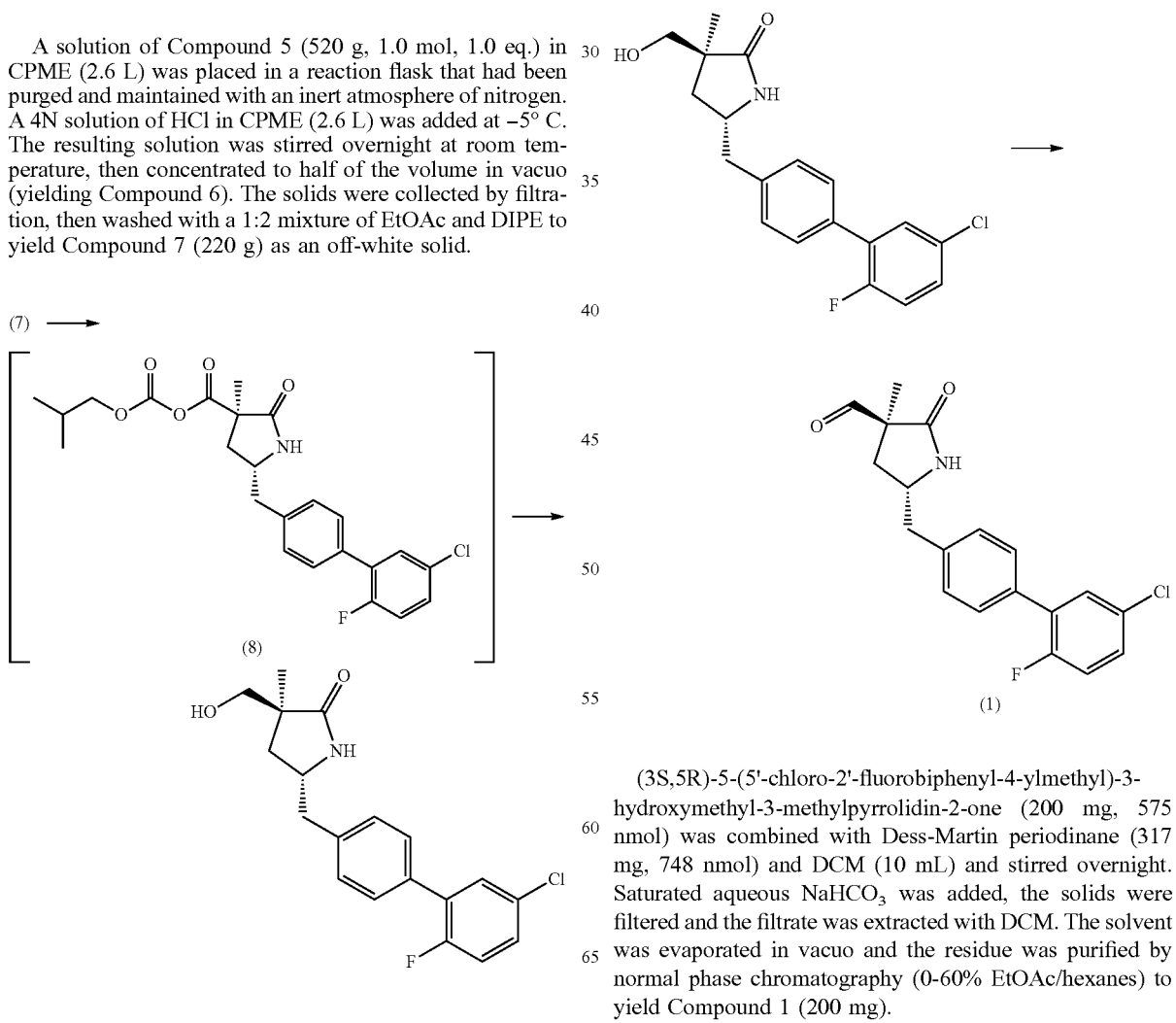

(3S,5R)-5-(5'-chloro-2'-fluorobiphenyl-4-ylmethyl)-3-hydroxymethyl-3-methylpyrrolidin-2-one (200 mg, 575 nmol) was combined with Dess-Martin periodinane (317 mg, 748 nmol) and DCM (10 mL) and stirred overnight. Saturated aqueous NaHCO$_3$ was added, the solids were filtered and the filtrate was extracted with DCM. The solvent was evaporated in vacuo and the residue was purified by normal phase chromatography (0-60% EtOAc/hexanes) to yield Compound 1 (200 mg).

(1) →

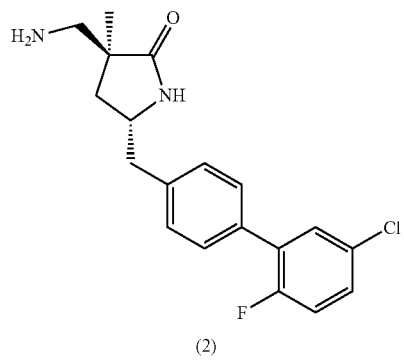

(2)

To a solution of Compound 1 (200 mg, 578 nmol) in MeOH (15 mL) was added ammonium acetate (446 mg, 5.8 mmol) and the solution was stirred at 60° C. for 2 hours. The mixture was cooled to 0° C. and sodium cyanoborohydride (58.2 mg, 925 nmol) was added, and stirred overnight. The reaction was quenched with saturated aqueous NH₄OH and extracted with DCM (30 mL). The organic extract was concentrated in vacuo and the residue was purified by reverse phase chromatography to yield Compound 2 (90 mg, 45% yield over 2 steps).

(2) →

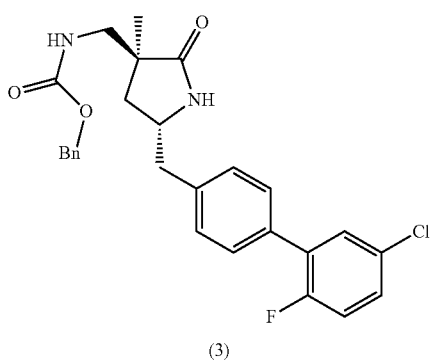

(3)

Compound 2 (90 mg, 259 nmol) in DCM (3 mL) was combined with benzyl chloroformate (44.5 µL, 311 nmol) followed by Et₃N (109 µL, 778 nmol). The mixture was stirred for 10 minutes and purified by normal phase chromatography (0-60% EtOAc/hexanes) to yield Compound 3 (15 mg, 12% yield) as the major product.

(3) →

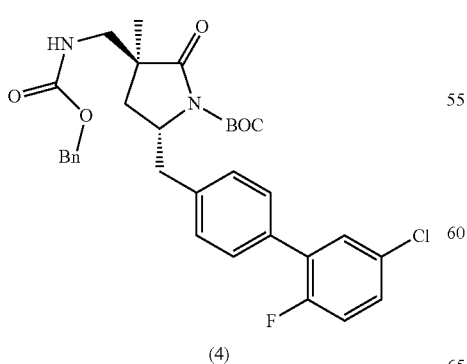

(4)

Compound 3 (15 mg, 31 nmol) was dissolved in THF (3 mL). Air was removed from the reaction flask, which was then purged with nitrogen. The solution was cooled to 0° C. and sodium bis(trimethylsilyl) amide (1.1 eq.) was added. The mixture was stirred for 10 minutes from 0° C. to room temperature, and then (BOC)₂O (8.0 µL, 34 µmol) was added. The mixture was stirred for 15 minutes to yield Compound 4, which was used directly in the next step.

(4) →

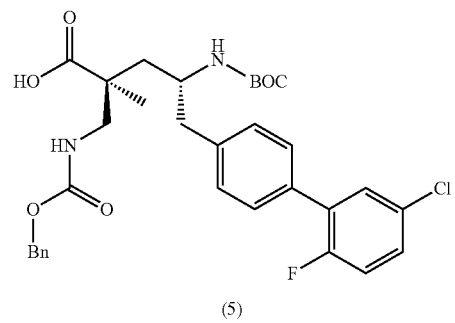

(5)

Crude Compound 4 was dissolved in NaOH (12.4 µL, 186 µmol), water (10 mL), and THF (10 mL) and the mixture was stirred for 5 hours. EtOAc (25 mL) was added and concentrated HCl was added until the solution was at pH 5. The organic layers were extracted, dried over MgSO₄, filtered and evaporated to dryness. The product was purified by normal phase chromatography (50-100% EtOAc/hexanes) to yield Compound 5 (14 mg, 75% yield over 2 steps).

(5) →

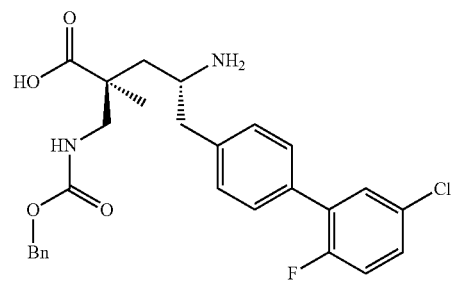

Compound 5 (14 mg, 23 µmol) was dissolved in MeCN (1 mL) and 4N HCl in dioxane (0.4 mL) and stirred for 20 minutes. The solvent was evaporated to yield the title compound (11 mg) as an HCl salt, which was used without further purification.

Preparation 3: (2S,4R)-4-t-Butoxycarbonylamino-5-(5'-chloro-2'-fluoro-biphenyl-4-yl)-2-diallylaminomethyl-2-methylpentanoic Acid Allyl Ester

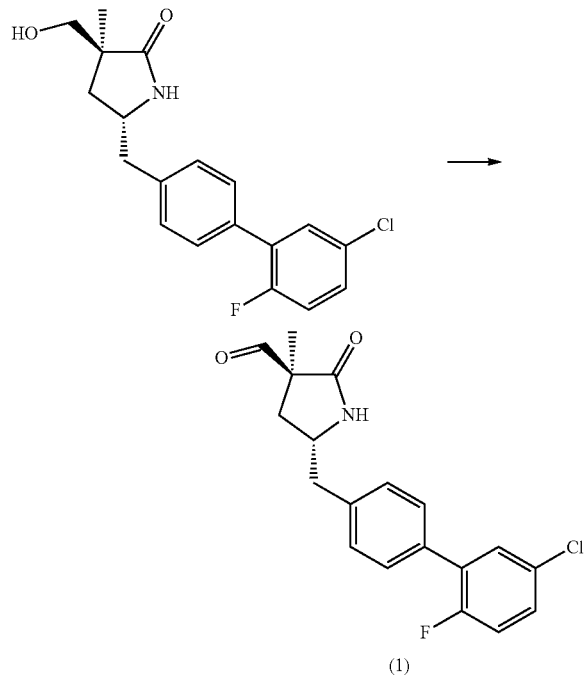

To a solution of (3S,5R)-5-(5'-chloro-2'-fluorobiphenyl-4-ylmethyl)-3-hydroxymethyl-3-methylpyrrolidin-2-one (2.0 g, 5.8 mmol) in DCM (100 mL) was added Dess-Martin periodinane (3.3 g, 7.5 mmol) and the solution was stirred at room temperature for 1.5 hours. The mixture was then washed with 1M NaOH (2×50 mL), water (50 mL) and saturated aqueous NaCl (50 mL). The combined organic layers were dried over $Na_2SO_4$, filtered, and concentrated in vacuo. The residue was purified by normal phase chromatography (0-60% EtOAc in hexanes) to yield Compound 1 (0.64 g, 32% yield) as a white foam.

(1) →

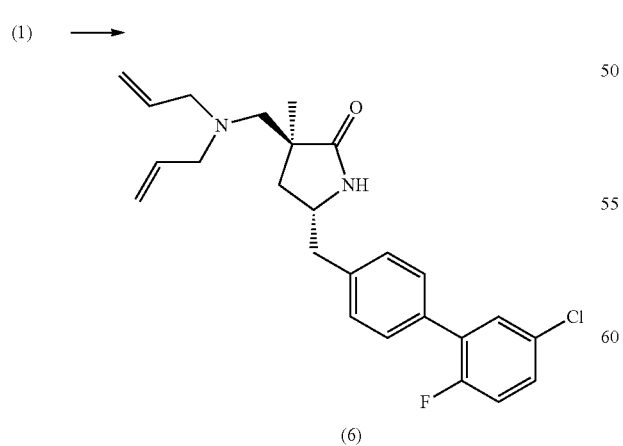

To a solution of Compound 1 (90.5 mg, 262 μmol) in DCM (920 μL) and MeOH (460 μL) was added AcOH (460 μL). Diallylamine (99%; CAS#124-02-7; 161 μL, 1.3 mmol) was added and the solution was stirred at room temperature for 1 hour. Sodium cyanoborohydride (99 mg, 1.60 mmol) was added and the solution was heated to 40° C. and stirred at this temperature overnight. The mixture was then concentrated in vacuo and the residue was purified by reverse phase column chromatography. The desired fractions were combined and lyophilized to yield Compound 6 (25 mg, 22% yield).

(6) →

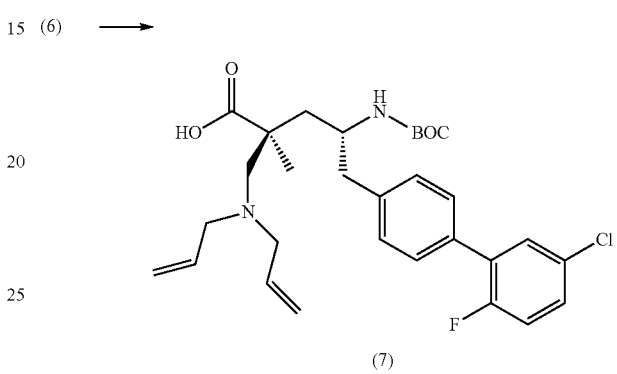

A solution of Compound 6 (25 mg, 59 μmol) in THF (6.0 mL) was cooled to 0° C., and NaHMDS (64 μL, 64 μmol) was added. After stirring at this temperature for 10 minutes, $(BOC)_2O$ (15 μL, 64 μmol) was added. The solution was warmed to room temperature and stirred for 3 hours. After this time, full conversion was observed by LC/MS. Water (6.0 mL) was added to the solution, followed by NaOH (23 μL, 351 μmol). The product was purified by reverse phase column chromatography (30-90%; 15 mL) and the desired fractions were combined and lyophilized to yield Compound 7 (14.5 mg, 45% yield).

(7) →

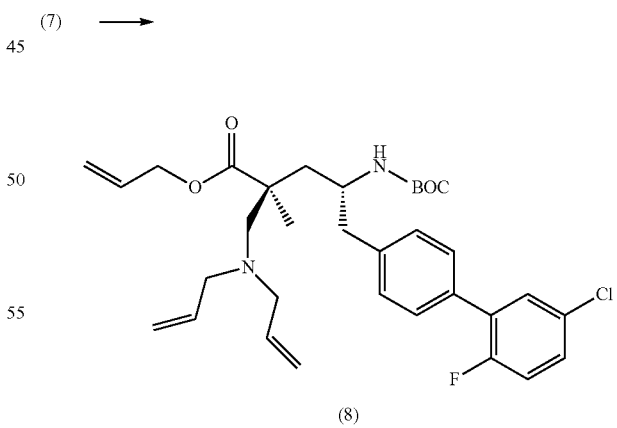

A solution of Compound 7 (14.5 mg, 27 nmol) and $K_2CO_3$ (4.0 mg, 29 μmol) in DMF (270 μL) was cooled to 0° C. and allyl bromide (2.5 μL, 29 μmol) was added. The solution was warmed to room temperature and stirred at this temperature overnight. The solution was concentrated to yield the title compound, which was used without further purification.

Preparation 4: (2S,4R)-4-Amino-2-carbamoyl-5-(5'-chloro-2'-fluorobiphenyl-4-yl)-2-methylpentanoic Acid

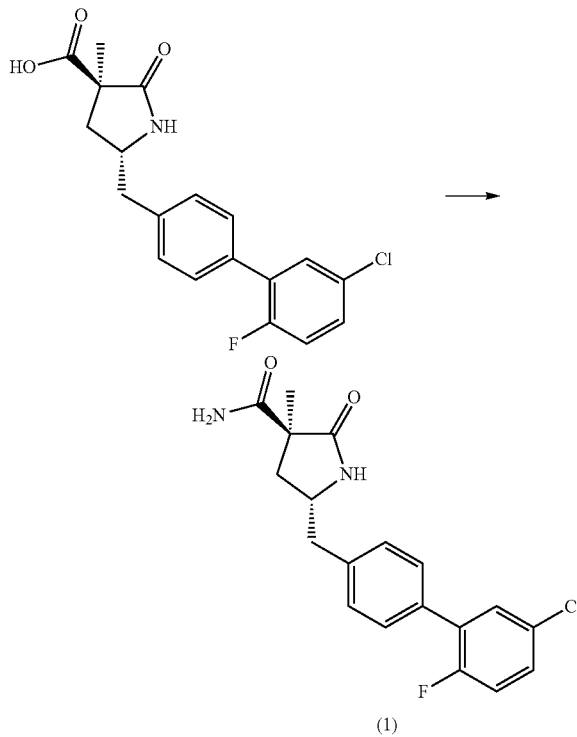

(1)

(3R,5R)-5-(5'-Chloro-2'-fluorobiphenyl-4-ylmethyl)-3-methyl-2-oxopyrrolidine-3-carboxylic acid (60 mg, 166 nmol) and HATU (69.4 mg, 182 nmol) were dissolved in DMF (3 mL) and stirred at room temperature for 20 minutes. A 0.5 M solution of ammonia in dioxane (1.2 eq.) and DIPEA (87 μL, 498 μmol) were then added. The mixture was stirred at room temperature for 15 minutes, at which time LCMS indicated the mass of the desired compound. The mixture was then concentrated in vacuo and the residue was purified by reverse phase chromatography to yield Compound 1 (50 mg, 84% yield).

(1) →

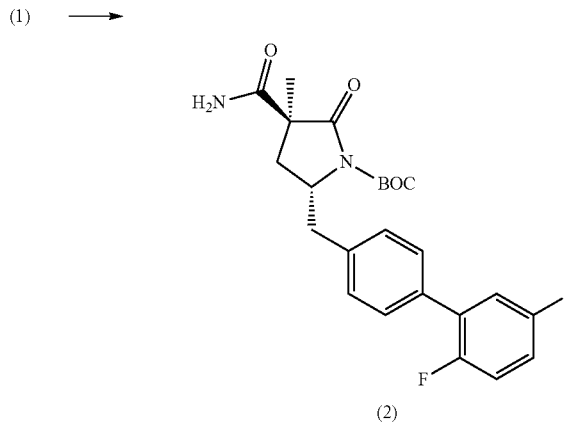

(2)

Compound 1 (50 mg, 139 μmol) was dissolved in THF (6 mL). Air was removed from the reaction flask, which was then purged with nitrogen. The solution was cooled to 0° C. and sodium bis(trimethylsilyl) amide (443 μL, 443 μmol) was added. The mixture was stirred for 10 minutes from 0° C. to room temperature. (BOC)$_2$O (103 mL, 443 μmol) was then added and the mixture was stirred for 1 hour at room temperature, at which time LCMS indicated the mass of the desired compound, yielding Compound 2 (63.9 mg) as an HCl salt, which was used directly in the next step without purification.

(2) →

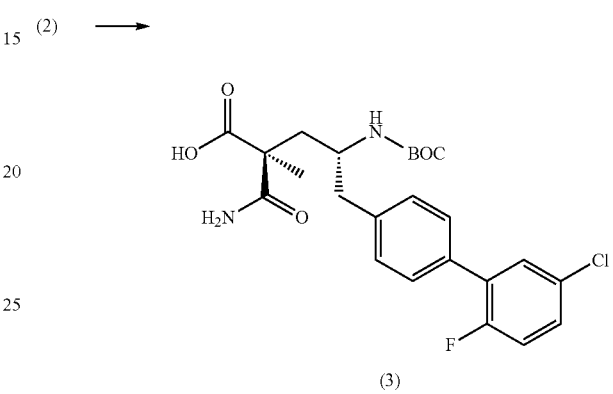

(3)

Crude Compound 2 (63.9 mg, 139 μmol) was dissolved in an aqueous solution of 10N NaOH to reach pH~12. The mixture was stirred at room temperature overnight, at which time LCMS indicated the mass of the desired compound. The mixture was then concentrated in vacuo. EtOAc was added followed by the addition of an aqueous solution of 1N HCl to reach pH 5. The organic layer was extracted, dried over MgSO$_4$, filtered and evaporated. The residue was purified by normal phase column chromatography to yield Compound 3 (32 mg, 48% yield).

(3) →

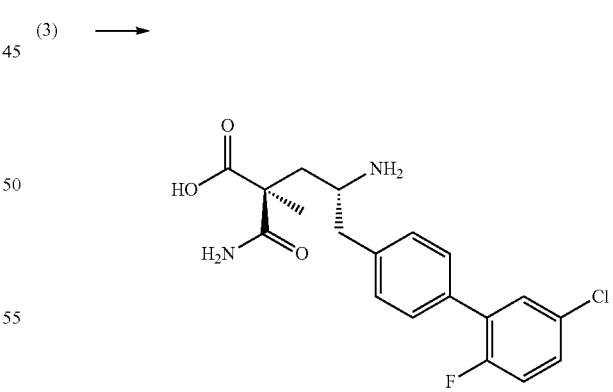

Compound 3 (32 mg, 0.1 mmol) was dissolved in MeCN (3 mL). A solution of 4N HCl in dioxane (250 μL, 1.0 mmol) was added, and the mixture was stirred at room temperature for 10 minutes, at which time LCMS indicated the mass of the desired compound. The mixture was concentrated in vacuo to yield the title compound as an HCl salt, which was used without purification.

Preparation 5: 2-[(R)-2-Amino-3-(5'-chloro-2'-fluorobiphenyl-4-yl)propyl]-2-methylmalonic Acid

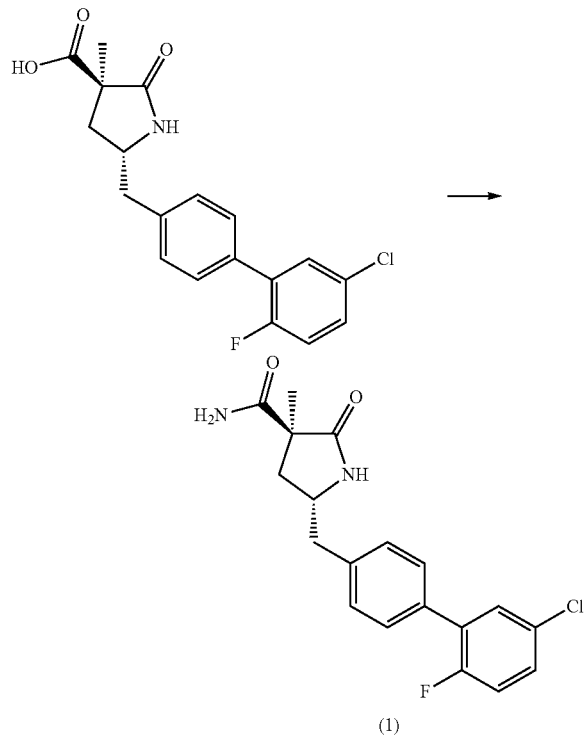

(3R,5R)-5-(5'-Chloro-2'-fluorobiphenyl-4-ylmethyl)-3-methyl-2-oxopyrrolidine-3-carboxylic acid (600 mg, 1.7 mmol) and HATU (694 mg, 1.8 mmol) were dissolved in DMF (3 mL) and stirred at room temperature for 20 minutes. A 0.5 M solution of ammonia in dioxane (4 mL, 2.0 mmol) and DIPEA (869 µL, 5.0 mmol) were then added, and the mixture was stirred at room temperature for 45 minutes, at which time LCMS indicated the mass of the desired compound. The mixture was concentrated in vacuo and the residue was purified by reverse phase chromatography to yield Compound 1 (365 mg, 61% yield).

(1) ⟶

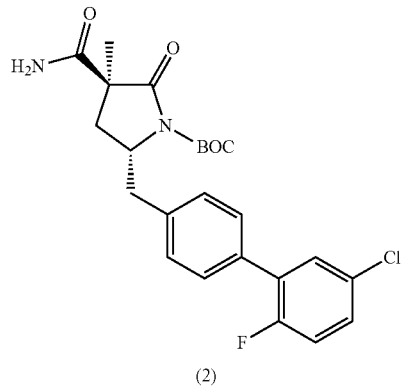

Compound 1 (365 mg, 1.0 mmol) was dissolved in THF (6 mL). Air was removed from the reaction flask, which was then purged with nitrogen. The solution was cooled to 0° C. and sodium bis(trimethylsilyl) amide (2.2 mL, 2.2 mmol) was then added. The mixture was stirred for 10 minutes from 0° C. to room temperature. (BOC)₂O (517 µL, 2.2 mmol) was then added and the mixture was stirred for 1 hour at room temperature, at which time LCMS indicated the mass of the desired compound, yielding Compound 2 as an HCl salt, which was used directly in the next step without purification.

(2) ⟶

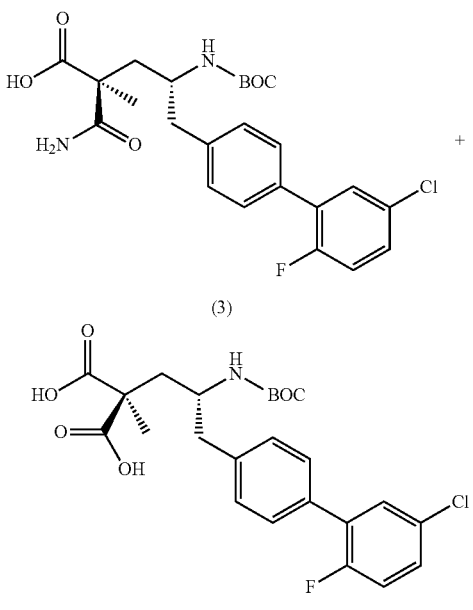

Crude Compound 2 (466 mg, 1.0 mmol) was dissolved in an aqueous solution of 10N NaOH (809 µL, 8.1 mmol) to reach pH~12. The mixture was stirred at room temperature overnight. LC/MS indicated the mass of Compounds 3 and 4 in ~50:50 ratio. The mixture was concentrated in vacuo. EtOAc was added followed by the addition of an aqueous solution of 1N HCl to reach pH 4-5. The organic layer was separated, dried over MgSO₄, filtered and evaporated. The residue was purified by normal phase column chromatography to yield Compound 3 (100 mg, 20% yield) and Compound 4 (329 mg, 68% yield).

(4) ⟶

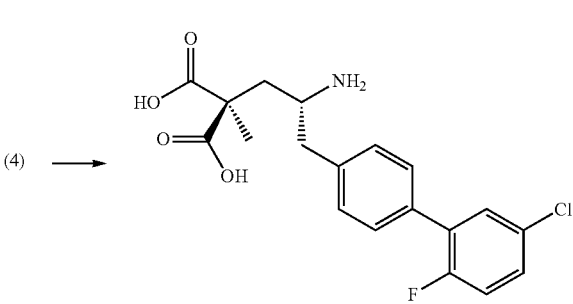

Compound 4 (15 mg, 31 µmol) was dissolved in MeCN (1.5 mL). A solution of 4N HCl in dioxane (117 µL, 469 µmol) was added, and the mixture was stirred at room temperature for 10 minutes, at which time LCMS indicated the mass of the desired compound. The mixture was concentrated in vacuo to yield the title compound as an HCl salt, which was used without further purification.

Preparation 6:
5-Oxo-4,5-dihydro-[1,2,4]oxadiazole-3-carboxylic Acid

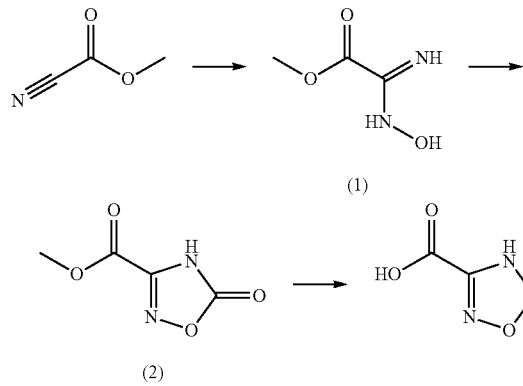

To a solution of nitriloacetic acid methyl ester (9 g, 106 mmol) in MeOH (100 mL) and water (100 ml), was added $NH_2OH \cdot HCl$ (11 g, 159 mmol) and $Na_2CO_3$ (11 g, 106 mmol). The mixture was stirred at room temperature for 2 hours. The organic solvent was removed in vacuo and the aqueous layer was extracted with DCM (8×100 mL). The combined organic layers were dried over $MgSO_4$, filtered, and concentrated to yield Compound 1 (5.7 g) as a white solid. LC-MS: $[M+H]^+$:119.

CDI (9.4 g, 58 mmol) and DBU (8.7 g, 58 mmol) were added to a solution of Compound 1 (5.7 g, 48 mmol) in 1,4-dioxane (50 mL), and the resulting mixture was stirred at 80° C. for 2 hours. The reaction was quenched with HCl, concentrated and extracted with DCM (8×100 mL). The combined organic layers were concentrated and purified by normal phase column chromatography (DCM:MeOH=80:1) to yield Compound 2 (3 g) as a yellow oil. LC-MS: $[M+H]^+$: 145.

LiOH (0.5 g, 20.8 mmol) was added to a solution of Compound 2 (3 g, 20.8 mmol) in water (30 mL), and the resulting mixture was stirred at room temperature for 3 hours. The mixture was washed with EtOAc (2×20 mL) and then acidified to pH=3 with 1M HCl, and concentrated. The residue was then recrystallized from AcOH to yield the title compound (2 g) as a white solid. LC-MS: $[M+H]^+$: 131.

Preparation 7: (2S,4R)-4-t-Butoxycarbonylamino-5-(5'-chloro-2'-fluorobiphenyl-4-yl)-2-hydroxymethyl-2-methylpentanoic Acid Ethyl Ester

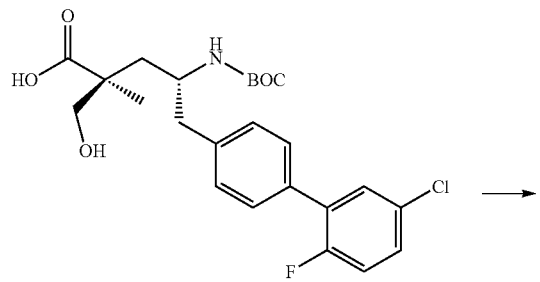

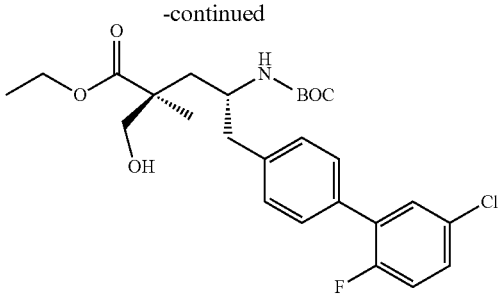

(2S,4R)-5-(5'-Chloro-2'-fluorobiphenyl-4-yl)-2-hydroxymethyl-2-methyl-4-methylamino-pentanoic acid (1.0 g, 2.2 mmol) was combined with HOBt (1.0 g, 6.7 mmol), EDC (1.5 mL, 6.7 mmol) and EtOH (5.2 mL, 89 mmol) and stirred at room temperature for 10 minutes. 4-Methylmorpholine (982 µL, 8.9 mmol) was added and the solution was stirred overnight. The solvent was removed in vacuo and the residue was purified by normal phase column chromatography (0-60% EtOAc/hexanes) to yield the title compound (380 mg, 35% yield).

Preparation 8: (2S,4R)-4-Amino-5-(5'-chloro-2'-fluorobiphenyl-4-yl)-2-methoxymethyl-2-methyl-pentanoic Acid Ethyl Ester

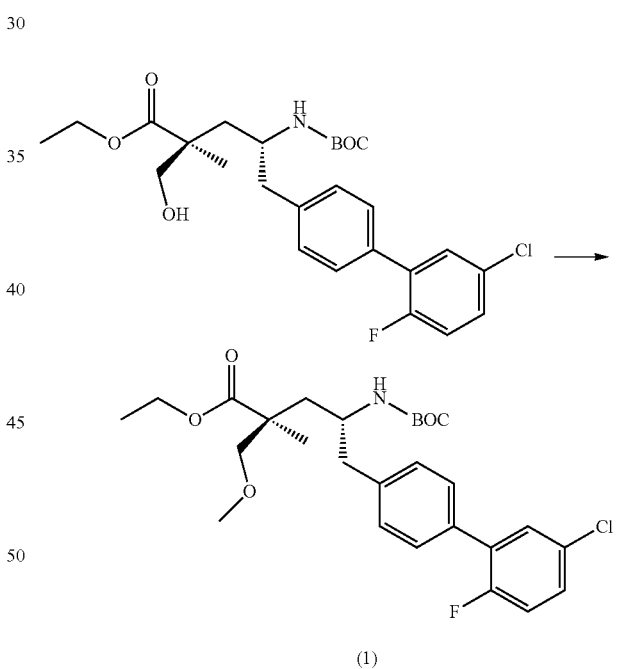

(2S,4R)-4-t-Butoxycarbonylamino-5-(5'-chloro-2'-fluorobiphenyl-4-yl)-2-hydroxymethyl-2-methylpentanoic acid ethyl ester (415 mg, 840 µmol) and tetrabutylammonium hydrogen sulfate (57 mg, 168 µmol) were dissolved in DCM (3 mL) and 10N NaOH (588 µL, 5.9 mmol). Dimethyl sulfate (424 mg, 3.4 mmol) was added and the reaction flask was sealed and stirred vigorously overnight. The mixture was extracted with DCM and water, purified by normal phase column chromatography (0-60 EtOAc:hexanes), and concentrated under reduced pressure to yield Compound 1 (220 mg, 52% yield).

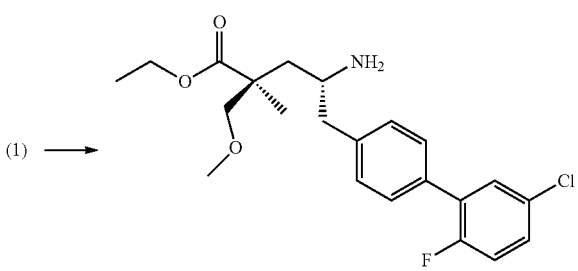 [SMILES: CCOC(=O)[C@](C)(COC)C[C@H](N)Cc1ccc(-c2cc(Cl)ccc2F)cc1]

Compound 1 (88 mg, 173 μmol) was dissolved in MeCN (1 mL) and 4N HCl in dioxane (0.3 mL) and stirred at room temperature for 10 minutes, then concentrated under reduced pressure to yield the title compound (34 mg) as an HCl salt.

Preparation 9: (2S,4R)-4-t-Butoxycarbonylamino-5-(3'-chlorobiphenyl-4-yl)-2-hydroxymethyl-2-methyl-pentanoic Acid Ethyl Ester

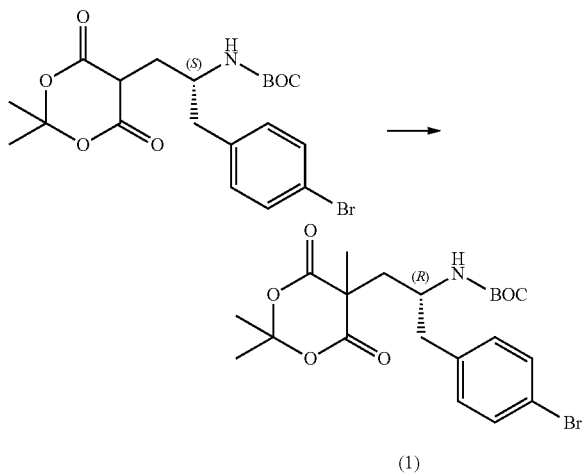

To a mixture of [(S)-1-(4-Bromo-benzyl)-2-(2,2-dimethyl-4,6-dioxo-[1,3]dioxan-5-yl)ethyl]carbamic acid t-butyl ester (44 g, 96 mmol) and $K_2CO_3$ (17.3 g, 125 mmol) in DMF (320 mL) was added dropwise $CH_3I$ (27.4 g, 193 mmol) at 0° C. The mixture was stirred at room temperature for 4 hours, diluted with water (1 L), and extracted with EtOAc (3×200 mL). The combined organic layers were washed with saturated aqueous NaCl (1 L), dried over $Na_2SO_4$ and concentrated to yield the crude product which was further purified by washing with $Et_2O$ (100 mL) to yield Compound 1 (37 g) as a white solid. LC-MS: [M-Boc+H]$^+$: 370, 372.

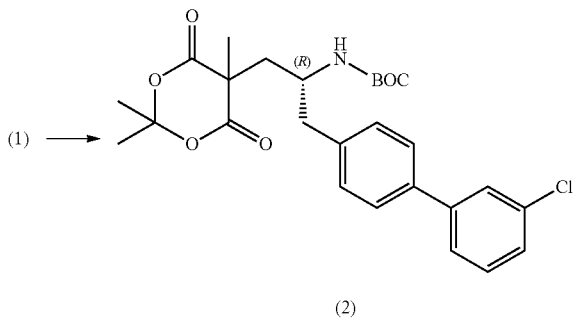

A mixture of Compound 1 (15 g, 31.9 mmol), 3-chlorophenylboronic acid (5.5 g, 35.1 mmol), KF (3.7 g, 63.8 mmol), and Pd(dppf)Cl$_2$ (700 mg, 950 μmol) in 1,4-dioxane (150 mL) and water (150 mL) was stirred at 60° C. overnight. After evaporation of the solvent, the mixture was extracted with EtOAc (3×200 mL). The combined organic layers were washed with saturated aqueous NaCl (0.7 L), dried over $Na_2SO_4$ and concentrated to yield the crude product which was further purified by normal phase column chromatography (PE:EtOAc=8:1) to yield Compound 2 (9 g) as a white solid. LC-MS: [M-Boc+H]$^+$: 402.

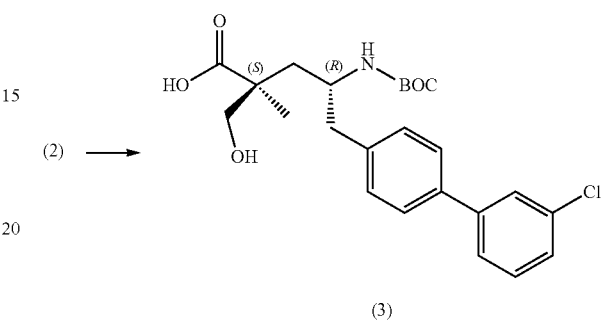

Samarium powder (72 g, 480 mmol) was flushed with argon for 20 minutes. Anhydrous THF (250 mL) was added and the resulting suspension was bubbled with argon for 15 minutes. Iodine (97 g, 384 mmol) was added and the flask flushed again with argon for 10 minutes. The flask was covered in aluminum foil and heated at 70° C. overnight, yielding a blue solution. The freshly prepared $SmI_2$ solution was cooled to room temperature and used directly.

A solution of Compound 2 (8 g, 16 mmol) in dry THF (200 mL) and water (100 mL) was sealed and degassed. The $SmI_2$ solution (1.6 L) was added to the cooled solution via cannula, and stirred at room temperature for 2 hours. The mixture was concentrated and 10% citric acid (60 mL) was added. The mixture was extracted with EtOAc (4×100 mL), and the combined organic layers were dried with $Na_2SO_4$, concentrated, and purified by normal phase column chromatography (PE:EtOAc=2:1 with 1% AcOH) to yield Compound 3 (3.2 g) as a white solid. LC-MS: [M-Boc+H]$^+$: 348.

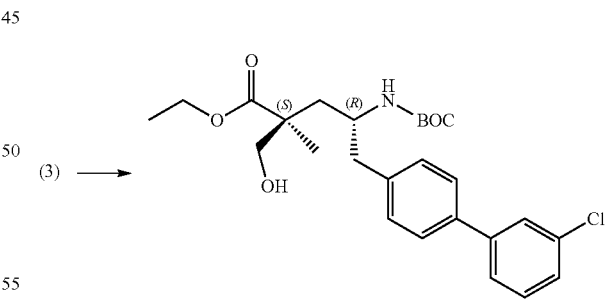

To a solution of Compound 3 (3.2 g, 7.1 mmol) and Ag$_2$O (2.5 g, 10 mmol) in MeCN (100 mL), was added ethyl iodide (2.2 g, 14 mmol). The mixture was stirred at room temperature for 2 hours. The mixture was filtered, and the filtrate was concentrated and purified by silica gel chromatography (PE:EtOAc=2:1) to yield the title compound (3.7 g) as a white solid. LC-MS: [M-Boc+H]$^+$: 376. $^1$H NMR (400 MHz, DMSO): 7.67 (1H, s), 7.61-7.59 (3H, m), 7.50-7.46 (1H, m), 7.41-7.39 (1H, m), 7.25 (2H, d, J=8.0 Hz), 6.56 (1H, d, J=12 Hz), 4.74-4.71 (1H, m), 4.01-3.95 (2H, m), 3.75-3.65 (1H, m), 3.42-3.32 (2H, m), 2.65-2.62 (2H, m), 1.75-1.55 (2H, m), 1.27 (9H, s), 1.13 (3H, t, J=7.5 Hz), 1.11 (3H, s).

Preparation 10: (2S,4R)-5-(5'-Chloro-2'-fluorobiphenyl-4-yl)-2-hydroxymethyl-2-methyl-4-methylaminopentanoic Acid Compound 1 was prepared as described herein.

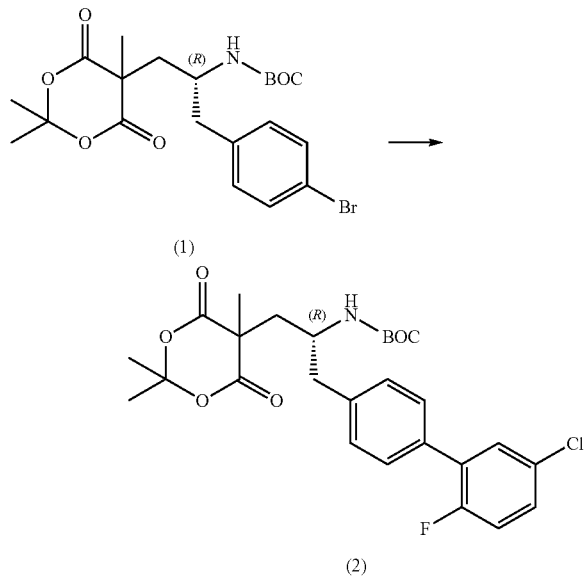

A mixture of Compound 1 (10.5 g, 22.3 mmol), 5-chloro-2-fluorophenylboronic acid (4.3 g, 24.6 mmol), KF (2.6 g, 44.7 mmol), and Pd(dppf)Cl$_2$ (490 mg, 670 μmol) in 1,4-dioxane (100 mL) and water (100 mL) was stirred at 60° C. overnight. The mixture was concentrated, diluted with water (100 mL), and extracted with EtOAc (2×100 mL). The combined organic layers were washed with saturated aqueous NaCl (0.5 L), dried over Na$_2$SO$_4$ and concentrated to yield the crude product which was further purified by normal phase column chromatography (PE:EtOAc=8:1) to yield Compound 2 (9.5 g) as a white solid.

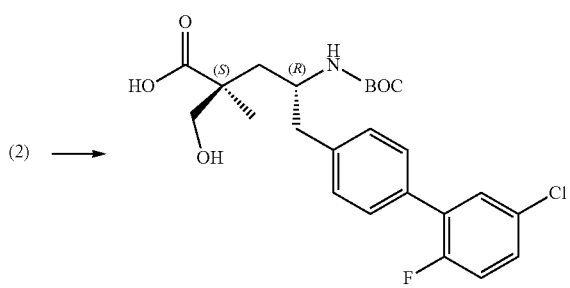

Samarium powder (60 g, 400 mmol) was flushed with argon. Anhydrous THF (1.6 L) was added and the resulting suspension was bubbled with argon. Iodine (81 g, 320 mmol) was added and the flask flushed again with argon. The flask was then heated at 66° C. overnight, yielding a blue solution. The freshly prepared SmI$_2$ solution was cooled to room temperature and used directly.

A solution of Compound 2 (8 g, 15.4 mmol) in dry THF (200 mL) and water (100 mL) was sealed and flushed with argon, then cooled to −30° C. The SmI$_2$ solution (1.6 L) was added to the cooled solution and stirred at room temperature for 1.5 hours. The mixture was concentrated and 10% citric acid (500 mL) was added. The mixture was extracted with EtOAc (2×300 mL), dried over Na$_2$SO$_4$, and filtered. The organic layer was concentrated and the residue was purified by column chromatography (DCM: EtOAc=5:1) to yield the title compound (3.6 g) as a white solid. LC-MS: [M+Na]$^+$: 488. $^1$H NMR (300 MHz, CDCl$_3$) δ 7.42 (dt, J=5.8, 2.9 Hz, 2H), 7.36 (dd, J=7.0, 2.1 Hz, 1H), 7.26 (s, 1H), 7.22 (t, J=3.4 Hz, 1H), 7.06 (dd, J=9.8, 8.8 Hz, 1H), 6.79 (d, J=10.4 Hz, 1H), 4.06 (dd, J=17.5, 9.2 Hz, 2H), 3.47 (d, J=11.5 Hz, 1H), 2.68 (m, 2H), 2.15 (m, 2H), 1.28 (m, 12H).

Preparation 11: (2S,4R)-4-Amino-5-(3'-chlorobiphenyl-4-yl)-2-ethoxymethyl-2-methylpentanoic Acid Ethyl Ester

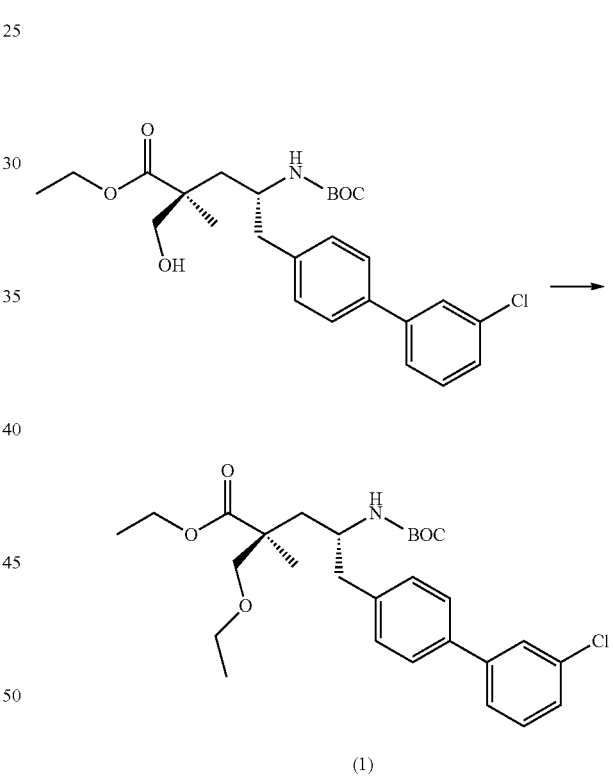

(2S,4R)-4-t-Butoxycarbonylamino-5-(3'-chlorobiphenyl-4-yl)-2-hydroxymethyl-2-methylpentanoic acid ethyl ester (1.4 g, 3.0 mmol) was combined with 10N NaOH (2.1 mL, 21.2 mmol), DCM (16 mL), and tetrabutylammonium hydrogen sulfate (206 mg, 607 μmol), followed by diethyl sulfate (1.9 g, 12.2 mmol). The reaction flask was capped and stirred vigorously overnight. The material was extracted with DCM and water. The mixture was concentrated under reduced pressure and purified by normal phase column chromatography (0-100% EtOAc/hexanes) to yield Compound 1 (450 mg, 29% yield).

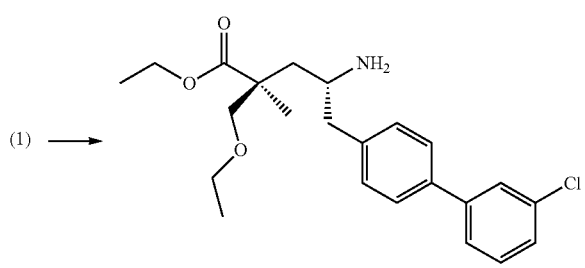 [SMILES: CCOC[C@](C)(C[C@H](N)Cc1ccc(-c2cccc(Cl)c2)cc1)C(=O)OCC]

(1) →

Compound 1 (290 mg, 575 μmol) was dissolved in MeCN (4 mL) and 4N HCl in dioxane (2 mL) and stirred for 10 minutes. The solution was then concentrated under reduced pressure to yield the title compound as an HCl salt.

Preparation 12: (2S,4R)-4-t-Butoxycarbonylamino-5-(5'-chloro-2'-fluoro-biphenyl-4-yl)-2-ethoxymethyl-2-methylpentanoic Acid

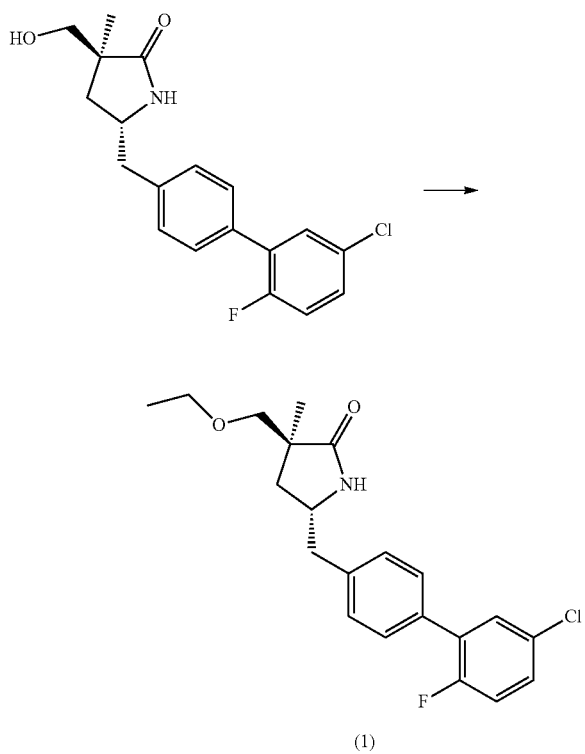

To a solution of (3S,5R)-5-(5'-Chloro-2'-fluorobiphenyl-4-ylmethyl)-3-hydroxymethyl-3-methylpyrrolidin-2-one (4.0 g, 11.5 mmol) in acetone (80 mL) was added NaOH (23 mL, 115 mmol) and diethyl sulfate (2.2 g, 13.8 mmol). The mixture was stirred at room temperature for 3 days. The mixture was then diluted with water (80 mL) and EtOAc (50 mL), and the aqueous layer was extracted with EtOAc (3×50 mL). The combined organic phases were dried over Na$_2$SO$_4$, filtered, concentrated. The residue was purified by column chromatography (PE:EtOAc=1:1.5) to yield Compound 1 (1.9 g) as a yellow oil. LC-MS: [M+H]+:376.

(1) →

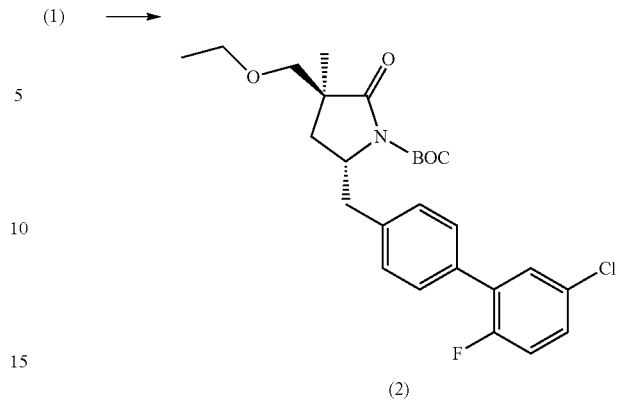

Compound 1 (1.6 g, 4.3 mmol) was dissolved in THF (15 mL) and purged with nitrogen, followed by cooling to 0° C. NaHMDS (6.4 mL, 6.4 mmol) was added and the resulting mixture was stirred for 30 min from 0° C. to room temperature. (BOC)$_2$O (1.4 g, 6.4 mmol) was added, and the mixture was stirred for 30 minutes; the resulting solution containing Compound 2 was used without any further work-up. LC-MS: [M+Na]$^+$:498.

(2) →

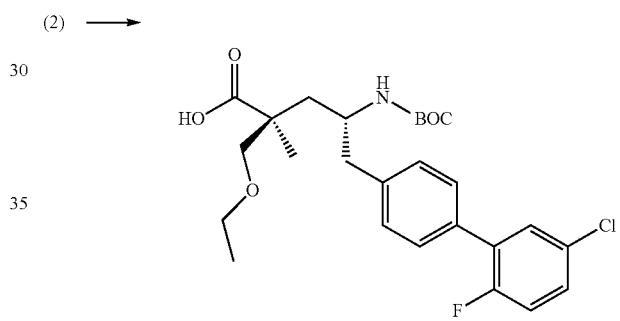

The crude solution of Compound 2 was combined with NaOH (4.2 mL, 42 mmol) and stirred at room temperature overnight. EtOAc (50 mL) was added and the mixture was acidified to pH 5 with 1N HCl. The layer was extracted (2×30 mL), dried over Na$_2$SO$_4$, filtered and concentrated to yield the title compound (1.7 g) as a colorless foam. LC-MS: [M+Na]$^+$:516. $^1$H NMR (300 MHz, CDCl$_3$) δ 7.39 (m, 3H), 7.24 (m, 3H), 7.03 (m, 2H), 3.91 (s, 1H), 3.74 (d, J=9.3 Hz, 1H), 3.52 (m, 3H), 2.71 (ddd, J=21.9, 13.3, 6.8 Hz, 2H), 2.04 (dd, J=15.5, 10.7 Hz, 1H), 1.85 (d, J=13.0 Hz, 1H), 1.23 (m, 15H).

Preparation 13: [(S)-1-(5'-Chloro-2'-fluorobiphenyl-4-ylmethyl)-2-(2,2-dimethyl-4,6-dioxo-[1,3]dioxan-5-yl)-ethyl]carbamic Acid t-Butyl Ester

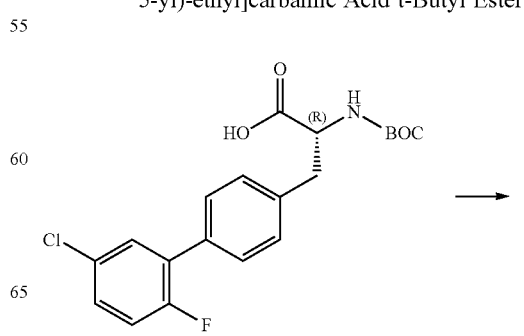

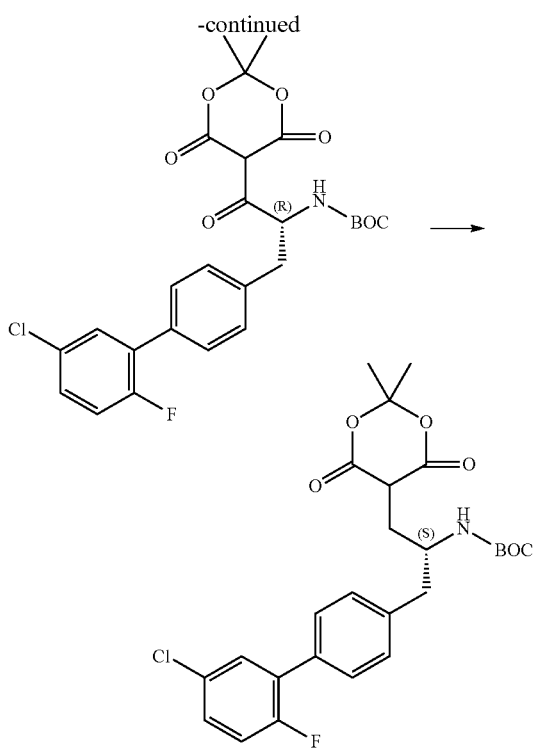

To a 0-5° C. solution of (R)-2-t-butoxycarbonylamino-3-(5'-chloro-2'-fluorobiphenyl-4-yl)-propionic acid (25.0 g, 63.5 mmol), Meldrum's acid (10.1 g, 69.8 mmol, 1.1 eq.), and DMAP (11.6 g, 95 mmol, 1.5 eq.) in DCM (250 mL) was added dropwise a solution of DCC (14.4 g, 69.8 mmol, 1.1 eq.) in DCM (25 mL). The mixture was stirred at 0-5° C. overnight. The resulting suspension was filtered and the filtrate was washed with 1.0 M HCl (200 mL) and saturated aqueous NaCl (150 mL), then dried over $Na_2SO_4$, and filtered to yield a crude amber solution.

AcOH (22 mL, 380 mmol, 6 eq.) was added to the crude solution, then $NaBH_4$ (4.3 g, 114 mmol, 1.8 eq.) was added in three portions over three minutes, and the resulting mixture was stirred at room temperature for three hours. The reaction was then quenched with saturated aqueous NaCl (100 mL) added dropwise, and the organic layer was sequentially washed with saturated aqueous NaCl (200 mL), water (2×200 mL), saturated aqueous $NaHCO_3$ (200 mL), and saturated aqueous NaCl (200 mL), before being dried over $Na_2SO_4$, filtered, and concentrated in vacuo to yield the title compound as a yellow oil.

Preparation 14: (R)-4-Amino-5-(5'-chloro-2'-fluoro-biphenyl-4-yl)-2-ethyl-2-hydroxymethylpentanoic Acid (isomers a and b)

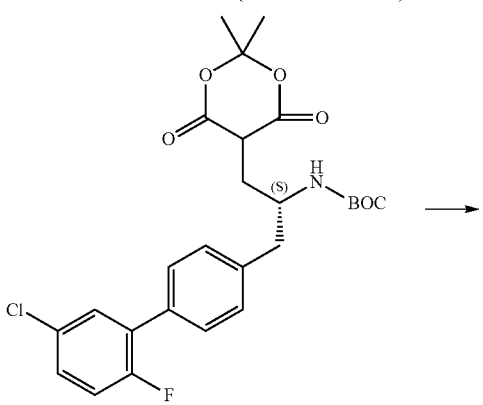

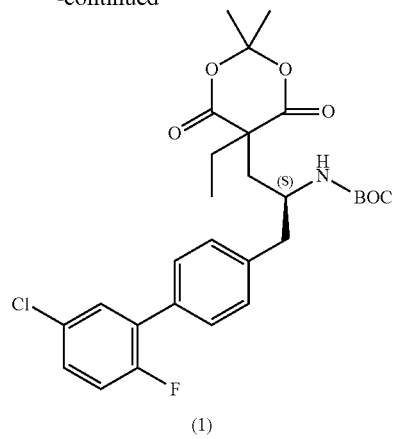

(1)

[(S)-1-(5'-Chloro-2'-fluorobiphenyl-4-ylmethyl)-2-(2,2-dimethyl-4,6-dioxo-[1,3]dioxan-5-yl)-ethyl]carbamic acid t-butyl ester (300 mg, 594 μmol, 1.0 eq.) was dissolved in DMF (3 mL) and the resulting solution was cooled to 0° C. Potassium carbonate (164 mg, 654 μmol, 1.1 eq.) was added and the mixture stirred at 0° C. for 15 minutes, then iodoethane (102 mg, 694 μmol, 1.2 eq.) was added and the mixture was stirred at room temperature overnight. The mixture was then heated to 50° C. for 4 hours and when complete (as determined by LC/MS analysis), the reaction was quenched with water (20 mL). EtOAc (20 mL) was added and the phases were separated. The aqueous phase was extracted with EtOAc (20 mL). The organic phases were combined and dried over $Na_2SO_4$ and concentrated in vacuo to yield crude Compound 1 (300 mg). The material was used without further purification in the next step. LCMS (ESI): calc. $C_{28}H_{33}ClFNO_6$=534; obs. M+H=534.0. Retention time: 4.15 min. (LC/MS Method 2).

(1) →

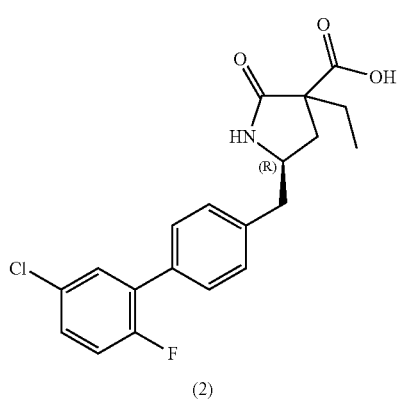

(2)

Compound 1 (300 mg, 594 nmol, 1.0 equiv.) was dissolved in 4M HCl (10 mL) in p-dioxane and stirred at room temperature for 30 minutes, and when the reaction was complete (as determined by LC/MS analysis), the solution was concentrated in vacuo to near dryness. The crude material was treated with water (2 mL), and then concentrated in vacuo. The resulting oil was azeotroped in vacuo with toluene (2×15 mL) to yield crude Compound 2 (160 mg). LCMS (ESI): calc. $C_{20}H_{19}ClFNO_3$=375; obs. M+H=375.9. Retention time: 3.19 min. (LC/MS Method 2).

(2) → 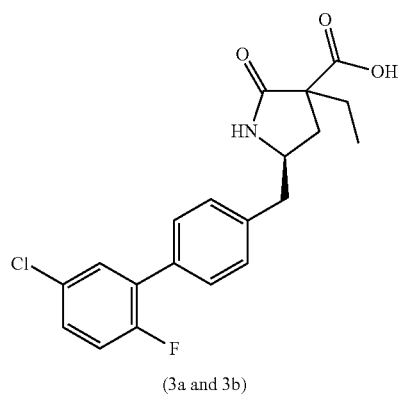

(3a and 3b)

Compound 2 (160 mg, 427 nmol, 1.0 eq.) was dissolved in THF (5 mL) and N-methylmorpholine (210 μL, 854 nmol, 2.0 eq.) was added. The resulting mixture was cooled to 0° C. for 15 minutes, then isobutyl chloroformate (210 μL, 1900 nmol, 4.4 eq.) was added dropwise and the solution stirred at 0° C. for 15 minutes. A solution of NaBH$_4$ (65 mg, 1.7 mmol, 4.0 eq.) in water (2 mL) was added in three portions, allowing one minute in between each addition. The mixture was stirred for ten minutes at 0° C., and when complete (as determined by LC/MS analysis), the reaction was quenched with saturated aqueous NaHCO$_3$ (5 mL) and allowed to warm to room temperature. EtOAc was added and the phases were separated. The aqueous phase was extracted with another portion of EtOAc, and the combined organic phases were dried over Na$_2$SO$_4$ and concentrated. The crude material was purified by column chromatography (100% EtOAc, silica gel column) to yield two isomers: Compound 3a (50 mg) (late eluting) and Compound 3b (55 mg) (early eluting). LCMS (ESI): calc. $C_{20}H_{21}ClFNO_2=361$; obs. M+H=362.1. Retention time: 5.24 min. (LC/MS Method 1).

(3a) → 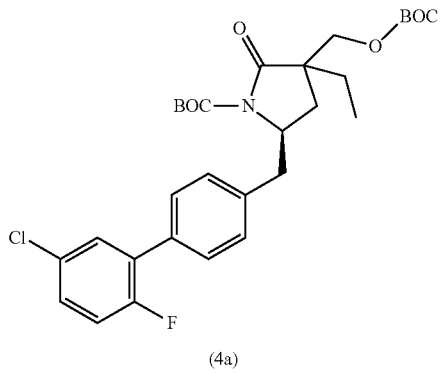

(4a)

Compound 3a (50 mg, 140 μmol, 1.0 eq.) was dissolved in THF (2.0 mL). The solution was cooled to −40° C., then NaHMDS (1.0M, 400 μL, 400 μmol, 2.9 eq.) was added and the resulting mixture was stirred for a few minutes at −40° C. Di-t-butyl dicarbonate (85 mg, 390 μmol, 2.8 eq.) was then added and the resulting solution was stirred at room temperature for 15 hours and when complete (as determined by LC/MS analysis), the reaction was quenched with a few drops of water and concentrated to yield crude Compound 4a (100 mg). LCMS (ESI): calc. $C_{30}H_{32}ClFNO_6=562$; obs. M+H=561.9. Retention time: 4.71 min. (LC/MS Method 2).

(4a) → 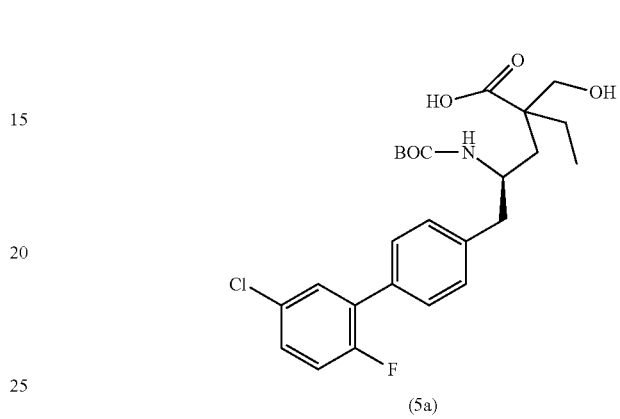

(5a)

Compound 4a (100 mg, 152 μmol, 1.0 eq.) was dissolved in a 1:1 THF/H$_2$O solution (4 mL). NaOH (150 mg, 3750 μmol, 24.7 eq.) was added, followed by a few drops of MeOH. The mixture was stirred overnight at room temperature and concentrated to dryness to yield crude Compound 5a. LCMS (ESI): calc. $C_{25}H_{31}ClFNO_5=479$; obs. M+H=479.9. Retention time: 4.36 min. (LC/MS Method 2).

(5a) → 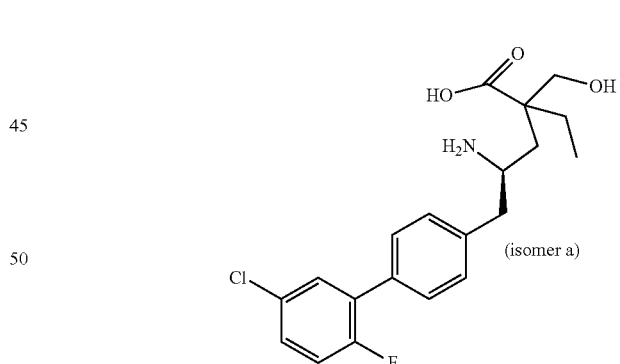

(isomer a)

Compound 5a was dissolved in 4M HCl (5 mL) in 1,4-dioxane and stirred at room temperature for two hours and when complete (as determined by LC/MS analysis), the mixture was concentrated in vacuo and treated with water (1 mL). The mixture was once more concentrated in vacuo and dried azeotropically by evaporation with toluene to yield the crude title compound (isomer a; 85 mg HCl salt), which was used without further purification. LCMS (ESI): calc. $C_{20}H_{23}ClFNO_3=379$; obs. M+H=380.1. Retention time: 2.68 min. (LC/MS Method 2).

(3b) →

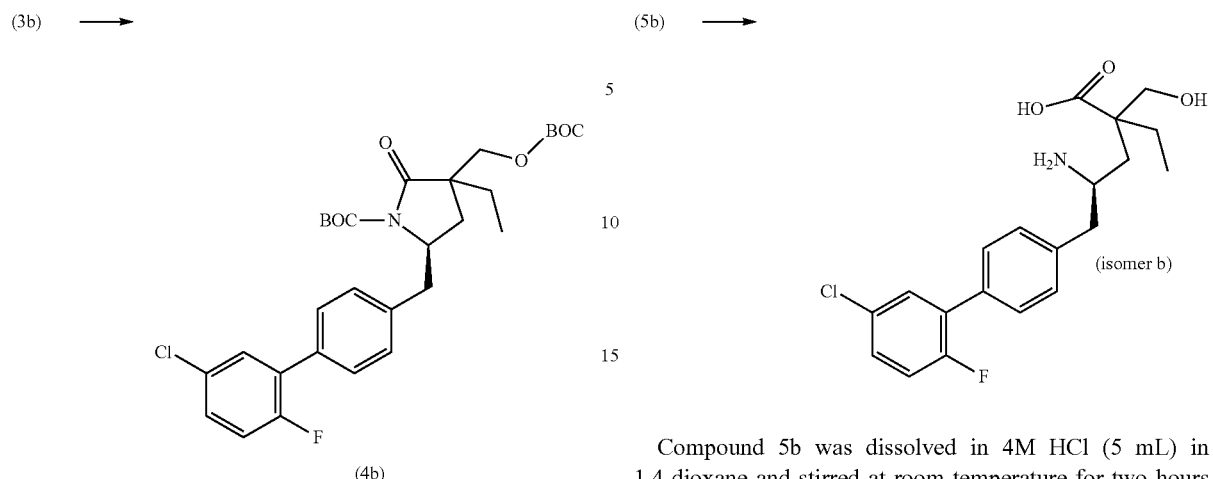

(4b)

Compound 3b (55 mg, 152 μmol, 1.0 eq.) was dissolved in THF (2.0 mL). The solution was cooled to −40° C., then NaHMDS (1.0M, 380 μL, 380 μmol, 2.5 eq.) was added and the resulting mixture was stirred for a few minutes at −40° C. (BOC)$_2$O (84 mg, 380 μmol, 2.0 eq.) was then added and the resulting solution was stirred at room temperature for 15 hours and when complete (as determined by LC/MS analysis), the reaction was quenched with a few drops of water and concentrated to yield crude Compound 4b (100 mg). LCMS (ESI): calc. $C_{30}H_{32}ClFNO_6$=562; obs. M+H=562.4. Retention time: 4.75 min. (LC/MS Method 2).

(4b) →

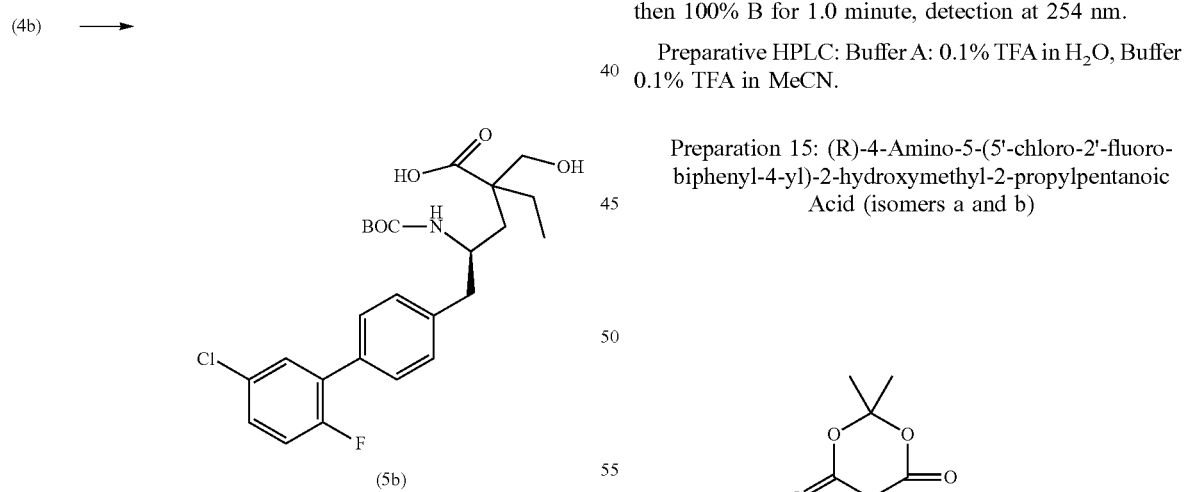

(5b)

Compound 4b (100 mg, 152 μmol, 1.0 eq.) was dissolved in a 1:1 THF/H$_2$O solution (4 mL). NaOH (150 mg, 3750 μmol, 24.7 eq.) was added, followed by a few drops of MeOH. The mixture was stirred overnight at room temperature and concentrated to dryness to yield crude Compound 5b (yield not calculated). LCMS (ESI): calc. $C_{25}H_{31}ClFNO_5$=479; obs. M+H=479.8 min. Retention time: 4.30 min. (LC/MS Method 2).

(5b) →

(isomer b)

Compound 5b was dissolved in 4M HCl (5 mL) in 1,4-dioxane and stirred at room temperature for two hours and when the reaction was complete (as determined by LC/MS analysis), the mixture was concentrated in vacuo and treated with water (1 mL). The mixture was once more concentrated in vacuo and dried azeotropically by evaporation with toluene to yield the crude title compound (isomer b; 85 mg HCl salt), which was used without further purification. LCMS (ESI): calc. $C_{20}H_{23}ClFNO_3$=379; obs. M+H=380.2. Retention time: 2.67 min. (LC/MS Method 2).

LC/MS Method 1: flow rate: 1.5 mL/min; Buffer A: 0.1% TFA/H$_2$O; Buffer B 0.1% TFA/MeCN; gradient elution from 5%-100% B over 9.6 minutes, then 100% B for 1.0 minute, detection at 254 nm. LC/MS Method 2: flow rate: 1.5 mL/min; Buffer A: 0.1% TFA/H$_2$O; Buffer B 0.1% TFA/MeCN; gradient elution from 5%-100% B over 3.6 minutes, then 100% B for 1.0 minute, detection at 254 nm.

Preparative HPLC: Buffer A: 0.1% TFA in H$_2$O, Buffer B: 0.1% TFA in MeCN.

Preparation 15: (R)-4-Amino-5-(5'-chloro-2'-fluoro-biphenyl-4-yl)-2-hydroxymethyl-2-propylpentanoic Acid (isomers a and b)

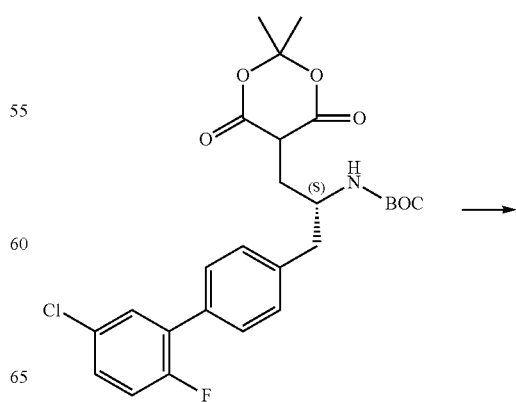

-continued

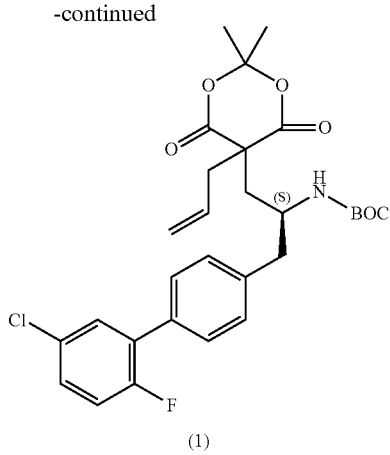

(1)

[(S)-1-(5'-Chloro-2'-fluorobiphenyl-4-ylmethyl)-2-(2,2-dimethyl-4,6-dioxo-[1,3]dioxan-5-yl)-ethyl]carbamic acid t-butyl ester (600 mg, 1190 μmol, 1.0 eq.) was dissolved in DMF (5 mL) and the resulting solution was cooled to 0° C. Potassium carbonate (328 mg, 2380 μmol, 2.0 eq.) was added and the mixture was stirred at 0° C. for ten minutes, then allyl bromide (120 μL, 1390 μmol, 1.2 eq.) was added and the mixture was stirred at 0° C. for 30 minutes then allowed to stir at room temperature overnight and when complete (as determined by LC/MS analysis), the reaction was quenched with saturated aqueous NaCl (10 mL). EtOAc (20 mL) was added and the phases were separated. The aqueous phase was extracted with EtOAc (10 mL). The organic phases were combined and dried over $Na_2SO_4$ and concentrated in vacuo to yield crude Compound 1 (720 mg). The material was used without further purification in the next step. LCMS (ESI): calc. $C_{29}H_{33}ClFNO_6$=545.9; obs. M+H=546.0. Retention time: 4.18 min. (LC/MS Method 2).

(1) ⟶

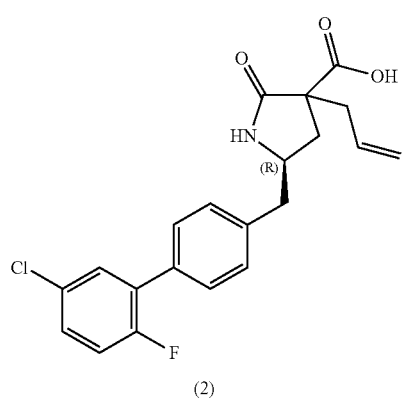

(2)

Compound 1 (720 mg, 1190 μmol, 1.0 eq.) was dissolved in 4M HCl (5 mL) in 1,4-dioxane and stirred at room temperature for one hour, and when the reaction was complete (as determined by LC/MS analysis), the mixture was concentrated in vacuo to near dryness. The crude material was treated with water (2 mL), and then concentrated in vacuo. The resulting oil was stripped in vacuo with toluene (2×15 mL) to yield crude Compound 2 (530 mg). LCMS (ESI): calc. $C_{21}H_{19}ClFNO_3$=387; obs. M+H=388.1. Retention time: 3.34 min. (LC/MS Method 2).

(2) ⟶

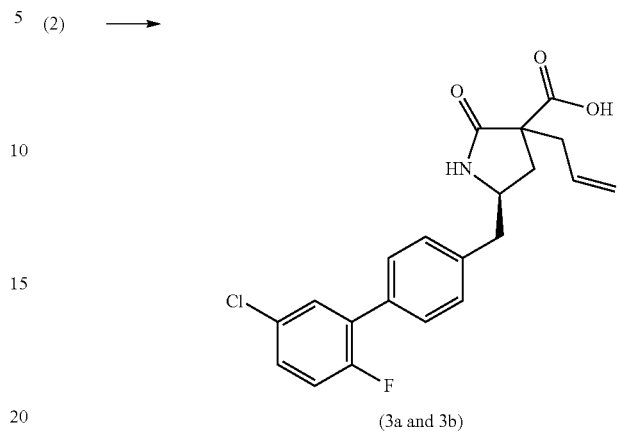

(3a and 3b)

Compound 2 (530 mg, 1370 μmol, 1.0 eq.) was dissolved in THF (5 mL) and N-methylmorpholine (680 μL, 6200 μmol, 4.5 eq.) was added. The resulting mixture was cooled to 0° C. for 15 minutes, then isobutyl chloroformate (360 μL, 2740 μmol, 2.0 eq.) was added dropwise and the solution stirred at 0° C. for 15 minutes. A solution of $NaBH_4$ (144 mg, 5.5 mmol, 4.0 eq.) in water (2 mL) was added in three portions, allowing one minute in between each addition. The mixture was stirred for ten minutes at 0° C. and when complete (as determined by LC/MS analysis), the reaction was quenched with saturated aqueous $NaHCO_3$ (5 mL) and allowed to warm to room temperature. EtOAc was added and the phases were separated. The aqueous phase was extracted with another portion of EtOAc, and the combined organic phases were dried over $Na_2SO_4$ and concentrated. The crude material was purified by column chromatography (100% EtOAc, silica gel column) to yield two isomers: Compound 3a (150 mg) (late eluting) and Compound 3b (150 mg) (early eluting). LCMS (ESI): calc. $C_{21}H_{21}ClFNO_2$=373; obs. M+H=374.0. Retention time: 3.29 min. (LC/MS Method 2).

(3a) ⟶

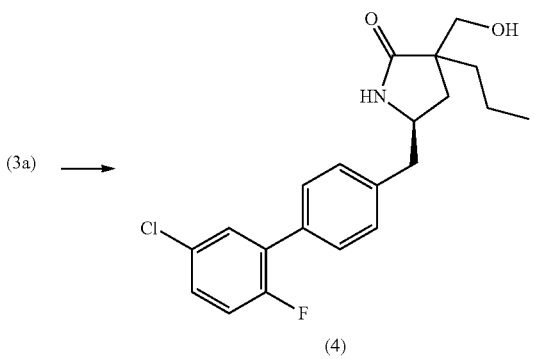 [SMILES: CCCC1(CO)C[C@@H](Cc2ccc(-c3cc(Cl)ccc3F)cc2)NC1=O]

(4)

Compound 3a (70 mg, 187 μmol, 1.0 eq.) was dissolved in a 1:1 EtOAc:MeOH solution (2 mL). 10% Pd/C (4.8 mg) was added and the mixture was stirred under hydrogen (1 atm). LC/MS analysis after 30 minutes revealed a mixture of starting material and desired product. Additional 10% Pd/C (1.7 mg) and MeOH was added. LC/MS analysis after 1.5 hours showed that the reaction was complete. The mixture was filtered through a pad of Celite®, and the pad was washed with additional MeOH and EtOAc. The combined solutions were dried in vacuo to yield Compound 4 (44 mg). LCMS (ESI): calc. $C_{21}H_{23}ClFNO_2$=375; obs. M+H=376.3. Retention time: 3.42 min. (LC/MS Method 2).

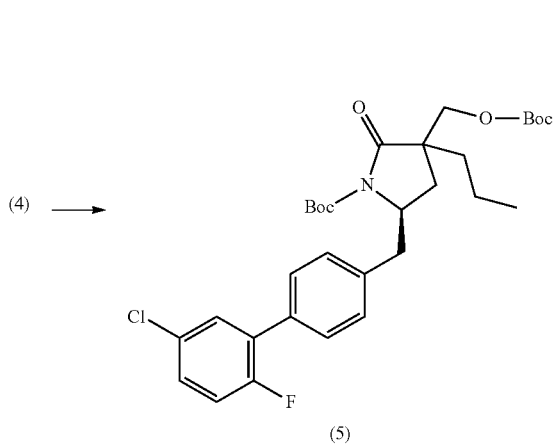 [SMILES: CCCC1(COC(=O)OC(C)(C)C)C[C@@H](Cc2ccc(-c3cc(Cl)ccc3F)cc2)N(C(=O)OC(C)(C)C)C1=O]

(4) →

(5)

Compound 4 (40 mg, 110 μmol, 1.0 eq.) was dissolved in THF (2.0 mL). The solution was cooled to −40° C., then NaHMDS (1.0M, 270 μL, 270 μmol, 2.0 eq.) was added and the resulting mixture was stirred at −40° C. for 15 minutes. (BOC)$_2$O (59 mg, 273 μmol, 2.0 eq.) was added and the resulting solution was stirred at room temperature for 15 hours and when complete (as determined by LC/MS analysis), the reaction was quenched with water (2 mL) and extracted with DCM. The organic phase was concentrated to yield crude Compound 5 (60 mg). LCMS (ESI): calc. $C_{31}H_{39}ClFNO_6$=576; obs. M+H=576.3. Retention time: 4.81 min. (LC/MS Method 2).

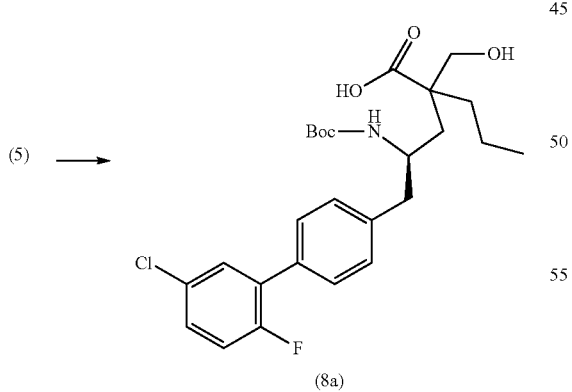

(5) →

(8a)

Compound 5 (60 mg, 228 μmol, 1.0 eq.) was dissolved in a 1:1 THF/H$_2$O solution (2 mL). NaOH (104 mg, 2.6 mmol, 11.4 eq.) was added, followed by a few drops of MeOH. The mixture was stirred overnight at room temperature and the pH was adjusted to 2 with 1N HCl. The mixture was extracted with DCM (2×15 mL), and the aqueous phase discarded. The combined organics were concentrated to dryness to obtain crude Compound 8a (50 mg). LCMS (ESI): calc. $C_{26}H_{33}ClFNO_5$=494; obs. M+H=493.8 min. Retention time: 4.46 min. (LC/MS Method 2).

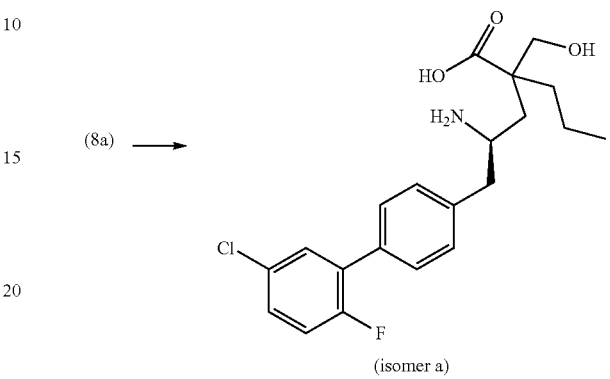

(8a) →

(isomer a)

Compound 8a was dissolved in 4M HCl (5 mL) in 1,4-dioxane and stirred at room temperature for 30 minutes and when the reaction was complete (as determined by LC/MS analysis), the mixture was concentrated in vacuo to yield the crude title compound (isomer a; 40 mg HCl salt), which was used without further purification. LCMS (ESI): calc. $C_{21}H_{25}ClFNO_3$=393; obs. M+H=394.0. Retention time: 2.79 min. (LC/MS Method 2).

(3b) →

(6)

Compound 3b (150 mg, 400 μmol, 1.0 eq.) was dissolved in THF (4.0 mL). The solution was cooled to −40° C., then NaHMDS (1.0M, 1 L, 800 μmol, 2.5 eq.) was added and the resulting mixture was stirred at −40° C. for 15 minutes. (BOC)$_2$O (218 mg, 1 mol, 2.5 eq.) was added and the resulting solution was stirred at room temperature for 15 hours and when complete (as determined by LC/MS analysis), the reaction was quenched with water (2 mL) and extracted with DCM. The organic phase was concentrated to yield crude Compound 6 (150 mg). LCMS (ESI): calc. $C_{31}H_{32}ClFNO_6$=574; obs. M+H=574.2. Retention time: 4.75 min. (LC/MS Method 2).

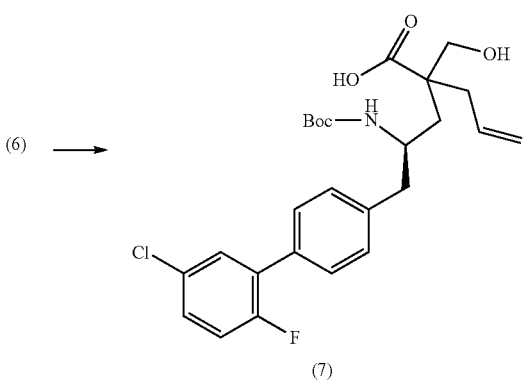 [SMILES: C=CCC(CO)(C[C@@H](Cc1ccc(-c2cc(Cl)ccc2F)cc1)NC(=O)OC(C)(C)C)C(=O)O]

Compound 6 (50 mg, 87 μmol, 1.0 eq.) was dissolved in a 1:1 THF/H$_2$O solution (2 mL). NaOH (9 mg, 218 μmol, 2.5 eq.) was added, followed by a few drops of MeOH. The mixture was stirred overnight at room temperature and the pH was adjusted to 2 with 1N HCl. The mixture was extracted with DCM, and the aqueous phase discarded. The organics were concentrated to dryness to yield crude Compound 7 (70 mg). LCMS (ESI): calc. C$_{26}$H$_{31}$ClFNO$_5$=491; obs. M+H=492.2 min. Retention time: 3.64 min. (LC/MS Method 2).

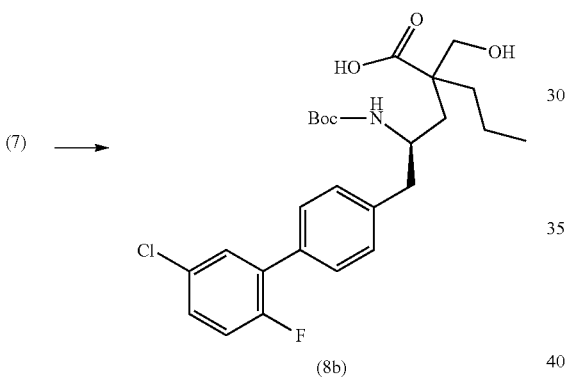

Compound 7 (70 mg, 187 μmol, 1.0 eq.) was dissolved in EtOAc (2 mL) and ten drops of MeOH. 10% Pd/C (5 mg) was added and the mixture was stirred under hydrogen at one atmosphere of pressure. LC/MS analysis after three hours showed that the reaction was complete. The mixture was filtered through a pad of Celite®, and the pad was washed with EtOAc (20 mL). The combined solutions were dried in vacuo to yield Compound 8b (70 mg). LCMS (ESI): calc. C$_{26}$H$_{33}$ClFNO$_5$=493; obs. M+H=494.0. Retention time: 4.42 min. (LC/MS Method 2).

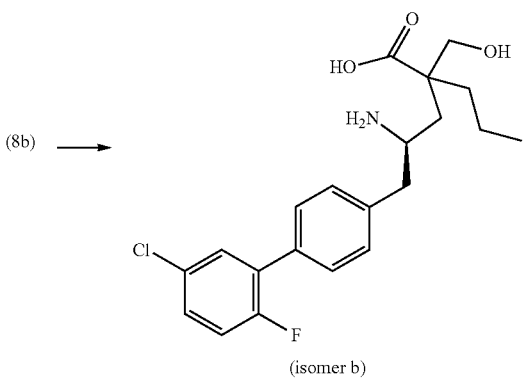 [SMILES: CCCC(CO)(C[C@H](N)Cc1ccc(-c2cc(Cl)ccc2F)cc1)C(=O)O]

Compound 8b was dissolved in 4M HCl (4 mL) in 1,4-dioxane and stirred at room temperature for three hours and when the reaction was complete (as determined by LC/MS analysis), the mixture was concentrated in vacuo to yield the crude title compound (isomer b; 60 mg HCl salt) which was used without further purification. LCMS (ESI): calc. C$_{21}$H$_{25}$ClFNO$_3$=393; obs. M+H=394.0. Retention time: 2.74 min. (LC/MS Method 2).

LC/MS Method 1: flow rate: 1.5 mL/min; Buffer A: 0.1% TFA/H$_2$O; Buffer B 0.1% TFA/MeCN; gradient elution from 5%-100% B over 9.6 minutes, then 100% B for 1.0 minute, detection at 254 nm. LC/MS Method 2: flow rate: 1.5 mL/min; Buffer A: 0.1% TFA/H$_2$O; Buffer B 0.1% TFA/MeCN; gradient elution from 5-100% B over 3.6 minutes, then 100% B for 1.0 minute, detection at 254 nm.

Preparative HPLC: Buffer A: 0.1% TFA in H$_2$O, Buffer B: 0.1% TFA in MeCN.

Preparation 16: 3-[(R)-2-Amino-3-(5'-chloro-2'-fluorobiphenyl-4-yl)-propyl]-3-hydroxymethyl-di-hydro-furan-2-one (isomers a and b)

Compounds 3a and 3b were prepared as described herein.

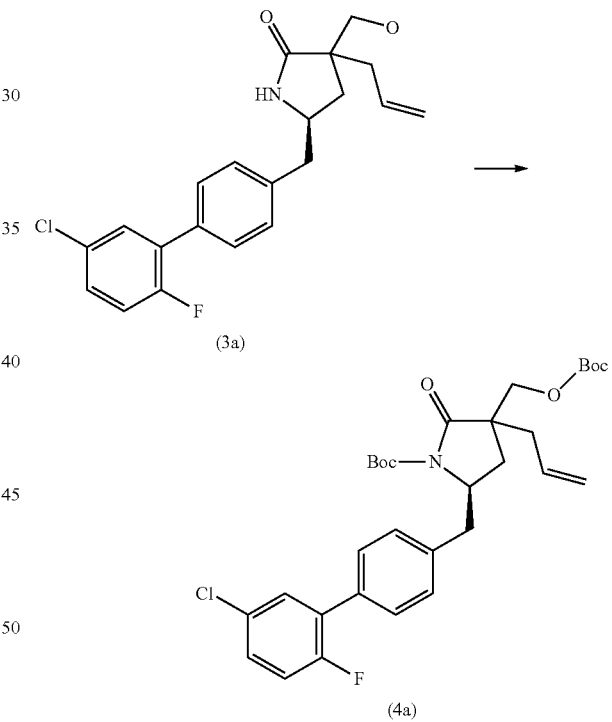

Compound 3a (isomer a; 36 mg, 96 μmol, 1.0 eq.) was dissolved in THF (2.0 mL). The solution was cooled to 0° C., then NaHMDS (1.0 M, 250 μL, 250 μmol, 2.5 eq.) was added. The resulting mixture was stirred for a few minutes at 0° C. then (BOC)$_2$O (53 mg, 458 μmol, 2.0 eq.) was added and the resulting solution was stirred at room temperature for 15 hours and when complete (as determined by LC/MS analysis), the reaction was quenched with 0.5N HCl (10 mL) and extracted with EtOAc (10 mL). The organic phase was concentrated to yield crude Compound 4a (isomer a; 40 mg). LCMS (ESI): calc. C$_{31}$H$_{37}$ClFNO$_6$=573; obs. M+H=574.2. Retention time: 4.76 min.

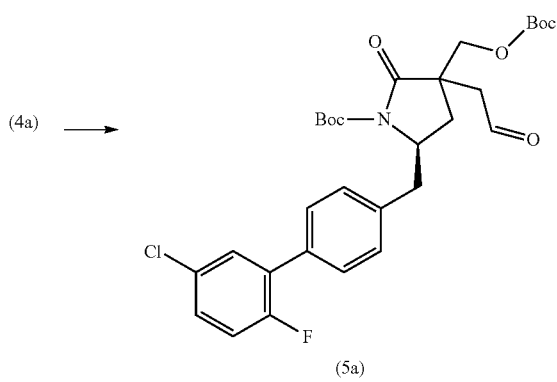 [SMILES: CC(C)(C)OC(=O)OCC1(CC=O)C[C@@H](Cc2ccc(-c3cc(Cl)ccc3F)cc2)N(C(=O)OC(C)(C)C)C1=O]

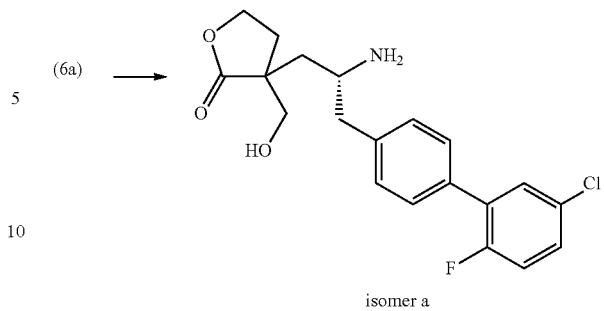

Compound 4a (isomer a; 40 mg, 70 µmol, 1.0 eq.) was dissolved in a 3:1 1,4-dioxane/water solution (4 mL). 2,6-Lutidine (16 µL, 137 µmol, 2.0 eq.), osmium tetroxide (2.5% in t-butanol, 10 mg, 0.7 µmol, 0.01 eq.), and sodium periodate (3 mg, 140 µmol, 2.0 eq.) were added and the resulting mixture was stirred at room temperature overnight and when the reaction was complete (as determined by LC/MS analysis), water was added and the mixture was extracted with DCM, and the aqueous phase was discarded. The organics were concentrated to dryness and purified by silica gel chromatography (0-30% EtOAc/hexanes, 25 g CombiFlash column, 15 min.) to yield pure Compound 5a (isomer a; 45 mg). LCMS (ESI): calc. $C_{30}H_{35}ClFNO_7$=575; obs. M+H=576.0. Retention time: 4.38 min.

Compound 6a (isomer a; 47 mg, 78 µmol, 1.0 eq.) was dissolved in 4M HCl in 1,4-dioxane (2 mL) and stirred at room temperature for 3 hours and when the reaction was complete (as determined by LC/MS analysis), the mixture was concentrated in vacuo to yield the crude title compound (isomer a 30 mg), which was used without further purification. LCMS (ESI): calc. $C_{20}H_{21}ClFNO_3$=377; obs. M+H=378.3. Retention time: 2.59 min.

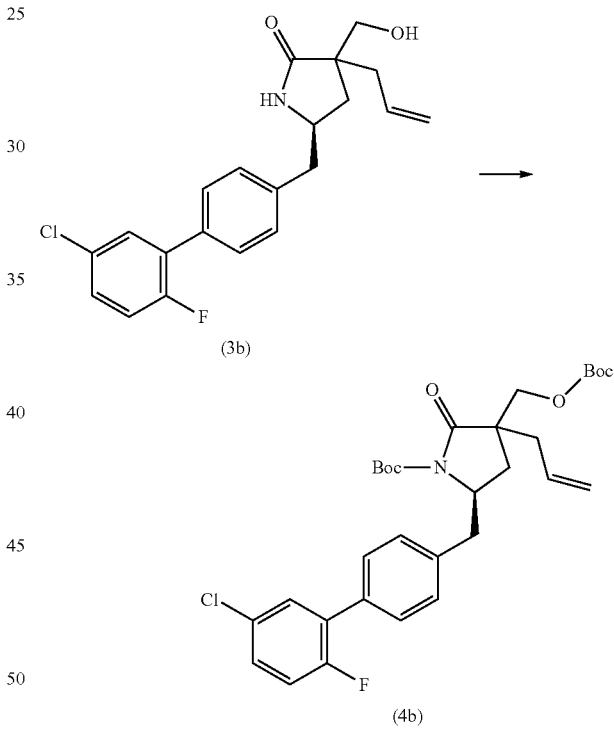

Compound 5a (isomer a; 45 mg, 78 µmol, 1.0 eq.) was dissolved in DCM (3 mL) and MeOH (1 mL) and cooled to 0° C. NaBH$_4$ (3 mg, 80 µmol, 1.0 eq.) was added and the mixture was stirred for five minutes at 0° C. and when complete (as determined by LC/MS analysis), the reaction was quenched with saturated aqueous NaHCO$_3$ (5 mL) and allowed to warm to room temperature. DCM (10 mL) was added and the phases were separated.

The aqueous phase was extracted with another portion of DCM, and the combined organic phases were dried over Na$_2$SO$_4$ and concentrated to yield crude Compound 6a (isomer a; 47 mg). LCMS (ESI): calc. $C_{30}H_{37}ClFNO_7$=577; obs. M+H=578.1. Retention time: 4.29 min.

Compound 3b (isomer b; 250 mg, 670 µmol, 1.0 eq.) was dissolved in THF (6.7 mL). The solution was cooled to −40° C., then NaHMDS (1.0 M, 1675 µL, 1675 µmol, 2.0 eq.) was added. The resulting mixture was stirred for 20 minutes at −40° C. then (BOC)$_2$O (365 mg, 1675 µmol, 2.0 eq.) was added and the resulting solution was stirred at room temperature for 15 hours and when complete (as determined by LC/MS analysis), the reaction was quenched with 0.5N HCl (10 mL) and extracted with EtOAc (10 mL). The organic phase was concentrated and purified by silica gel chromatography (0-35% EtOAc/hexanes) to yield Compound 4b (isomer b; 315 mg). LCMS (ESI): calc. $C_{31}H_{32}ClFNO_6$=573; obs. M+H=574.3. Retention time: 4.76 min.

(4b) →

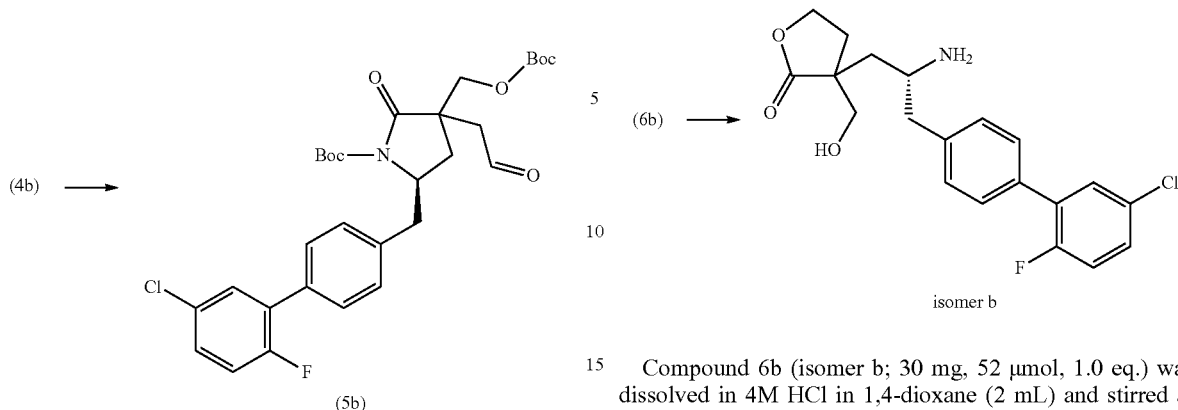

(5b)

Compound 4b (isomer b; 315 mg, 548 μmol, 1.0 eq.) was dissolved in a 3:1 1,4-dioxane/water solution (7 mL). 2,6-Lutidine (118 μL, 1097 μmol, 2.0 eq.), osmium tetroxide (2.5% in t-butanol, 56 mg, 5.5 μmol, 0.01 eq.), and sodium periodate (233 mg, 1097 μmol, 2.0 eq.) were added and the resulting mixture was stirred at room temperature for three days and when the reaction was complete (as determined by LC/MS analysis), water was added and the mixture was extracted with DCM, and the aqueous phase was discarded. The organics were concentrated to dryness and purified by silica gel chromatography (0-35% EtOAc/hexanes, 25 g CombiFlash column, 40 min.) to yield pure Compound 5b (isomer b; 243 mg). LCMS (ESI): calc. $C_{30}H_{35}ClFNO_2$=575; obs. M+H=576.0. Retention time: 4.43 min.

(5b) →

(6b)

Compound 5b (isomer b; 60 mg, 104 μmol, 1.0 eq.) was dissolved in DCM (5 mL) and MeOH (1 mL) and cooled to 0° C. for 15 minutes. NaBH$_4$ (4 mg, 105 μmol, 1.0 eq.) was added and the mixture was stirred and when complete (as determined by LC/MS analysis), the reaction was quenched with water and allowed to warm to room temperature, then extracted with DCM (3×10 mL), dried over Na$_2$SO$_4$ and concentrated to yield crude Compound 6b (isomer b; 60 mg). LCMS (ESI): calc. $C_{30}H_{32}ClFNO_2$=577; obs. M+H=578.0. Retention time: 4.28 min.

(6b) → isomer b

Compound 6b (isomer b; 30 mg, 52 μmol, 1.0 eq.) was dissolved in 4M HCl in 1,4-dioxane (2 mL) and stirred at room temperature for 3 hours and when the reaction was complete (as determined by LC/MS analysis), the mixture was concentrated in vacuo to yield the crude title compound (isomer b), which was used without further purification. LCMS (ESI): calc. $C_{20}H_{21}ClFNO_3$=377; obs. M+H=378.3. Retention time: 2.59 min.

LC/MS Method: flow rate: 1.5 mL/min; Buffer A: 0.1% TFA/H$_2$O; Buffer B 0.1% TFA/MeCN; gradient elution from 5-100% B over 3.6 minutes, then 100% B for 1.0 minute, detection at 254 nm.

Preparation 17: (R)-4-Amino-2-(2-azido-ethyl)-5-(5'-chloro-2'-fluorobiphenyl-4-yl)-2-hydroxymethyl-pentanoic Acid Compound 6b was prepared as described herein.

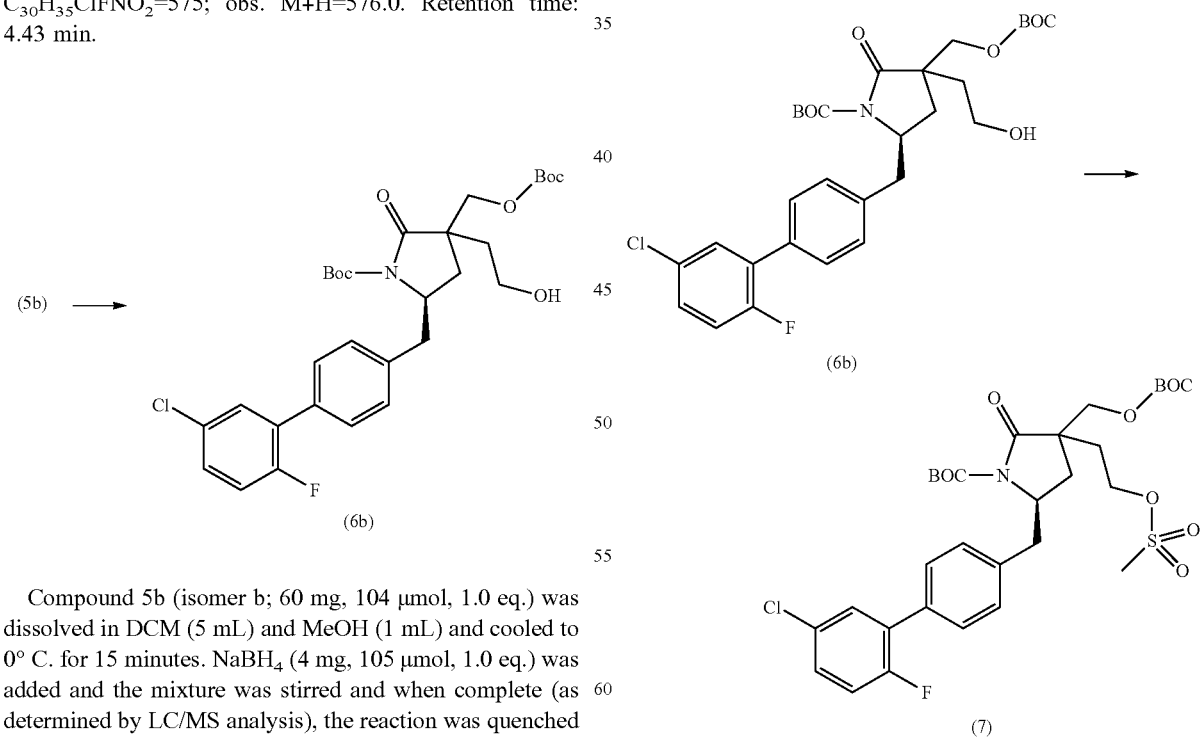

(6b)

(7)

Compound 6b (33 mg, 57 μmol, 1.0 eq.) was dissolved in DCM (1 mL) and cooled at 0° C. under nitrogen for ten minutes. Et$_3$N (16 μL, 114 μmol, 2.0 eq.) and methanesulfonyl chloride (7 μL, 86 μmol, 1.5 eq.) were added and when the reaction was complete (as determined by LC/MS analysis), the mixture was diluted with DCM (15 mL) and saturated aqueous NaHCO$_3$ (10 mL). The phases were separated and the organic phase was dried over Na$_2$SO$_4$ and concentrated in vacuo to yield crude Compound 7 (40 mg), which was used without further purification in the next step. LCMS (ESI): calc. C$_{31}$H$_{39}$ClFNO$_9$S=655; obs. M+H=656.1. Retention time: 4.31 min. (LC/MS Method 2).

(7) →

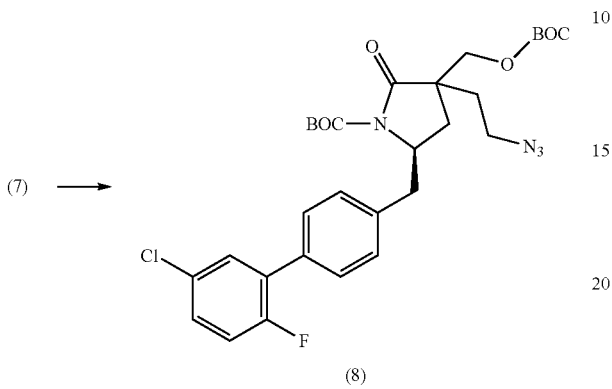

(8)

Compound 7 (40 mg, 61 μmol, 1.0 eq.) was dissolved in DMF (2 mL). Sodium azide (40 mg, 610 μmol, 10.0 eq.) was added and the resulting mixture was stirred at 55° C. for 5 hours and when the reaction was complete (as determined by LC/MS analysis), the mixture was diluted with EtOAc (15 mL) and water (10 mL). The phases were separated and the organic phase was extracted with saturated aqueous NaCl, dried over Na$_2$SO$_4$, and concentrated in vacuo to yield crude Compound 8 (30 mg). LCMS (ESI): calc. C$_{30}$H$_{36}$ClFN$_4$O$_6$=602; obs. M+H=603.1. Retention time: 4.61 min. (LC/MS Method 2).

(8) →

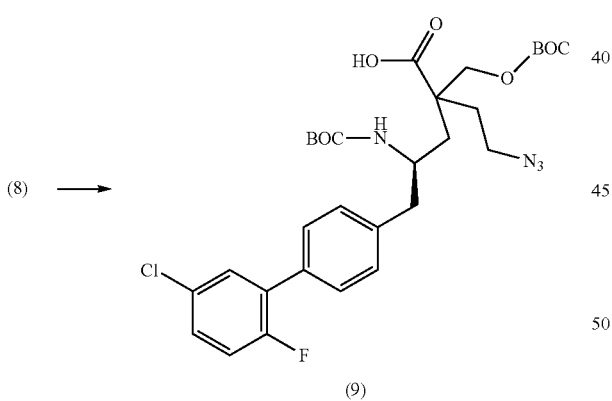

(9)

Compound 8 (30 mg, 50 μmol, 1.0 eq.) was dissolved in a 1:1 MeOH/THF solution (1.0 mL). NaOH (50 mg, 1250 μmol, 25.0 eq.) was added and the resulting solution was stirred at room temperature for 3 hours and when the reaction was complete (as determined by LC/MS analysis), the mixture was diluted with DCM (10 mL) and water (10 mL). The pH was adjusted to 3 with 3N HCl, then the phases were separated and the aqueous phase was extracted with DCM (10 mL). The combined organic phases were dried over Na$_2$SO$_4$, filtered, and concentrated to yield crude Compound 9 (25 mg). LCMS (ESI): calc. C$_{30}$H$_{38}$ClFN$_4$O$_2$=620; obs. M+H=621.1. Retention time: 4.28 min. (LC/MS Method 2).

(9) →

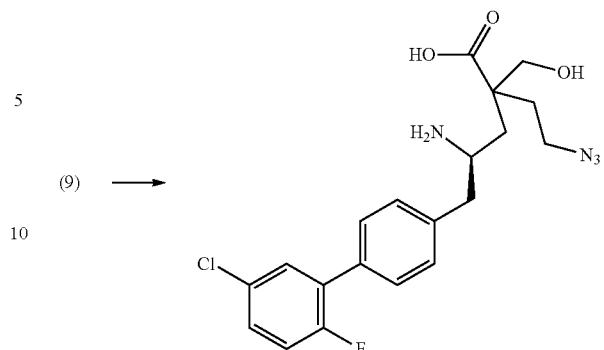

Compound 9 (25 mg) was dissolved in 4M HCl in 1,4-dioxane (2 mL), stirred at room temperature for two hours and when the reaction was complete (as determined by LC/MS analysis), the mixture concentrated to dryness to yield the crude product, which was purified by preparative HPLC to yield the title compound (10 mg). LCMS (ESI): calc. C$_{20}$H$_{22}$ClFN$_4$O$_3$=420; obs. M+H=421.0. Retention time: 4.45 min. (LC/MS Method 1).

LC/MS Method 1: flow rate: 1.5 mL/min; Buffer A: 0.1% TFA/H$_2$O; Buffer B 0.1% TFA/MeCN; gradient elution from 5%-100% B over 9.6 min, then 100% B for 1.0 minute, detection at 254 nm.

LC/MS Method 2: flow rate: 1.5 mL/min; Buffer A: 0.1% TFA/H$_2$O; Buffer B 0.1% TFA/MeCN; gradient elution from 5%-100% B over 3.6 minutes, then 100% B for 1.0 minute, detection at 254 nm.

Preparation 18: 2-[(R)-2-Amino-3-(5'-chloro-2'-fluorobiphenyl-4-yl)-propyl]-2-hydroxymethylpent-4-enoic Acid (isomers a and b)

Compounds 4a (isomer a) and 4b (isomer b) were prepared as described herein.

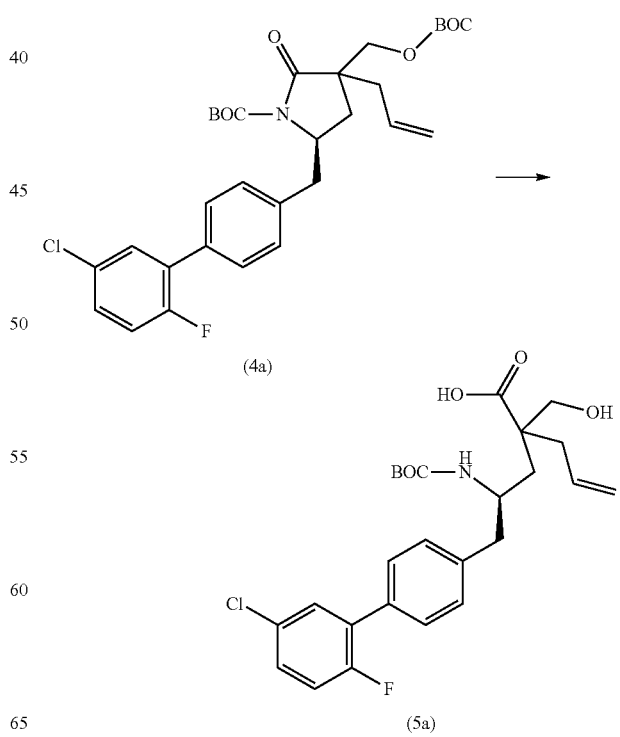

(4a)

(5a)

Compound 4a (isomer a; 100 mg, 228 µmol, 1.0 eq.) was dissolved in 1:1 THF/H$_2$O (4 mL). NaOH (175 mg, 4.4 mmol, 25.0 eq.) was added, followed by a few drops of MeOH. The mixture was stirred overnight at room temperature and concentrated to dryness to obtain crude Compound 5a (isomer a). LCMS (ESI): calc. C$_{26}$H$_{31}$ClFNO$_5$=491; obs. M+H=492.2 min. Retention time: 3.57 min.

Compound 4b (isomer b; 100 mg, 228 µmol, 1.0 eq.) was dissolved in 1:1 THF/H$_2$O (4 mL). NaOH (175 mg, 4.4 mmol, 25.0 eq.) was added, followed by a few drops of MeOH. The mixture was stirred overnight at room temperature and concentrated to dryness to obtain crude Compound 5b (isomer b). LCMS (ESI): calc. C$_{26}$H$_{31}$ClFNO$_5$=491; obs. M+H=492.2 min. Retention time: 3.61 min.

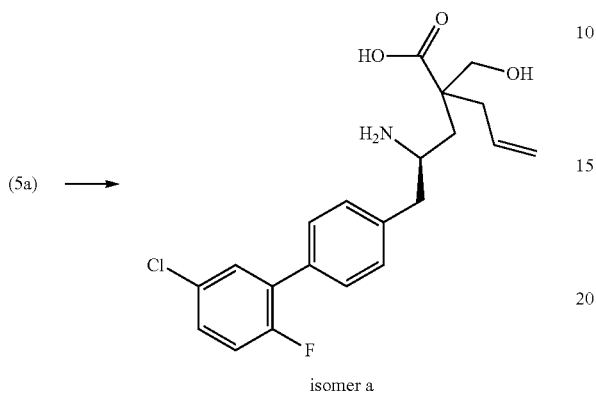

(5a) ⟶ isomer a

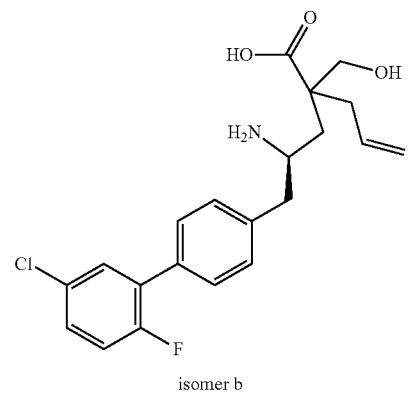

(5b) ⟶ isomer b

Compound 5a was dissolved in 4M HCl in 1,4-dioxane (5 mL), stirred at room temperature for 30 minutes and when the reaction was complete (as determined by LC/MS analysis), the mixture concentrated in vacuo and treated with water (1 mL). The mixture was once more concentrated in vacuo and dried azeotropically by evaporation with toluene to yield the crude title compound (isomer a; 85 mg), which was used without further purification. LCMS (ESI): calc. C$_{21}$H$_{23}$ClFNO$_3$=391; obs. M+H=391.9. Retention time: 2.74 min.

Compound 5b was dissolved in 4M HCl in 1,4-dioxane (5 mL), stirred at room temperature for 30 minutes and when the reaction was complete (as determined by LC/MS analysis), the mixture concentrated in vacuo and treated with water (1 mL). The mixture was once more concentrated in vacuo and dried azeotropically by evaporation with toluene to yield the crude title compound (isomer b; 60 mg), which was used without further purification. LCMS (ESI): calc. C$_{21}$H$_{23}$ClFNO$_3$=391; obs. M+H=392.0. Retention time: 4.37 min.

LC/MS Method: flow rate: 1.5 mL/min; Buffer A: 0.1% TFA/H$_2$O; Buffer B 0.1% TFA/MeCN; gradient elution from 5%-100% B over 3.6 minutes, then 100% B for 1.0 minute, detection at 254 nm.

Preparation 19: 3-[(R)-2-Amino-3-(5'-chloro-2'-fluorobiphenyl-4-yl)propyl]tetrahydrofuran-3-carboxylic Acid (isomers a and b)

Compounds 6a and 6b were prepared as described herein.

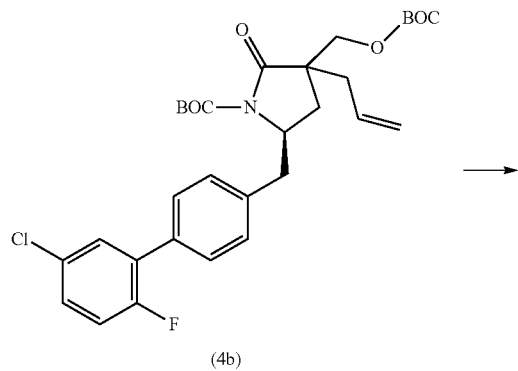

(4b)

(5b)

(6a) or (6b)

-continued

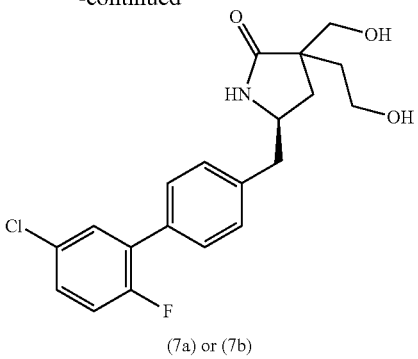

(7a) or (7b)

Compound 6a (47 mg) was dissolved in 4M HCl in 1,4-dioxane (2 mL) and stirred at room temperature for three hours. The mixture was concentrated in vacuo then treated with saturated aqueous NaHCO$_3$ (5 mL) and stirred for two hours. The mixture was extracted with DCM; the phases were separated and the aqueous phase was extracted with DCM and then discarded. The combined organics were dried in vacuo to yield crude Compound 7a (30 mg), which was used without further purification in the next step. LCMS (ESI): calc. C$_{20}$H$_{21}$ClFNO$_3$=377; obs. M+H=378.1. Retention time: 2.76 min. (LC/MS Method 2).

Compound 6b was dissolved in 4M HCl in 1,4-dioxane (2 mL) and stirred at room temperature for three hours. The mixture was concentrated in vacuo then treated with saturated aqueous NaHCO$_3$ (5 mL) and stirred for two hours. The mixture was extracted with DCM (20 mL); the phases were separated and the aqueous phase was extracted with DCM (20 mL) and then discarded. The combined organics were dried over Na$_2$SO$_4$ and dried in vacuo to yield crude Compound 7b (50 mg), which was used without further purification in the next step. LCMS (ESI): calc. C$_{20}$H$_{21}$ClFNO$_3$=377; obs. M+H=378.1. Retention time: 2.56 min. (LC/MS Method 2).

(7a) or (7b) →

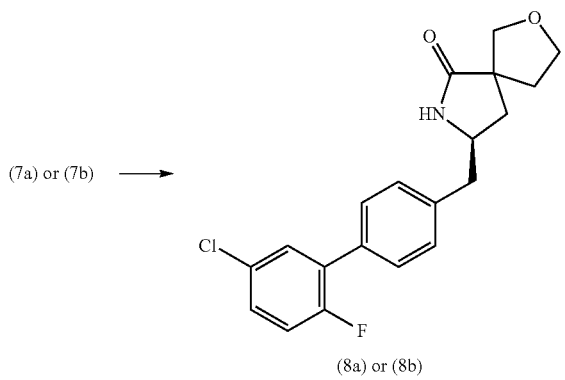 [SMILES: O=C1N[C@H](Cc2ccc(-c3cc(Cl)ccc3F)cc2)CC12CCOC2]

(8a) or (8b)

Compound 7a (50 mg, 132 μmol, 1.0 eq.) was dissolved in THF (2 mL). PPh$_3$ (87 mg, 330 μmol, 2.5 eq.) and DIAD (65 μL, 330 μmol, 2.5 eq.) were added and the resulting mixture was stirred at room temperature for 15 hours and when the reaction was complete (as determined by LC/MS analysis), the mixture was concentrated in vacuo and purified by preparative HPLC (10-30% MeCN/H$_2$O with 0.1% TFA, 40 mL/minute, 40 minutes) to yield pure Compound 8a (15 mg). LCMS (ESI): calc. C$_{20}$H$_{19}$ClFNO$_2$=359; obs. M+H=360.0. Retention time: 5.26 min. (LC/MS Method 1).

Compound 7b (50 mg, 132 μmol, 1.0 eq.) was dissolved in THF (2 mL). PPh$_3$ (87 mg, 330 μmol, 2.5 eq.) and DIAD (65 μL, 330 μmol, 2.5 eq.) were added and the resulting mixture was stirred at room temperature for 15 hours and when the reaction was complete (as determined by LC/MS analysis), the mixture was concentrated in vacuo and purified by preparative HPLC (10-30% MeCN/H$_2$O with 0.1% TFA, 40 mL/minute, 40 minutes) to yield pure Compound 8b (15 mg). LCMS (ESI): calc. C$_{20}$H$_{19}$ClFNO$_2$=359; obs. M+H=360.0. Retention time: 5.26 min. (LC/MS Method 1).

(8a) or (8b) →

(9a) or (9b)

Compound 8a (15 mg, 42 μmol, 1.0 eq.) was dissolved in THF (2 mL). The solution was cooled to 0° C., then NaHMDS (1.0 M, 40 μL, 40 μmol, 1.5 eq.) was added and the resulting mixture was stirred at 0° C. for 15 minutes. (BOC)$_2$O (9 mg, 40 μmol, 1.0 eq.) was added and the resulting solution was stirred at room temperature for 15 hours and when the reaction was complete (as determined by LC/MS analysis), the mixture was diluted with EtOAc (10 mL) and extracted with saturated aqueous NaHCO$_3$. The organic phase was dried over Na$_2$SO$_4$ and concentrated to yield crude Compound 9a. LCMS (ESI): calc. C$_{25}$H$_{22}$ClFNO$_4$=459; obs. M+H=459.9. Retention time: 4.06 min. (LC/MS Method 2).

Compound 8b (15 mg, 42 μmol, 1.0 eq.) was dissolved in THF (2 mL). The solution was cooled to 0° C., then NaHMDS (1.0 M, 40 μL, 40 μmol, 1.5 eq.) was added and the resulting mixture was stirred at 0° C. for 15 minutes. (BOC)$_2$O (9 mg, 40 μmol, 1.0 eq.) was added and the resulting solution was stirred at room temperature for 15 hours and when the reaction was complete (as determined by LC/MS analysis), the mixture was diluted with EtOAc (10 mL) and extracted with saturated aqueous NaHCO$_3$. The organic phase was dried over Na$_2$SO$_4$ and concentrated to yield crude Compound 9b. LCMS (ESI): calc. C$_{25}$H$_{22}$ClFNO$_4$=459; obs. M+H=459.9. Retention time: 4.06 min. (LC/MS Method 2).

(9a) or (9b) →

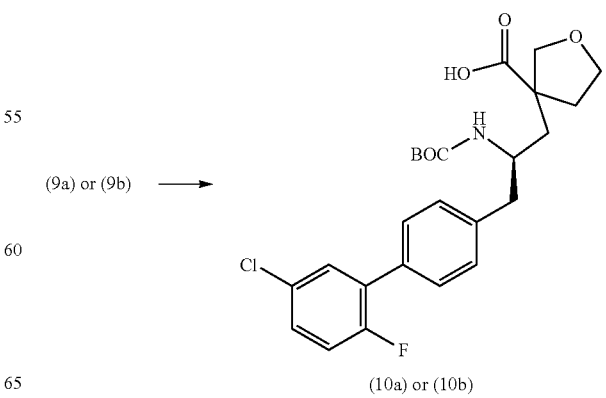

(10a) or (10b)

Compound 9a (42 µmol, 1.0 eq.) was dissolved in THF (1 mL). A 6N NaOH solution (1 mL 6 mmol) was added as well as a few drops of MeOH. The solution was stirred overnight at room temperature and when the reaction was complete (as determined by LC/MS analysis), the mixture was concentrated to dryness to yield crude Compound 10a (19 mg). LCMS (ESI): calc. $C_{25}H_{29}ClFNO_5$=477; obs. M+H=477.9. Retention time: 3.59 min. (LC/MS Method 2).

Compound 9b (42 µmol, 1.0 eq.) was dissolved in THF (1 mL). A 6N NaOH solution (1 mL 6 mmol) was added as well as a few drops of MeOH. The solution was stirred overnight at room temperature and when the reaction was complete (as determined by LC/MS analysis), the mixture was concentrated to dryness to obtain crude Compound 10b (19 mg). LCMS (ESI): calc. $C_{25}H_{29}ClFNO_5$=477; obs. M+H=477.9. Retention time: 3.59 min. (LC/MS Method 2).

(10a) or (10b) ⟶

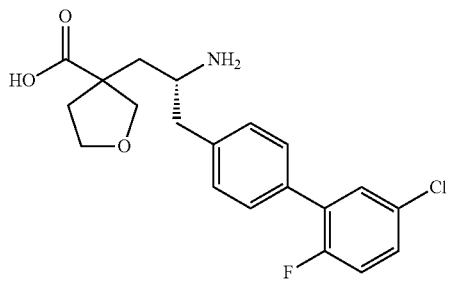

Compound 10a (19 mg) was dissolved in 4M HCl in 1,4-dioxane (2 mL), stirred at room temperature for two hours, and when the reaction was complete (as determined by LC/MS analysis), the mixture was concentrated to dryness to yield the crude title compound (isomer a; HCl salt; 10 mg), which was used without further purification. LCMS (ESI): calc. $C_{20}H_{21}ClFNO_3$=377; obs. M+H=378.0. Retention time: 2.61 min. (LC/MS Method 2).

Compound 10b (19 mg) was dissolved in 4M HCl in 1,4-dioxane (2 mL), stirred at room temperature for two hours, and when the reaction was complete (as determined by LC/MS analysis), the mixture was concentrated to dryness to yield the crude title compound (isomer b; HCl salt; 10 mg), which was used without further purification. LCMS (ESI): calc. $C_{20}H_{21}ClFNO_3$=377; obs. M+H=378.0. Retention time: 2.61 min. (LC/MS Method 2).

LC/MS Method 1: flow rate: 1.5 mL/min; Buffer A: 0.1% TFA/H$_2$O; Buffer B 0.1% TFA/MeCN; gradient elution from 5-100% B over 9.6 min, then 100% B for 1.0 minute, detection at 254 nm.

LC/MS Method 2: flow rate: 1.5 mL/min; Buffer A: 0.1% TFA/H$_2$O; Buffer B 0.1% TFA/MeCN gradient elution from 5-100% B over 3.6 minutes, then 100% B for 1.0 minute, detection at 254 nm.

Preparation 20: 3-[(R)-2-Amino-3-(5'-chloro-2'-fluorobiphenyl-4-yl)propyl]pyrrolidine-1,3-dicarboxylic Acid 1-Benzyl Ester (isomers a and b)

Compound 6a was prepared as described herein.

Compound 6a (85 mg, 147 µmol, 1.0 eq.) was dissolved in DCM (3 mL) and cooled to 0° C. under nitrogen for ten minutes. Et$_3$N (20 µL, 144 µmol, 1.0 eq.) and methanesulfonyl chloride (12 µL, 155 µmol, 1.1 eq.) were added and when the reaction was complete (as determined by LC/MS analysis), the mixture was diluted with DCM (15 mL) and saturated aqueous NaHCO$_3$ (10 mL). The phases were separated and the aqueous phase was extracted with additional DCM (15 mL), then discarded. The organic phase was dried over Na$_2$SO$_4$ and concentrated in vacuo to yield crude Compound 7a (123 mg), which was used without further purification in the next step. LCMS (ESI): calc. $C_{31}H_{39}ClFNO_9S$=655; obs. M+H=656.0. Retention time: 4.33 min.

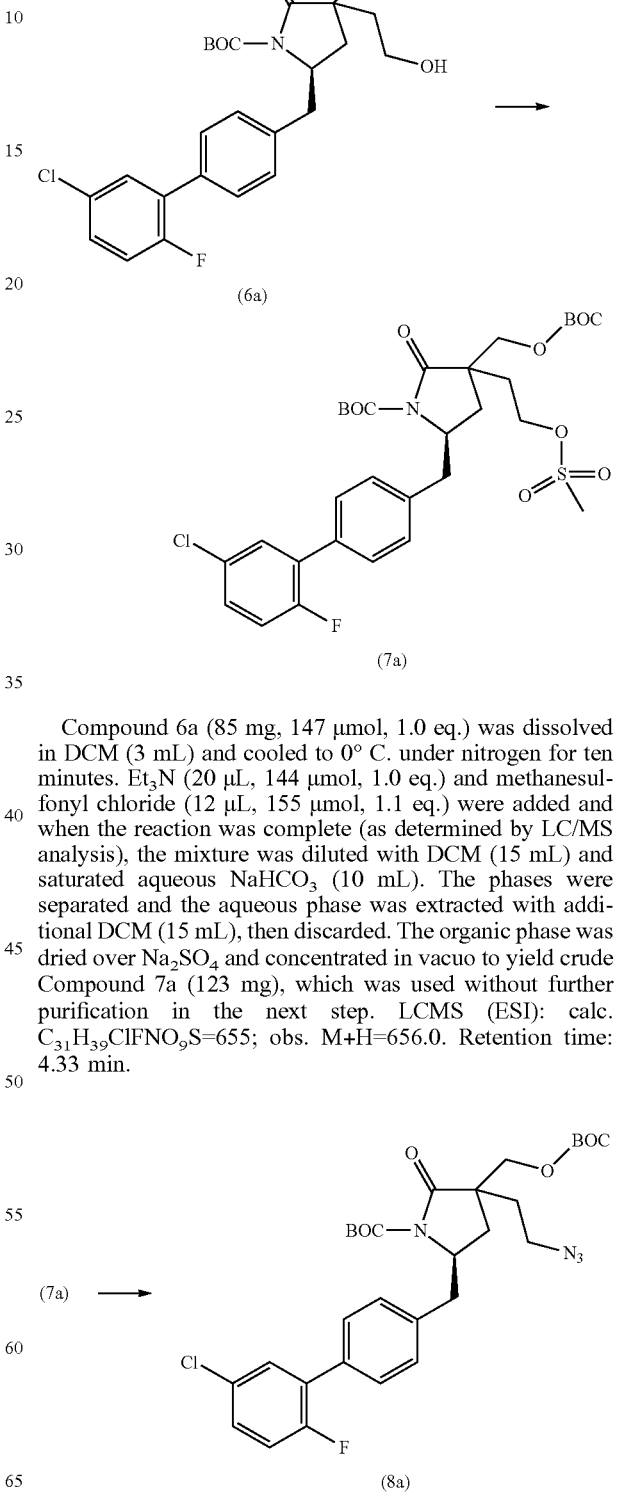

Compound 7a (123 mg, 147 μmol, 1.0 eq.) was dissolved in DMF (2 mL). Sodium azide (96 mg, 1480 μmol, 10.0 eq.) was added and the resulting mixture was stirred at 55° C. under nitrogen for two hours. The mixture was then cooled to room temperature and diluted with EtOAc (20 mL) and water (10 mL). The phases were separated and the organic phase was extracted with water (2×10 mL), dried over Na$_2$SO$_4$, and concentrated in vacuo to yield crude Compound 8a (83 mg). LCMS (ESI): calc. C$_{30}$H$_{36}$ClFN$_4$O$_6$=602; obs. M+H=602.8. Retention time: 4.62 min.

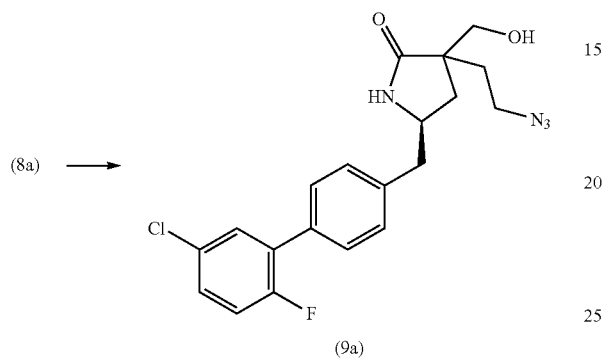

Compound 8a was dissolved in 4M HCl in 1,4-dioxane (2 mL) stirred at room temperature for two hours. The mixture was concentrated in vacuo to obtain crude Compound 9a as the hydrochloride salt (40 mg), which was used without further purification in the next step. LCMS (ESI): calc. C$_{20}$H$_{20}$ClFN$_4$O$_2$=402; obs. M+H=403.4. Retention time: 3.24 min.

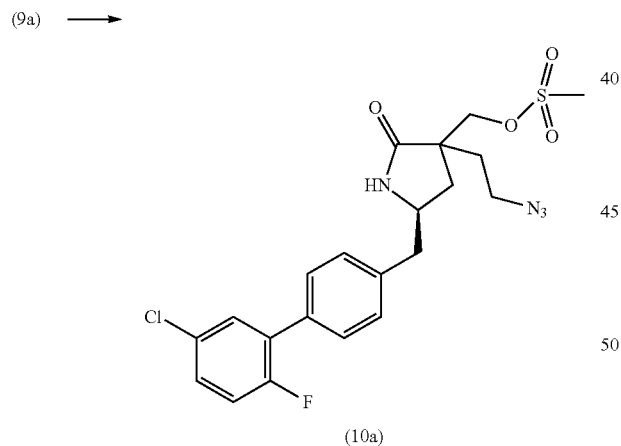

Compound 9a (40 mg, 100 μmol, 1.0 eq.) was dissolved in DCM (2 mL) and cooled to 0° C. under nitrogen. Et$_3$N (15 μL, 100 μmol, 1.0 eq.) and methanesulfonyl chloride (10 μL, 100 μmol, 1.0 eq.) were added and when the reaction was complete (as determined by LC/MS analysis), the mixture was diluted with DCM (10 mL) and saturated aqueous NaHCO$_3$ (5 mL). The phases were separated and the organic phase was dried over Na$_2$SO$_4$ and concentrated in vacuo to yield crude Compound 10a (53 mg), which was used without further purification in the next step. LCMS (ESI): calc. C$_{21}$H$_{22}$ClFN$_4$O$_4$S=480; obs. M+H=480.9. Retention time: 3.50 min.

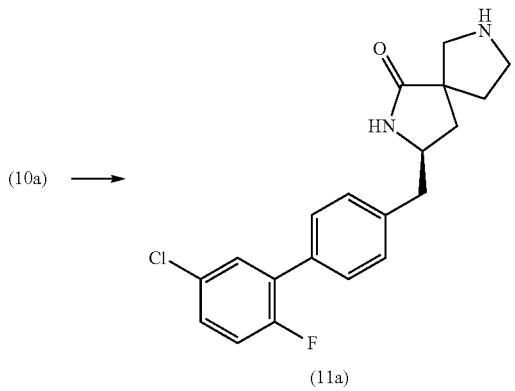 [SMILES: O=C1N[C@H](Cc2ccc(-c3cc(Cl)ccc3F)cc2)CC12CCNC2]

Compound 10a (53 mg) was dissolved in a mixture of EtOAc (2 mL) and MeOH (0.5 mL). A few drops of AcOH were also added. Pd/C (5% w/w, 10 mg) was added, and the resulting mixture stirred under 1 atmosphere of hydrogen for four hours. Et$_3$N (2 drops) was added and the mixture was purged with nitrogen and stirred for one hour, then filtered through a pad of Celite®. The pad was washed with MeOH (20 mL) and the combined filtrates were concentrated in vacuo, dissolved in toluene (10 mL), once more concentrated in vacuo, then purified by preparative HPLC 30-60% MeCN/water with 0.1% TFA) to yield Compound 11a (35 mg). LCMS (ESI): calc. C$_{20}$H$_{20}$ClFN$_2$O=358; obs. M+H=359.1. Retention time: 2.64 min.

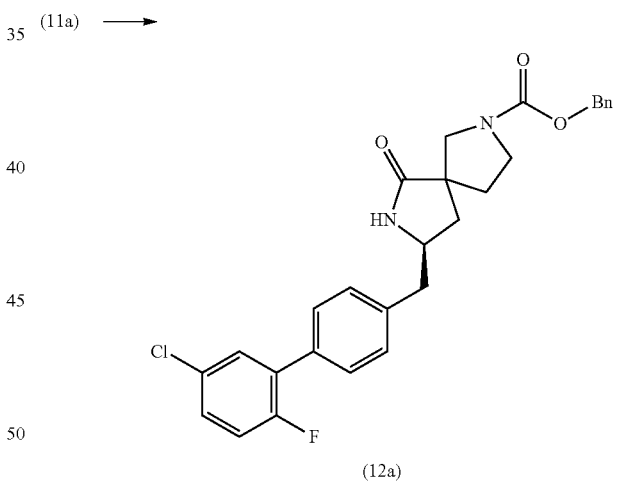

Compound 11a (15 mg, 40 μmol, 1.0 eq.) was dissolved in THF (2.0 mL). The solution was cooled to 0° C. for ten minutes, then Et$_3$N (9 μL, 120 μmol, 3 eq.) and benzyloxycarbonyl chloride (6 mg, 35 μmol, 0.9 eq.) were added and the resulting mixture was stirred at room temperature for one hour and when complete (as determined by LC/MS analysis), the reaction was quenched with saturated aqueous NaHCO$_3$ (10 mL) and extracted with EtOAc (20 mL). The organic phase was washed with saturated aqueous NaCl, dried over Na$_2$SO$_4$ and concentrated to yield crude Compound 12a (17 mg). LCMS (ESI): calc. C$_{28}$H$_{26}$ClFN$_2$O$_3$=492; obs. M+H=493.2. Retention time: 3.78 min.

(12a) →

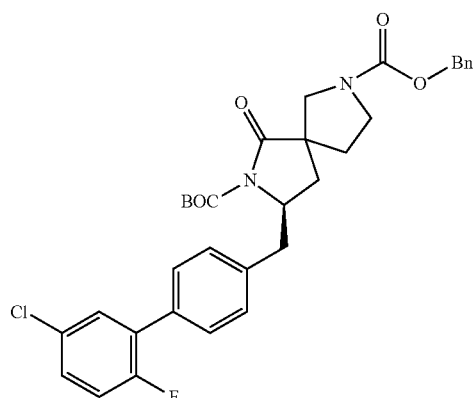

(13a)

(14a) →

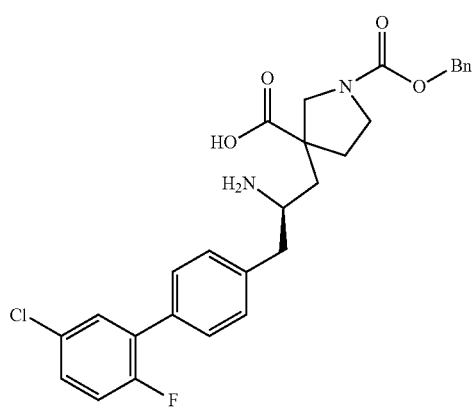

isomer a

Compound 12a (17 mg, 35 μmol, 1.0 eq.) was dissolved in THF (0.5 mL). The solution was cooled to −40° C., NaHMDS (1.0 M, 50 μL, 50 μmol, 1.4 eq.) was added, followed by (BOC)₂O (11 mg, 50 μmol, 1.4 eq.). The resulting solution was stirred at room temperature and LC/MS analysis revealed a mixture of desired product and hydrolyzed lactam. The reaction was quenched with two drops of water and concentrated to yield crude Compound 13a. LCMS (ESI): calc. $C_{33}H_{34}ClFN_2O_5$=592; obs. M+H=493.2 (M+H-Boc). Retention time: 3.89 min.

(13a) →

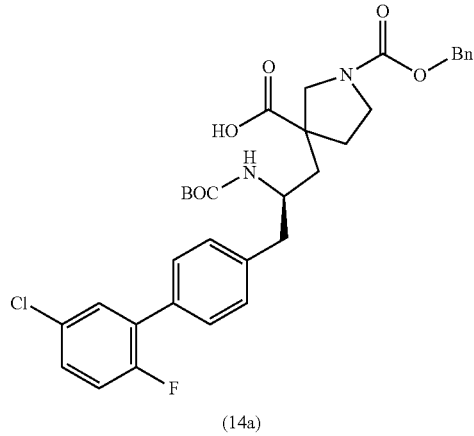

(14a)

Compound 13a (35 μmol, 1.0 eq.) was dissolved in THF (0.5 mL). 4N NaOH (50 μL, 200 μmol, 5.7 eq.) was added, followed by a few drops of MeOH. The mixture was stirred for 20 minutes at room temperature and when the reaction was complete (as determined by LC/MS analysis), the pH was adjusted to 4 with aqueous citric acid, and the mixture was extracted with DCM (2×10 mL). The phases were separated and the aqueous layer was extracted once more with DCM (10 mL). The combined organics were dried over Na₂SO₄, filtered, and concentrated to obtain crude Compound 14a (16 mg). LCMS (ESI): calc. $C_{33}H_{36}ClFN_2O_6$=610; obs. M+H=611.4 min. Retention time: 3.54 min.

Compound 14a was dissolved in 4M HCl in 1,4-dioxane (1 mL) and stirred at room temperature and when the reaction was complete (as determined by LC/MS analysis), the mixture was concentrated in vacuo to obtain the crude title compound (isomer a; 14 mg), which was used without further purification. LCMS (ESI): calc. $C_{28}H_{28}ClFN_2O_4$=510; obs. M+H=511.0. Retention time: 2.66 min.

Compound 6b was prepared as described herein.

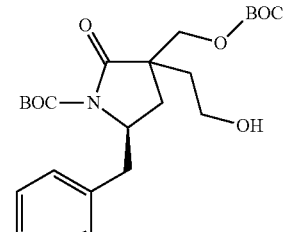

(6b)

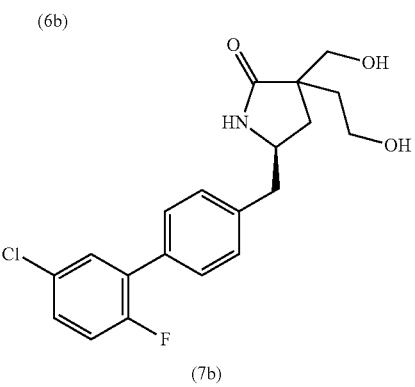

(7b)

Compound 6b (400 mg, 693 μmol, 1.0 eq.) was dissolved in 4M HCl in p-dioxane (10 mL) and stirred at room temperature for three hours. The mixture was concentrated in vacuo then dissolved in 1:1 DCM: saturated aqueous NaHCO₃ and stirred overnight. The organic phase was separated and dried over Na₂SO₄, then concentrated in vacuo to yield crude Compound 7b (251 mg), which was used without further purification in the next step. LCMS (ESI): calc. $C_{20}H_{21}ClFNO_3$=377; obs. M+H=378.2. Retention time: 2.82 min.

(7b) ⟶

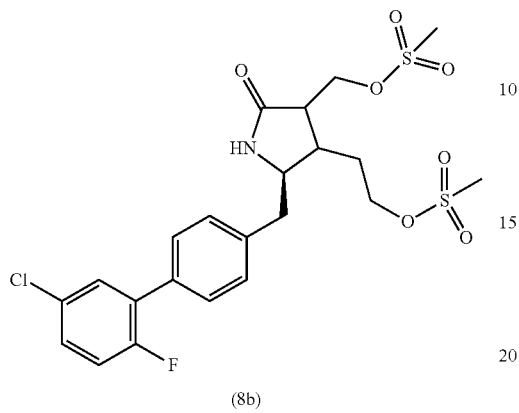

(8b)

Compound 7b (250 mg, 663 μmol, 1.0 eq.) was dissolved in DCM (10 mL) and cooled to 0° C. under nitrogen for ten minutes. $Et_3N$ (190 μL, 1360 μmol, 2.0 eq.) and methanesulfonyl chloride (110 μL, 1330 μmol, 2.0 eq.) were added and when the reaction was complete (as determined by LC/MS analysis), the mixture was diluted with DCM (10 mL) and saturated aqueous $NaHCO_3$ (5 mL). The phases were separated and the organic phase was dried over $Na_2SO_4$ and concentrated in vacuo to yield crude Compound 8b (380 mg), which was used without further purification in the next step. LCMS (ESI): calc. $C_{22}H_{25}ClFNO_2S_2$=533; obs. M+H=534.1. Retention time: 3.34 min.

(8b) ⟶

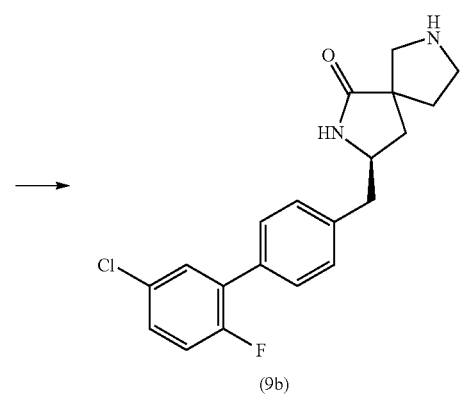

(9b)

Compound 8b (380 mg, 700 μmol, 1.0 eq.) was dissolved in DMF (5 mL). Sodium azide (463 mg, 7120 μmol, 10.0 eq.) was added and the resulting mixture was stirred at 55° C. under nitrogen for four hours. The mixture was then cooled to room temperature and diluted with EtOAc (20 mL) and water (10 mL). The phases were separated and the organic phase was dried over $Na_2SO_4$, and concentrated in vacuo. LCMS (ESI): calc. $C_{20}H_{20}ClFN_2O$=480; obs. M+H=481.8. Retention time: 3.54 min. (LC/MS Method 2). The residue was dissolved in a mixture of EtOAc (4 mL) and MeOH (1.0 mL). A few drops of AcOH were also added. Pd/C (5% w/w, 30 mg) was added, and the resulting mixture stirred under hydrogen (1 atm) for four hours. $Et_3N$ (2 drops) was added and the mixture was purged with nitrogen and stirred for one hour, then filtered through a pad of Celite®. The pad was washed with MeOH and the combined filtrates were concentrated in vacuo, dissolved in toluene, once more concentrated in vacuo, then purified by preparative HPLC (30-60% MeCN/water with 0.1% TFA) to yield Compound 9b (150 mg). LCMS (ESI): calc. $C_{20}H_{20}ClFN_2O$=358; obs. M+H=359.0. Retention time: 2.62 min.

(9b) ⟶

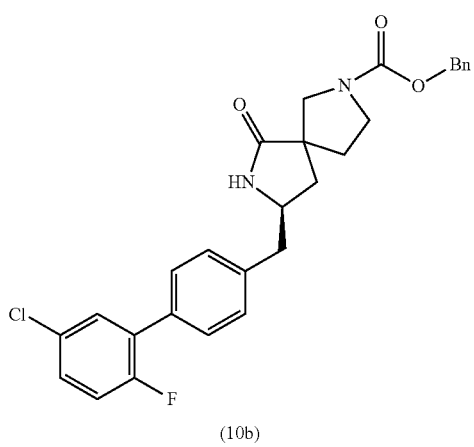

(10b)

Compound 9b (150 mg, 420 μmol, 1.0 eq.) was dissolved in THF (4.0 mL). The solution was cooled to 0° C., then $Et_3N$ (90 μL, 630 μmol, 1.5 eq.) and benzyloxycarbonyl chloride (76 μL, 500 μmol, 1.2 eq.) were added and the resulting mixture was stirred at room temperature for one hour and when complete (as determined by LC/MS analysis), the reaction was quenched with saturated aqueous $NaHCO_3$ (10 mL)) and extracted with EtOAc (20 mL). The organic phase was washed with saturated aqueous NaCl, dried over $Na_2SO_4$, filtered, and concentrated to yield crude Compound 10b (180 mg). LCMS (ESI): calc. $C_{28}H_{26}ClFN_2O_3$=492; obs. M+H=493.1. Retention time: 3.80 min.

(10b) ⟶

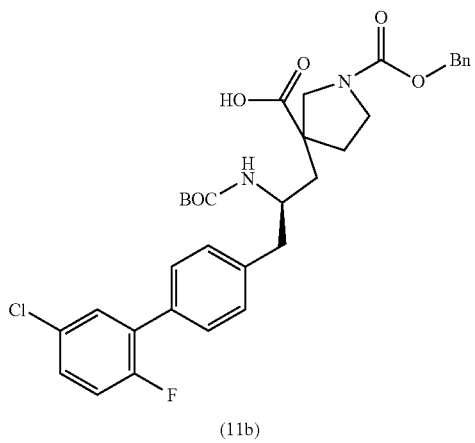

(11b)

Compound 10b (180 mg, 366 μmol, 1.0 eq.) was dissolved in THF (5 mL). The solution was cooled to −10° C., NaHMDS (1.0 M, 730 μL, 730 μmol, 2.0 eq.) was added, followed by (BOC)₂O (160 mg, 730 μmol, 2.0 eq.) and the resulting solution was stirred at room temperature for three hours. NaOH (100 mg, 2.5 mmol, 6.8 eq.) and one drop of water were added and the mixture stirred for fifteen hours at room temperature and when the reaction was complete (as determined by LC/MS analysis), the mixture was diluted with water (5 mL) and acidified to pH ~5 with HCl. The solution was extracted with DCM and the organic phase was dried over Na₂SO₄, filtered, and concentrated to yield Compound 11b (200 mg). LCMS (ESI): calc. $C_{33}H_{36}ClFN_2O_6$=610; obs. M+H=611.3. Retention time: 4.01 min.

(11b) ⟶

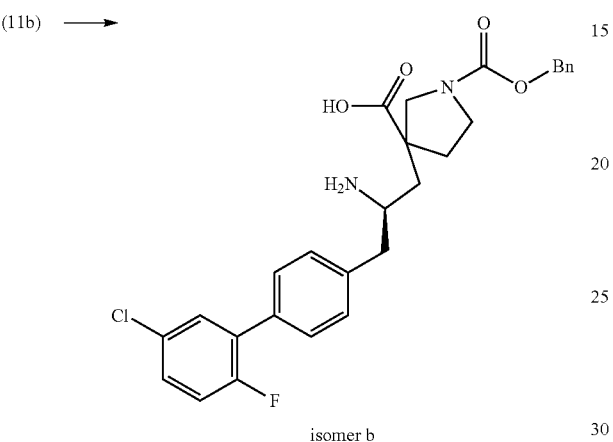

isomer b

Compound 11b (200 mg, 366 μmol, 1.0 eq.) was dissolved in 4M HCl in 1,4-dioxane (4 mL) and stirred at room temperature for two hours and when the reaction was complete (as determined by LC/MS analysis), the mixture was concentrated in vacuo to yield the crude title compound as the hydrochloride salt (isomer b; 170 mg), which was used without further purification. LCMS (ESI): calc. $C_{28}H_{28}ClFN_2O_4$=510; obs. M+H=511.3. Retention time: 3.08 min.

LC/MS Method: flow rate: 1.5 mL/min; Buffer A: 0.1% TFA/H₂O; Buffer B 0.1% TFA/MeCN; gradient elution from 5-100% B over 3.6 minutes, then 100% B for 1.0 minute, detection at 254 nm.

Preparation 21: 1-Acetyl-3-[(R)-2-amino-3-(5'-chloro-2'-fluorobiphenyl-4-yl)propyl]pyrrolidine-3-carboxylic Acid (isomers a and b)

Compound 11a was prepared as described herein.

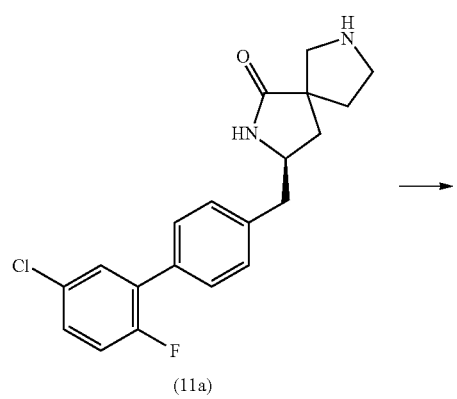

(11a)

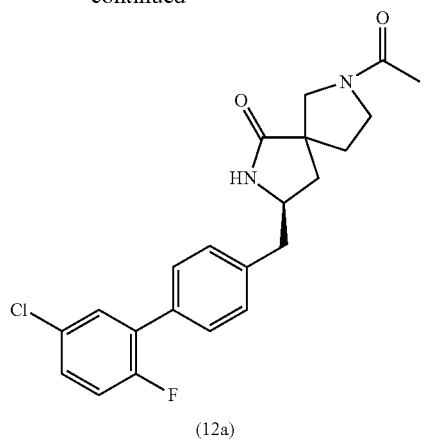

(12a)

Compound 11a (10 mg, 28 μmol, 1.0 eq.) was dissolved in DCM (2.0 mL). The solution was cooled to 0° C., then Et₃N (6 μL, 42 μmol, 1.5 equiv.) and acetic anhydride (3 μL, 31 μmol, 1.2 equiv.) were added and the resulting mixture was stirred at room temperature for 15 minutes and when complete (as determined by LC/MS analysis), the reaction was quenched with saturated aqueous NaHCO₃ (2 mL) and extracted with DCM (15 mL). The organic phase was dried over Na₂SO₄ and concentrated to yield crude Compound 12a (15 mg). LCMS (ESI): calc. $C_{22}H_{22}ClFN_2O_2$=400; obs. M+H=401.2. Retention time: 3.07 min.

(12a) ⟶

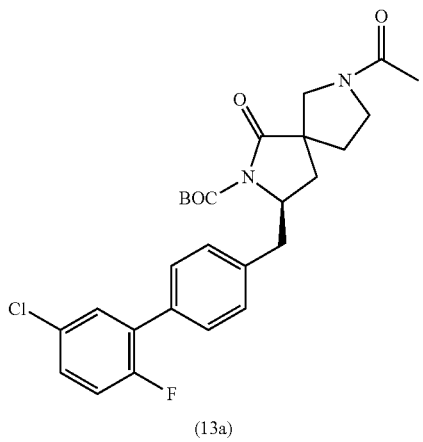

(13a)

Compound 12a (15 mg, 110 μmol, 1.0 eq.) was dissolved in THF (2.0 mL). The solution was cooled to 0° C., NaHMDS (1.0M, 150 μL, 150 μmol, 1.4 equiv.) was added, and the resulting mixture was stirred for 15 minutes at 0° C., then (BOC)₂O (22 mg, 100 μmol, 0.9 equiv.) was added and the resulting solution was stirred at room temperature and LC/MS analysis revealed a mixture of desired product and hydrolyzed lactam. The reaction was quenched with two drops of water and concentrated to yield crude Compound 13a (20 mg). LCMS (ESI): calc. $C_{27}H_{30}ClFN_2O_4$=500; obs. M+H=501.2. Retention time: 3.75 min.

(13a) → 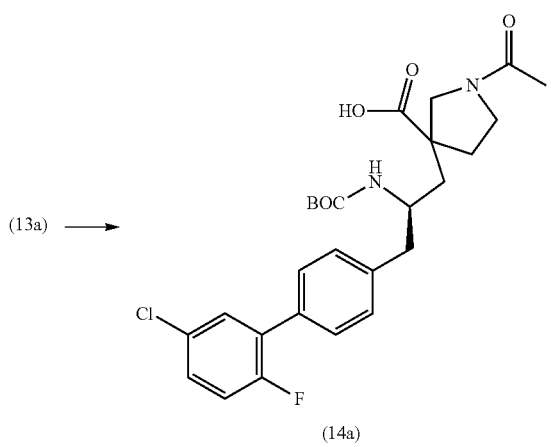 [SMILES: CC(=O)N1CCC(C[C@@H](Cc2ccc(-c3cc(Cl)ccc3F)cc2)NC(=O)OC(C)(C)C)(C(=O)O)C1]
(14a)

Compound 9b was prepared as described herein.

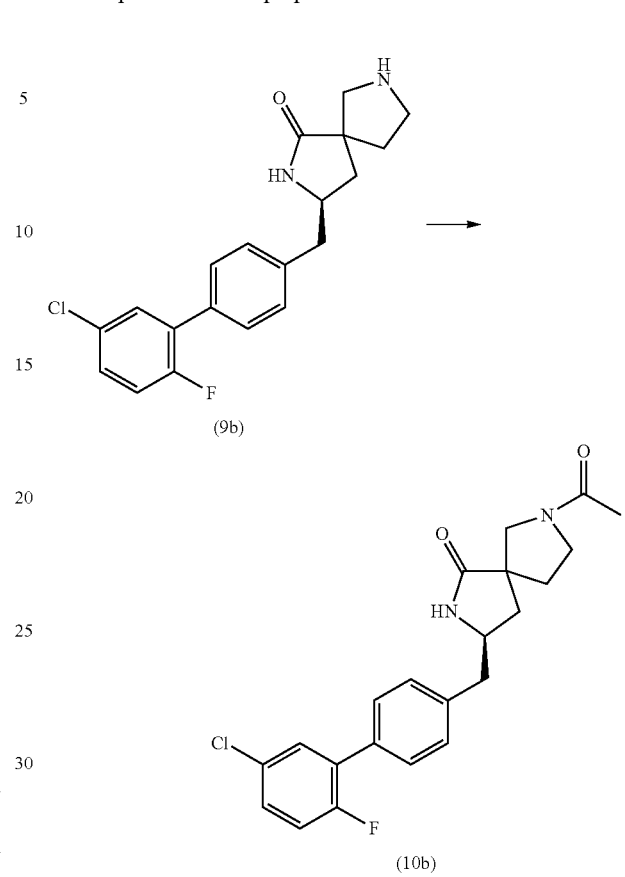

Compound 13a (20 mg, 40 µmol, 1.0 eq.) was dissolved in 1:1 THF/H₂O (2 mL). NaOH (50 mg, 1250 µmol, 31 eq.) was added, followed by a few drops of MeOH. The mixture was stirred for one hour at room temperature and when the reaction was complete (as determined by LC/MS analysis), the mixture was diluted with water (10 mL) and DCM (10 mL), then the pH was adjusted to 3 with 3N HCl. The phases were separated and the aqueous layer was extracted once more with DCM (10 mL). The combined organics were dried over Na₂SO₄, filtered, and concentrated to obtain crude Compound 14a (15 mg). LCMS (ESI): calc. $C_{27}H_{32}ClFN_2O_5$=518; obs. M+H=519.1 min. Retention time: 3.29 min.

Compound 9b (45 mg, 125 µmol, 1.0 eq.) was dissolved in DCM (2.0 mL). The solution was cooled to 0° C., then Et₃N (25 µL, 150 µmol, 1.2 equiv.) and acetic anhydride (25 µL, 190 µmol, 1.5 equiv.) were added and the resulting mixture was stirred at room temperature for 15 minutes and when complete (as determined by LC/MS analysis), the reaction was quenched with saturated aqueous NaHCO₃ (2 mL) and extracted with DCM (15 mL). The organic phase was dried over Na₂SO₄ and concentrated to yield crude Compound 10b (45 mg). LCMS (ESI): calc. $C_{22}H_{22}ClFN_2O_2$=400; obs. M+H=401.3. Retention time: 3.04 min.

(14a) → 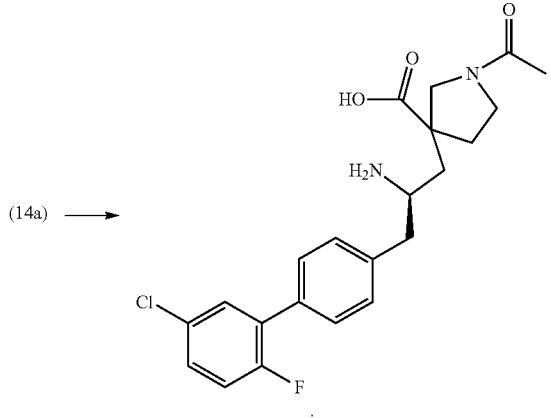
isomer a (10a) → 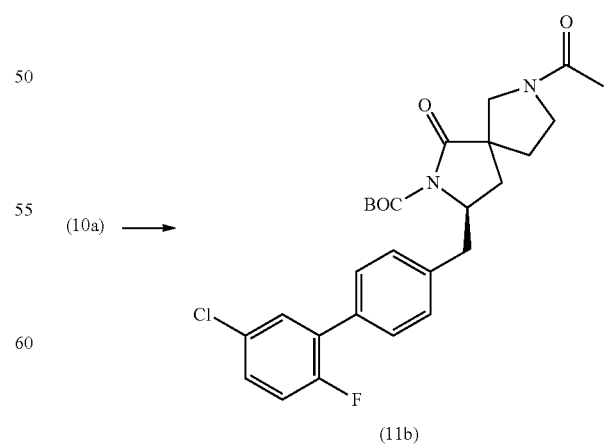
(11b)

Compound 14a was dissolved in 4M HCl in 1,4-dioxane (1 mL) and stirred at room temperature and when the reaction was complete (as determined by LC/MS analysis), the mixture was concentrated in vacuo to yield the crude title compound (isomer a; 10 mg), which was used without further purification. LCMS (ESI): calc. $C_{22}H_{24}ClFN_2O_3$=418; obs. M+H=419.1. Retention time: 2.41 min.

Compound 10b (45 mg, 110 µmol, 1.0 eq.) was dissolved in THF (2.0 mL). The solution was cooled to 0° C., then NaHMDS (1.0M, 150 μL, 150 μmol, 1.5 equiv.) was added and the resulting mixture was stirred for 15 minutes at 0° C., then (BOC)$_2$O (22 mg, 100 μmol, 0.9 equiv.) was added and the resulting solution was stirred at room temperature for 30 minutes and LC/MS analysis revealed a mixture of desired product and hydrolyzed lactam. The reaction was quenched with two drops of water and concentrated to yield crude Compound 11b. LCMS (ESI): calc. $C_{22}H_{30}ClFN_2O_4$=500; obs. M+H=501.2. Retention time: 3.71 min.

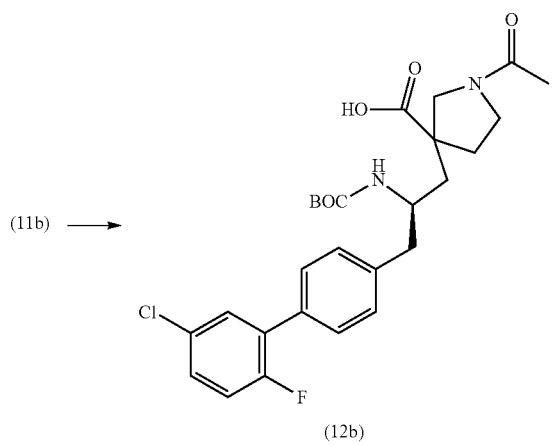 [SMILES: CC(=O)N1CCC(C[C@@H](Cc2ccc(-c3cc(Cl)ccc3F)cc2)NC(=O)OC(C)(C)C)(C(=O)O)C1]

(11b) →

(12b)

Compound 11b (110 μmol, 1.0 eq.) was dissolved in 1:1 THF/H$_2$O (2 mL). NaOH (50 mg, 1250 μmol, 31 eq.) was added, followed by a few drops of MeOH. The mixture was stirred for one hour at room temperature and when the reaction was complete (as determined by LC/MS analysis), the mixture was diluted with water (10 mL) and DCM (10 mL), then the pH was adjusted to 3 with 3N HCl. The phases were separated and the aqueous layer was extracted once more with DCM (10 mL). The combined organics were dried over Na$_2$SO$_4$, filtered, and concentrated to yield crude Compound 12b (40 mg). LCMS (ESI): calc. $C_{22}H_{32}ClFN_2O_5$=518; obs. M+H=519.1 min. Retention time: 3.32 min.

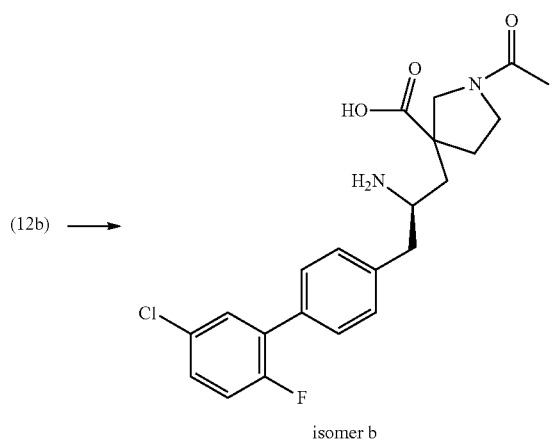 [SMILES: CC(=O)N1CCC(C[C@H](N)Cc2ccc(-c3cc(Cl)ccc3F)cc2)(C(=O)O)C1]

(12b) → isomer b

Compound 12b (40 mg, 77 μmol, 1.0 eq.) was dissolved in 4M HCl in 1,4-dioxane (4 mL) and stirred at room temperature for two hours and when the reaction was complete (as determined by LC/MS analysis), the mixture was concentrated in vacuo to yield the crude title compound (isomer b; 40 mg) as the hydrochloride salt, which was used without further purification. LCMS (ESI): calc. $C_{22}H_{24}ClFN_2O_3$=418; obs. M+H=419.1. Retention time: 2.47 min.

LC/MS Method: flow rate: 1.5 mL/min; Buffer A: 0.1% TFA/H$_2$O; Buffer B 0.1% TFA/MeCN; gradient elution from 5-100% B over 3.6 minutes, then 100% B for 1.0 minute, detection at 254 nm.

Preparation 22: [(R)-3-Acetylamino-1-(4-bromobenzyl)-3-t-butylcarbamoylbutyl]carbamic Acid t-Butyl Ester

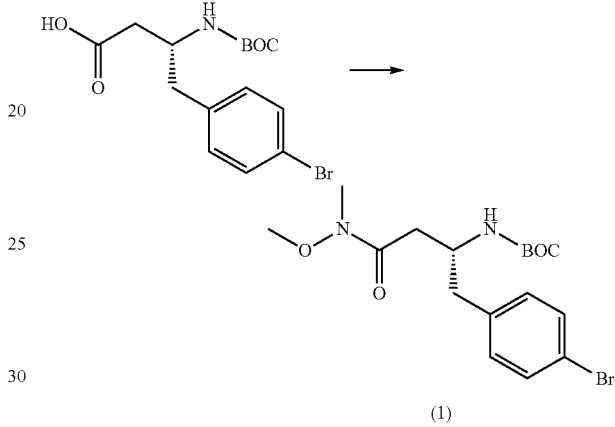

(1)

4-methylmorpholine (645 μL, 5.9 mmol) and isobutyl chloroformate (0.8 mL, 6.1 mmol) were added to a stirred solution of (R)-4-(4-bromophenyl)-3-t-butoxycarbonylaminobutyric acid (2 g, 5.6 mmol) in THF (31.0 mL) at 0° C., forming a white precipitate. To this was added a solution of Et$_3$N (934 μL, 6.7 mmol) and N,O-dimethylhydroxylamine hydrochloride (654 mg, 6.7 mmol) in DMF (2.3 mL), which had been filtered. The resulting mixture was stirred at 0° C. for 2 hours. The mixture was then filtered and concentrated. The residue was diluted with EtOAc (30 mL) and washed with saturated aqueous NaHCO$_3$ (10 mL) and saturated aqueous NaCl (10 mL). The organic layer was dried over Na$_2$SO$_4$, filtered, and concentrated in vacuo to afford a clear oil. This crude residue was purified by flash chromatography (EtOAc:hexanes, 0-50%) to yield Compound 1 as white crystals (1.3 g).

(1) → 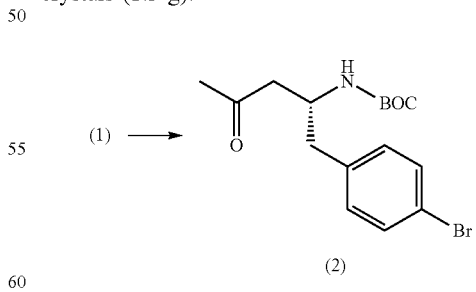

(2)

Methyllithium (2.7 mL, 2.7 mmol) (1-2 M in Et$_2$O) was added to a stirred solution of Compound 1 (550 mg, 1.4 mmol) in Et$_2$O (15 mL) at 0° C. The reaction was determined to be complete after 3 hours and was quenched with saturated aqueous NH$_4$Cl (4 mL). Et$_2$O (60 mL) was added and the mixture was washed with 1M aqueous HCl (15 mL)

and saturated aqueous NaCl (15 mL). The organic layer was dried, filtered, and concentrated in vacuo to yield Compound 2 (474 mg, 97% yield) as a white solid.

(2) →

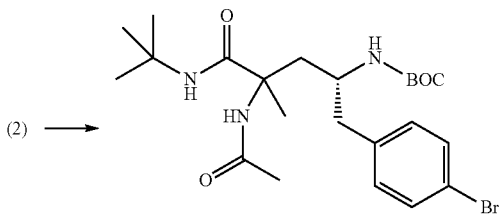 [SMILES: CC(=O)NC(C)(C[C@@H](Cc1ccc(Br)cc1)NC(=O)OC(C)(C)C)C(=O)NC(C)(C)C]

t-Butyl isocyanide (208 μL, 1.8 mmol) was added to a stirred solution of ammonium acetate (212 mg, 2.8 mmol) and Compound 2 (327 mg, 918 μmol) in 2,2,2-trifluoroethanol (2 mL, 918 μmol) at room temperature under an atmosphere of nitrogen. The reaction was determined to be complete after 14 hours. Water (10 mL) was added and the mixture was extracted with EtOAc (2×10 mL). The organic layers were combined and washed with saturated aqueous NaCl (10 mL), dried over MgSO$_4$, filtered, and concentrated in vacuo to yield the title compound (444 mg, 97% yield) as a white solid.

Preparation 23: (R)-t-Butyl 4-((5'-chloro-2'-fluoro-[1,1'-biphenyl]-4-yl)methyl)-1,2,3-oxathiazolidine-3-carboxylate 2,2-dioxide

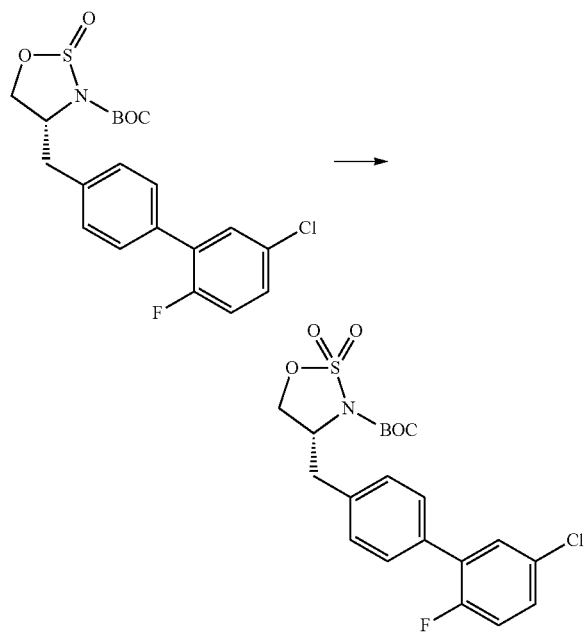

(4R)-t-Butyl 4-((5'-chloro-2'-fluoro-[1,1'-biphenyl]-4-yl) methyl)-1,2,3-oxathiazolidine-3-carboxylate 2-oxide (3.0 g, 7.0 mmol) was dissolved in MeCN to yield a clear solution. The solution was cooled to 0° C. followed by addition of ruthenium(III) chloride monohydrate (16 mg, 70 μmol) and sodium periodate (2.3 g, 10.6 mmol). Water (20 mL) was added and the mixture was vigorously stirred at 0° C. for 1 hour, yielding a thick slurry (analysis showed 10% conversion). The mixture was then stirred at 5° C. overnight (almost complete conversion was observed). Additional water (20 mL) was added and the mixture was stirred at room temperature for 1 hour. The mixture was filtered and dried to yield the crude product (3 g; purity 95%). The crude material was stirred in DCM (50 mL) for 2 hours. Fine darker solids were filtered off and the filtrate was concentrated to dryness to yield the title compound (2 g) as an off-white solid.

Example 1

(2R,4R)-2-Amino-5-(5'-chloro-2'-fluorobiphenyl-4-yl)-2-methyl-4-[(3H-[1,2,3]triazole-4-carbonyl) amino]pentanoic Acid (isomer a) and (2S,4R)-2-Amino-5-(5'-chloro-2'-fluorobiphenyl-4-O-2-methyl-4-[(3H-[1,2,3]triazole-4-carbonyl)amino]pentanoic Acid (isomer b)

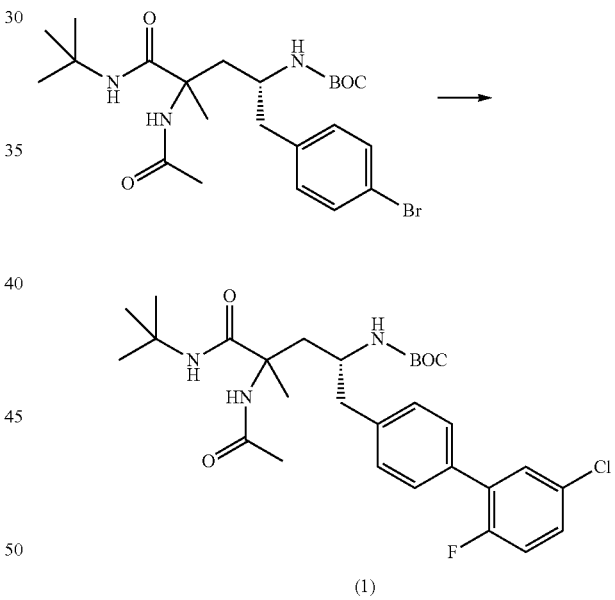

[(R)-3-Acetylamino-1-(4-bromobenzyl)-3-t-butylcarbamoylbutyl]carbamic acid t-butyl ester (160 mg, 321 μmol) and 5-chloro-2-fluorophenylboronic acid (61.6 mg, 353 μmol) were dissolved in water (0.8 mL) and EtOH (4 mL). The mixture was degassed and purged with nitrogen (3×). Pd(PPh$_3$)$_4$ (37.1 mg, 32 μmol) was added and the mixture was again degassed and purged with nitrogen (3×). The reaction flask was capped and heated at 90° C. for 1 hour. The mixture was then filtered and the filtrate concentrated in vacuo and purified by flash chromatography (pre-adsorbed onto silica; EtOAc:hexanes 40-70% to yield Compound 1 (103 mg) as a white solid.

(1) ⟶

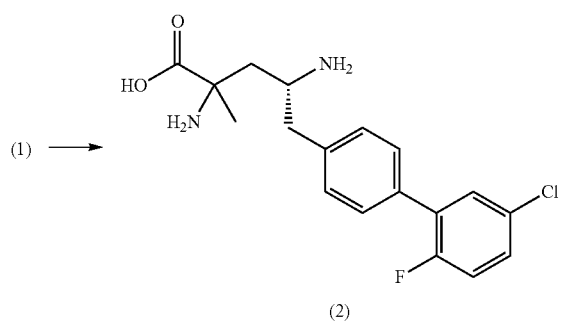 [SMILES: CC(N)(C[C@H](N)Cc1ccc(-c2cc(Cl)ccc2F)cc1)C(=O)O]

(2)

Compound 1 (103 mg, 188 μmol) was suspended in 6N HCl (2 mL, 12 mmol) and stirred at 120° C. for 72 hours. LCMS indicated that the BOC group had been cleaved and the product mixture mainly consisted of fully deprotected Compound 2, lactam (major product) and intramolecular imine (mass 405). The mixture was concentrated in vacuo and the residue mixed with 6N NaOH (2 mL) and EtOH (2 mL). After 3 hours at 120° C., the reaction was determined to be complete and the mixture was concentrated in vacuo to yield Compound 2.

(2) ⟶

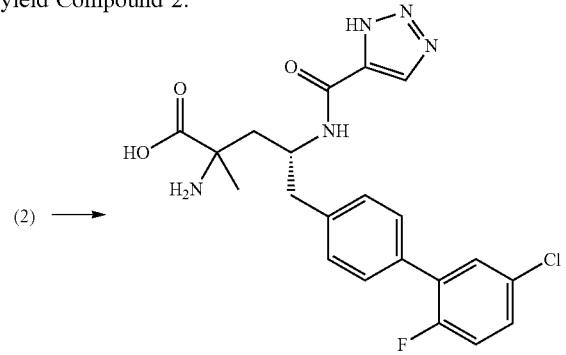

HATU (79 mg, 207 μmol) was added to a stirred solution of 1H-1,2,3-triazole-4-carboxylic acid (23 mg, 207 μmol) in DMF (1.3 mL) and stirred for 10 minutes. DIPEA (49 mg, 376 μmol) was added and after 5 minutes, Compound 2 (66 mg, 188 μmol) pre-dissolved in DMF and DIPEA (1.3 mL, 2 eq.) was added. After 90 minutes LCMS indicated the major product. The mixture was then concentrated in vacuo. The product was determined to be a mixture of the isomers with an additional impurity. The product was purified by preparative HPLC to yield the title isomer a (2.75 min retention time; 1.1 mg) and b (2.68 min retention time; 3.1 mg) as TFA salts.

Example 2

(2S,4R)-2-Aminomethyl-5-(5'-chloro-2'-fluorobiphenyl-4-O-2-methyl-4-[(3H-[1,2,3]triazole-4-carbonyl)amino]pentanoic Acid

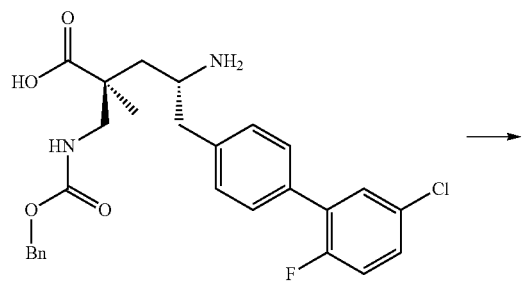

⟶

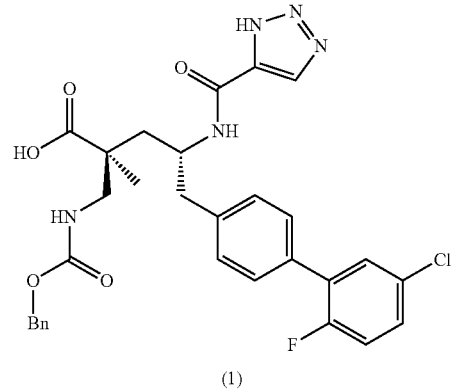

(1)

3H-[1,2,3]triazole-4-carboxylic acid (2.1 mg, 18 μmol) with HATU (7.0 mg, 18 μmol) in DMF (0.5 mL) was stirred for 10 minutes. DIPEA (4.8 μL) was added and the mixture was stirred for 1 minute. This was then added to a pre-dissolved solution of (2S,4R)-4-amino-2-(benzyloxycarbonylaminomethyl)-5-(5'-chloro-2'-fluorobiphenyl-4-yl)-2-methylpentanoic acid (11 mg, 22 μmol), DMF (1 mL), and DIPEA (9.6 μL, 55 μmol). The resulting mixture was stirred for 30 minutes. The mixture was partially concentrated under reduced pressure. The residue was purified by reverse phase chromatography to yield Compound 1 (8 mg, 73% yield).

(1) ⟶

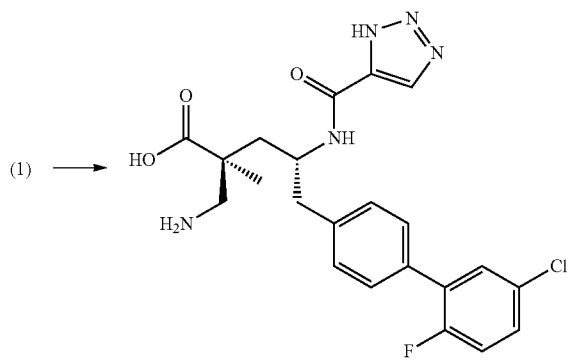 [SMILES: C[C@@](CN)(C[C@@H](Cc1ccc(-c2cc(Cl)ccc2F)cc1)NC(=O)c1cnn[nH]1)C(=O)O]

Compound 1 (8 mg, 13 μmol) was combined with Pd/C (2.9 mg, 5.4 μmol) and dissolved in EtOAc (2 mL) and AcOH (1 mL). The solution was degassed in vacuo and hydrogen was added, making sure that the solution was not exposed to air. The solution was stirred for 2 hours. The hydrogen gas was removed and the reaction flask was purged with nitrogen. The solids were filtered off and the product was purified by reverse phase to yield the title compound (5 mg, 81% yield; purity 95%) as a TFA salt. MS m/z [M+H]+ calc'd for $C_{22}H_{23}ClFN_5O_3$, 460.15. found 460.

Example 3

(2S,4R)-2-Aminomethyl-5-(5'-chloro-2'-fluorobiphenyl-4-yl)-4-[(1-difluoromethyl-1H-pyrazole-3-carbonyl)amino]-2-methylpentanoic Acid

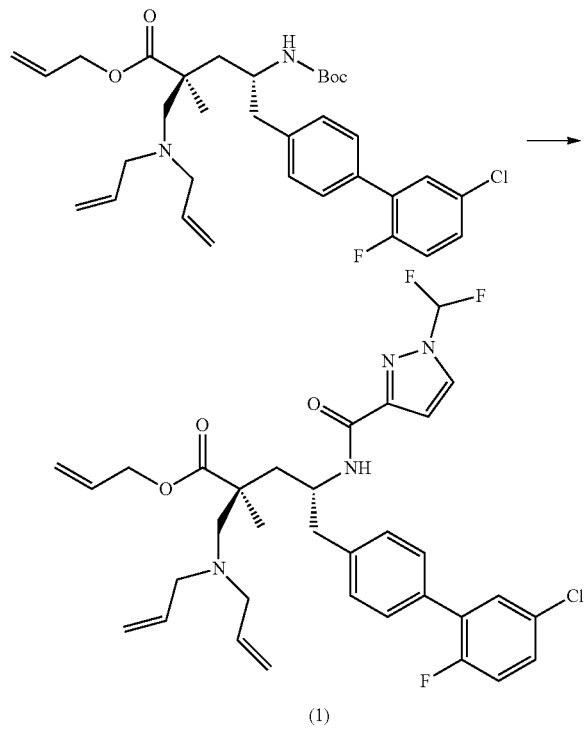

(1)

To a solution of (2S,4R)-4-t-butoxycarbonylamino-5-(5'-chloro-2'-fluoro-biphenyl-4-yl)-2-diallylaminomethyl-2-methylpentanoic acid allyl ester (16 mg, 27 µmol) in dioxane (270 µL) was added HCl (135 µL, 540 µmol). The resulting solution was stirred at room temperature for 2 hours and then concentrated in vacuo. A vial containing a solution of HATU (12 mg, 32 µmol) and 1-(difluoromethyl)-1H-pyrazole-3-carboxylic acid (5.3 mg, 32 µmol) in DMF (270 µL) was stirred at room temperature for 30 minutes. The crude material was added in DMF (270 µL), followed by DIPEA (14 µL, 81 µmol). The resulting solution was stirred at room temperature for 1 hour and then concentrated in vacuo. The crude material was purified by column chromatography (0-100% EtOAc in hexanes) to yield Compound 1 (5.9 mg, 35% yield).

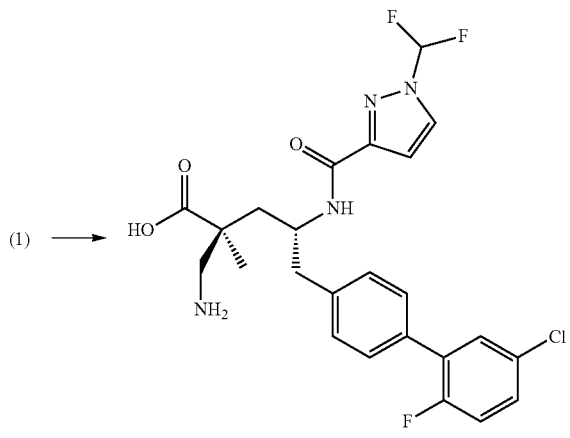 [SMILES: C[C@@](CN)(C[C@@H](Cc1ccc(-c2cc(Cl)ccc2F)cc1)NC(=O)c1ccn(C(F)F)n1)C(=O)O]

To a solution of Compound 1 (5.9 mg, 9.4 µmol) in degassed DCM (25 µL) and AcOH (5.4 µL, 94 µmol) was added Pd(PPh$_3$)$_4$ (325 µg, 0.3 µmol) and 1,3-dimethylbarbituric acid (13 mg, 84 µmol). The solution was stirred at 35° C. for 18 hours. The solution was concentrated in vacuo and purified by preparative HPLC to yield the title compound (3.0 mg, 51% yield; purity 100%) as a TFA salt. MS m/z [M+H]$^+$ calc'd for C$_{24}$H$_{24}$ClF$_3$N$_4$O$_3$, 509.15. found 509.2.

Example 4

Following the procedures described herein, and substituting the appropriate starting materials and reagents, these compounds were prepared as a TFA salt:

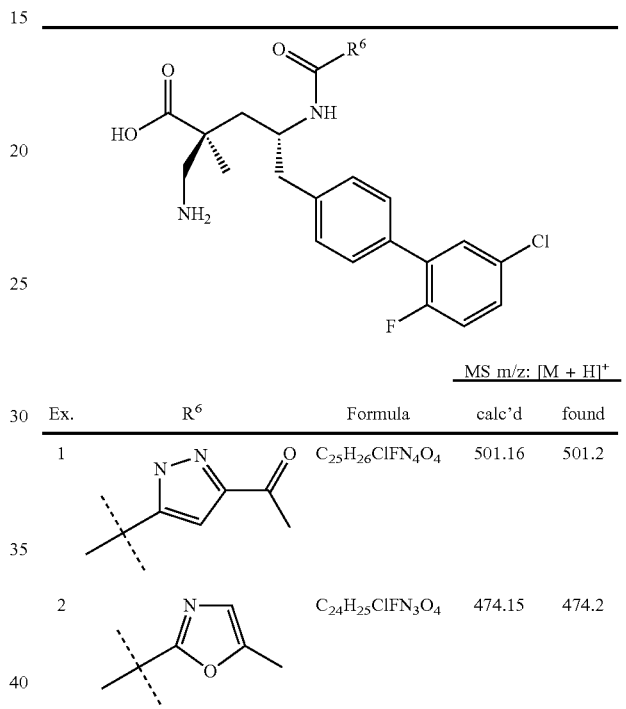

| | | | MS m/z: [M + H]$^+$ | |
|---|---|---|---|---|
| Ex. | R$^6$ | Formula | calc'd | found |
| 1 | (5-acetyl-pyrazol-3-yl) | C$_{25}$H$_{26}$ClFN$_4$O$_4$ | 501.16 | 501.2 |
| 2 | (5-methyl-oxazol-2-yl) | C$_{24}$H$_{25}$ClFN$_3$O$_4$ | 474.15 | 474.2 |

1. (2S,4R)-4-[(5-Acetyl-2H-pyrazole-3-carbonyl)-amino]-2-aminomethyl-5-(5'-chloro-2'-fluorobiphenyl-4-yl)-2-methylpentanoic acid 2. (2S,4R)-2-Aminomethyl-5-(5'-chloro-2'-fluorobiphenyl-4-yl)-2-methyl-4-[(5-methyl-oxazole-2-carbonyl)amino]pentanoic acid

Example 5

(2S,4R)-2-Carbamoyl-5-(5'-chloro-2'-fluorobiphenyl-4-yl)-2-methyl-4-[(1H-[1,2,3]triazole-4-carbonyl)amino]pentanoic Acid

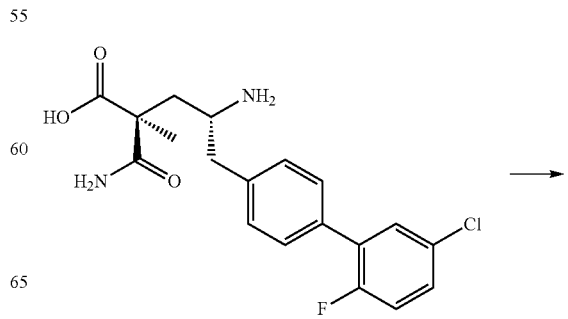

-continued

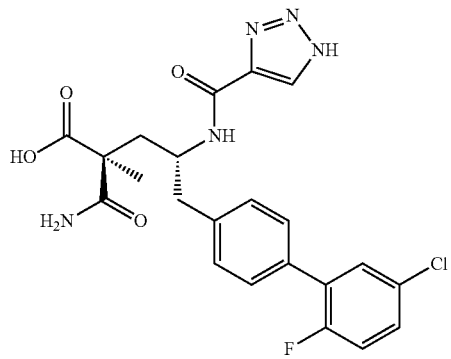

3H-[1,2,3]triazole-4-carboxylic acid (6.3 mg, 56 µmol) and HATU (21.2 mg, 56 µmol) were dissolved in DMF (2 mL) and stirred at room temperature for 15 minutes. (2S,4R)-4-Amino-2-carbamoyl-5-(5'-chloro-2'-fluorobiphenyl-4-yl)-2-methylpentanoic acid (25.3 mg, 67 µmol) and DIPEA (29 µL, 167 µmol) were added and the mixture was stirred at room temperature for 15 minutes, at which time LCMS indicated the mass of the desired compound. The mixture was concentrated in vacuo and the residue was purified by preparative HPLC to yield the title compound (7.4 mg 28% yield; purity 99%) as a TFA salt. MS m/z [M+H]$^+$ calc'd for $C_{22}H_{21}ClFN_5O_4$, 474.13. found 475.2.

Example 6

2-{(R)-3-(5'-Chloro-2'-fluorobiphenyl-4-O-2-[(1H-[1,2,3]triazole-4-carbonyl)amino]propyl}-2-methyl-malonic Acid 1H-1,2,3-triazole-4-carboxylic acid (3.3 mg, 29 µmol) and HATU (10.5 mg, 28 µmol) were dissolved in DMF (2.0 mL) and stirred for 15 minutes at room temperature. 2-[(R)-2-Amino-3-(5'-chloro-2'-fluorobiphenyl-4-yl)propyl]-2-methylmalonic acid (12.0 mg, 32 µmol) and DIPEA (9.2 µL, 53 µmol) were added, and the resulting mixture was stirred for 15 minutes at room temperature, at which time LCMS indicated the mass of the desired compound. The mixture was concentrated in vacuo and the residue was purified by preparative HPLC to yield the title compound (5 mg) as a TFA salt. MS m/z [M+H]$^+$ calc'd for $C_{22}H_{20}ClFN_4O_5$, 475.11. found 475.

Example 7

(2S,4R)-5-(5'-Chloro-2'-fluorobiphenyl-4-yl)-2-methoxymethyl-2-methyl-4-[(5-oxo-4,5-dihydro-[1,2,4]oxadiazole-3-carbonyl)amino]pentanoic Acid

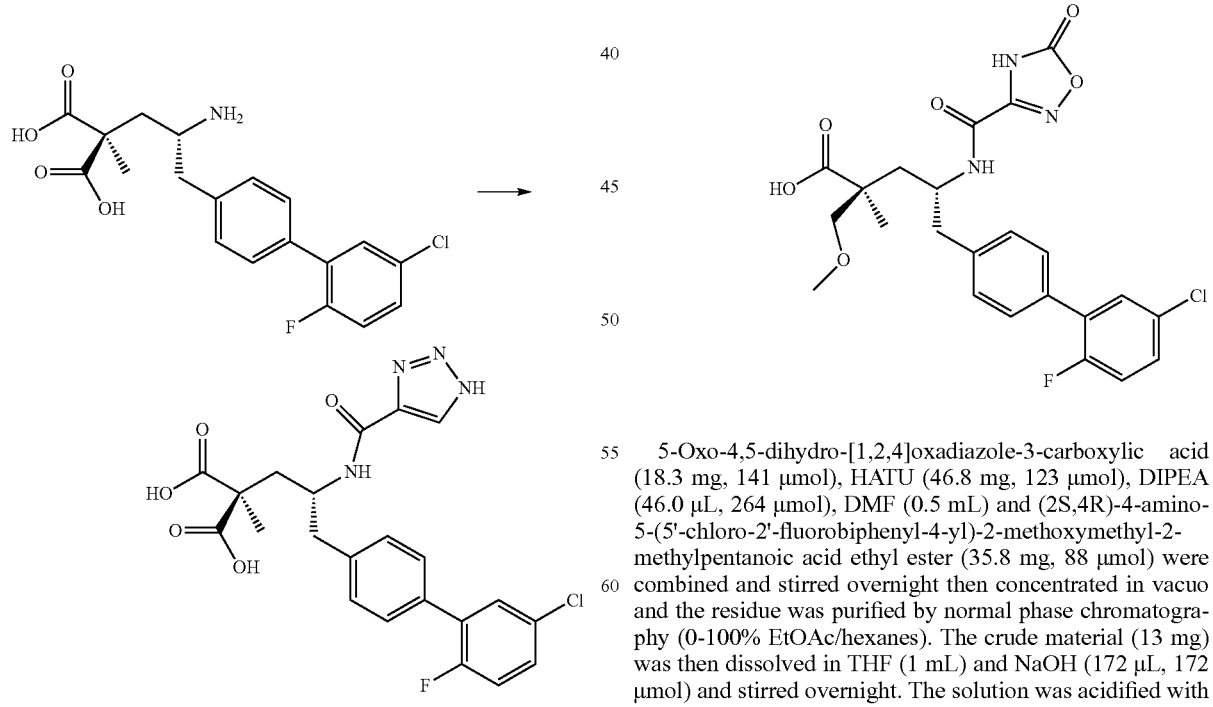

5-Oxo-4,5-dihydro-[1,2,4]oxadiazole-3-carboxylic acid (18.3 mg, 141 µmol), HATU (46.8 mg, 123 µmol), DIPEA (46.0 µL, 264 µmol), DMF (0.5 mL) and (2S,4R)-4-amino-5-(5'-chloro-2'-fluorobiphenyl-4-yl)-2-methoxymethyl-2-methylpentanoic acid ethyl ester (35.8 mg, 88 µmol) were combined and stirred overnight then concentrated in vacuo and the residue was purified by normal phase chromatography (0-100% EtOAc/hexanes). The crude material (13 mg) was then dissolved in THF (1 mL) and NaOH (172 µL, 172 µmol) and stirred overnight. The solution was acidified with AcOH and purified by reverse phase chromatography to yield the title compound (1 mg; purity 95%). MS m/z [M+H]$^+$ calc'd for $C_{23}H_{23}ClFN_3O_6$, 492.13. found 492.

Example 8

Following the procedures described herein, and substituting the appropriate starting materials and reagents, these compounds were prepared as the parent compound:

| Ex. | R⁶ | Formula | MS m/z: [M+H]⁺ calc'd | found |
|---|---|---|---|---|
| 1 | 2-methyl-5-methyloxazole | $C_{25}H_{26}ClFN_2O_5$ | 489.15 | 489.5 |
| 2 | 2-cyclopropyloxazole | $C_{27}H_{28}ClFN_2O_5$ | 515.17 | 516.0 |
| 3 | 5-chloropyridine-2-yl | $C_{26}H_{25}Cl_2FN_2O_4$ | 519.12 | 519.4 |
| 4 | pyrimidin-2-yl | $C_{25}H_{25}ClFN_3O_4$ | 486.15 | 485.9 |
| 5 | 5-trifluoromethylpyridin-2-yl | $C_{27}H_{25}ClF_4N_2O_4$ | 553.14 | 552.9 |
| 6 | oxazol-2-yl | $C_{24}H_{24}ClFN_2O_5$ | 475.14 | 475.1 |
| 7 | 1H-[1,2,4]triazol-3-yl | $C_{23}H_{24}ClFN_4O_4$ | 475.15 | 475.2 |
| 8 | 1-ethoxy-1H-[1,2,3]triazol-4-yl | $C_{25}H_{28}ClFN_4O_5$ | 519.17 | 519.2 |
| 9 | 1-methoxy-1H-[1,2,3]triazol-4-yl | $C_{24}H_{26}ClFN_4O_5$ | 505.16 | 505.2 |
| 10 | 1-(2-hydroxyethyl)-1H-[1,2,3]triazol-4-yl | $C_{25}H_{28}ClFN_4O_5$ | 519.17 | 519.2 |

1. (2S,4R)-5-(5'-Chloro-2'-fluorobiphenyl-4-yl)-2-methoxymethyl-2-methyl-4-[(5-methyloxazole-2-carbonyl)amino]pentanoic acid
2. (2S,4R)-5-(5'-Chloro-2'-fluorobiphenyl-4-yl)-4-[(2-cyclopropyloxazole-4-carbonyl)amino]-2-methoxymethyl-2-methylpentanoic acid
3. (2S,4R)-5-(5'-Chloro-2'-fluorobiphenyl-4-yl)-4-[(5-chloropyridine-2-carbonyl)amino]-2-methoxymethyl-2-methylpentanoic acid
4. (2S,4R)-5-(5'-Chloro-2'-fluorobiphenyl-4-yl)-2-methoxymethyl-2-methyl-4-[(pyrimidine-2-carbonyl)amino]pentanoic acid
5. (2S,4R)-5-(5'-Chloro-2'-fluorobiphenyl-4-yl)-2-methoxymethyl-2-methyl-4-[(5-trifluoromethylpyridine-2-carbonyl)amino]pentanoic acid
6. (2S,4R)-5-(5'-Chloro-2'-fluorobiphenyl-4-yl)-2-methoxymethyl-2-methyl-4-[(oxazole-2-carbonyl)amino]pentanoic acid
7. (2S,4R)-5-(5'-Chloro-2'-fluorobiphenyl-4-yl)-2-methoxymethyl-2-methyl-4-[(1H-[1,2,4]triazole-3-carbonyl)amino]pentanoic acid
8. (2S,4R)-5-(5'-Chloro-2'-fluorobiphenyl-4-yl)-4-[(1-ethoxy-1H-[1,2,3]triazole-4-carbonyl)amino]-2-methoxymethyl-2-methylpentanoic acid
9. (2S,4R)-5-(5'-Chloro-2'-fluorobiphenyl-4-yl)-4-[(1-methoxy-1H-[1,2,3]triazole-4-carbonyl)amino]-2-methoxymethyl-2-methylpentanoic acid
10. (2S,4R)-5-(5'-Chloro-2'-fluorobiphenyl-4-yl)-4-{[1-(2-hydroxyethyl)-1H-[1,2,3]triazole-4-carbonyl]amino}-2-methoxymethyl-2-methylpentanoic acid

Example 9

(2S,4R)-5-(3'-Chlorobiphenyl-4-O-2-ethoxymethyl-2-methyl-4-[(5-oxo-4,5-dihydro-[1,2,4]oxadiazole-3-carbonyl)amino]pentanoic Acid

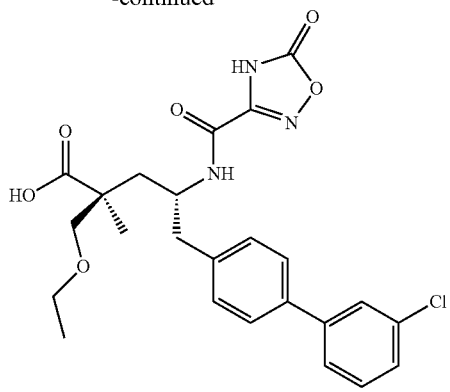

5-Oxo-4,5-dihydro-[1,2,4]oxadiazole-3-carboxylic acid (37.0 mg, 284 μmol), HATU (95 mg, 249 μmol), DIPEA (93 μL, 533 μmol), and (2S,4R)-4-amino-5-(3'-chlorobiphenyl-4-yl)-2-ethoxymethyl-2-methylpentanoic acid ethyl ester (71.8 mg, 178 μmol) were combined and stirred overnight then concentrated in vacuo and the residue was purified by normal phase chromatography. The material (39.9 mg) was then dissolved in THF (1 mL) and NaOH (387 μL, 387 μmol) and stirred overnight at 40° C. The solution was acidified with AcOH and purified by reverse phase chromatography to yield the title compound (5 mg; purity 95%). MS m/z [M+H]$^+$ calc'd for $C_{24}H_{26}ClN_3O_6$, 488.15. found 488.

Example 10

(2S,4R)-5-(5'-Chloro-2'-fluorobiphenyl-4-O-4-1(2-cyclopropyoxazole-4-carbonyl)aminol-2-ethoxymethyl-2-methylpentanoic Acid

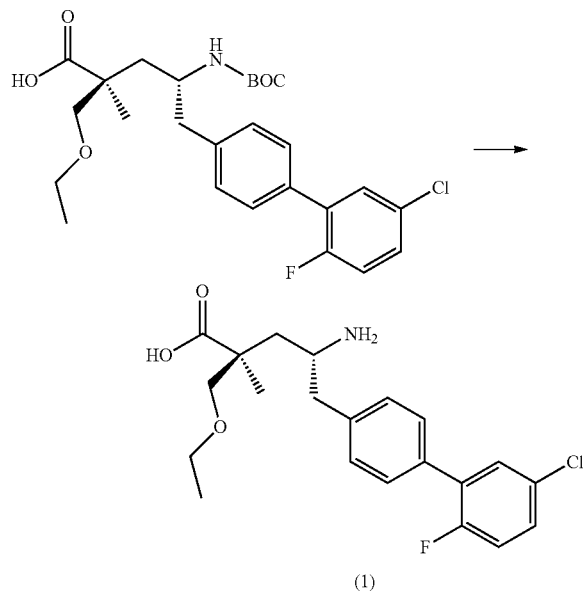

(2S,4R)-4-t-Butoxycarbonylamino-5-(5'-chloro-2'-fluoro-biphenyl-4-yl)-2-ethoxymethyl-2-methylpentanoic acid (220 mg, 445 μmol) was dissolved in MeCN (5 mL). 4N HCl in dioxane (4 mL) was added and the resulting mixture was stirred for 10 minutes then concentrated under reduced pressure to yield Compound 1, which was used directly in the next step.

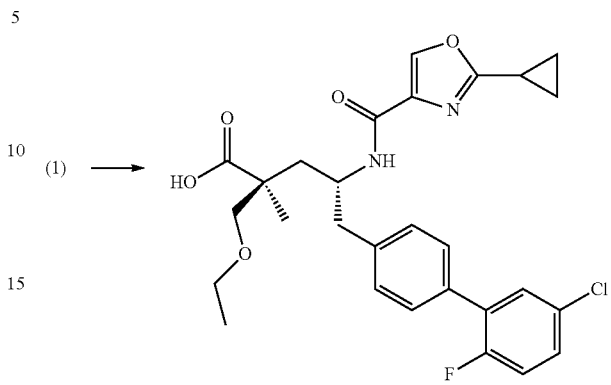

2-Cyclopropyl-oxazole-4-carboxylic acid (6.48 mg, 42 μmol) was mixed with HATU (16.1 mg, 42 μmol) in DMF (0.5 mL) and stirred for 10 minutes. DIPEA (1 eq.) was added and the mixture was stirred for 1 minute. Compound 1 (20 mg, 51 μmol) in DMF (0.5 mL) was combined with DIPEA (22.2 μL, 127 μmol) and added to the mixture and stirred for 30 minutes. Half of the solvent was evaporated under reduced pressure and the residue was purified by preparative HPLC to yield the title compound (4.1 mg; purity 100%) as an HCl salt. MS m/z [M+H]$^+$ calc'd for $C_{28}H_{30}ClFN_2O_5$, 529.18. found 530.2.

Example 11

Following the procedures described herein, and substituting the appropriate starting materials and reagents, these compounds were prepared, either as the parent compound or as a TFA salt:

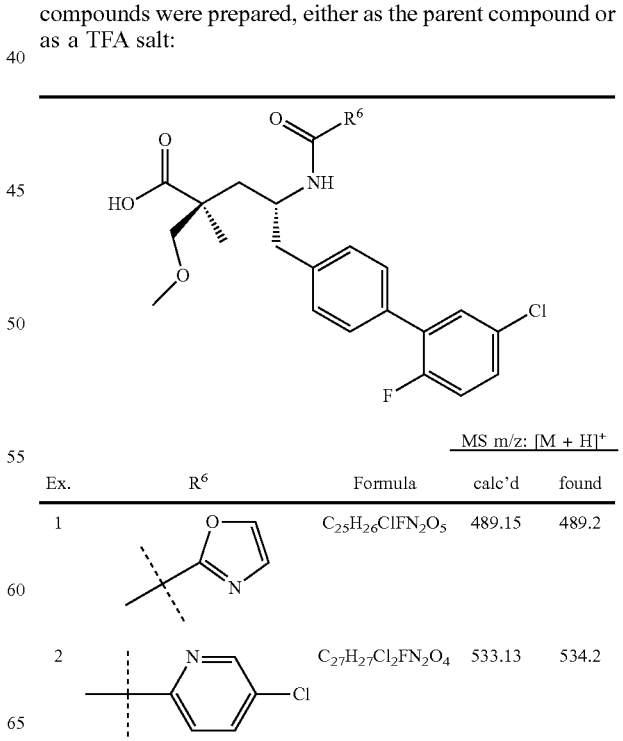

| Ex. | R$^6$ | Formula | MS m/z: [M + H]$^+$ calc'd | found |
|---|---|---|---|---|
| 1 | (oxazol-2-yl) | $C_{25}H_{26}ClFN_2O_5$ | 489.15 | 489.2 |
| 2 | (5-chloropyridin-2-yl) | $C_{27}H_{27}Cl_2FN_2O_4$ | 533.13 | 534.2 |

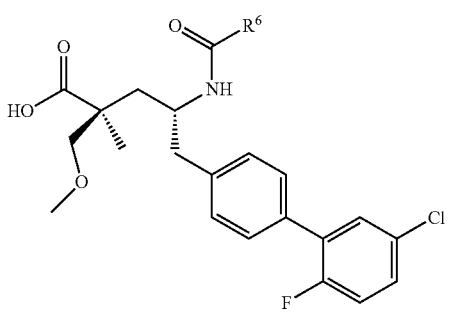

| Ex. | R⁶ | Formula | MS m/z: [M + H]⁺ calc'd | found |
|---|---|---|---|---|
| 3 | (pyrimidin-2-yl) | $C_{26}H_{27}ClFN_3O_4$ | 500.17 | 501.2 |
| 4 | (5-methyl-2H-1,2,3-triazol-4-yl) | $C_{25}H_{28}ClFN_4O_4$ | 503.18 | 503.2 |

1 (2S,4R)-5-(5'-Chloro-2'-fluorobiphenyl-4-yl)-2-ethoxymethyl-2-methyl-4-[(oxazole-2-carbonyl)amino]pentanoic acid 2 (2S,4R)-5-(5'-Chloro-2'-fluorobiphenyl-4-yl)-4-[(5-chloropyridine-2-carbonyl)amino]-2-ethoxymethyl-2-methylpentanoic acid 3 (2S,4R)-5-(5'-Chloro-2'-fluorobiphenyl-4-yl)-2-ethoxymethyl-2-methyl-4-[(pyrimidine-2-carbonyl)amino]pentanoic acid 4 (2S,4R)-5-(5'-Chloro-2'-fluorobiphenyl-4-yl)-2-ethoxymethyl-2-methyl-4-[(5-methyl-2H-[1,2,3]triazole-4-carbonyl)amino]pentanoic acid

Example 12

(R)-5-(5'-Chloro-2'-fluorobiphenyl-4-yl)-2-cyano-2-methyl-4-[(3H-[1,2,3]triazole-4-carbonyl)amino]pentanoic Acid (isomers a and b)

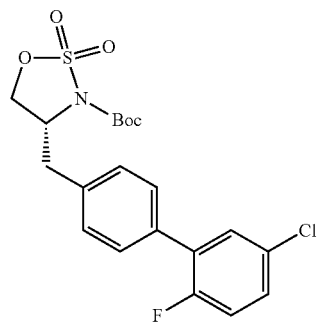

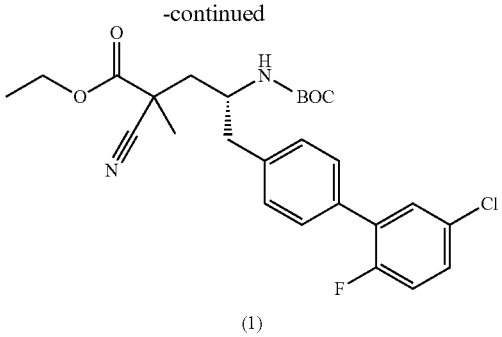

(1)

To a solution of ethyl 2-cyanopropanoate (13 μL, 0.1 mmol), (R)-t-butyl 4-((5'-chloro-2'-fluoro-[1,1'-biphenyl]-4-yl)methyl)-1,2,3-oxathiazolidine-3-carboxylate 2,2-dioxide (46 mg, 105 μmol) and tetrabutylammonium bromide (3.2 mg, 10.0 μmol) in xylene (0.5 ml) was added Cs₂CO₃ (49 mg, 150 μmol). The resulting mixture was stirred at room temperature overnight. 1N HCl (0.5 mL) was added and the solution was stirred at room temperature for 10 minutes. DCM (1.5 mL) was added, the layers were separated and the aqueous layer was extracted with DCM (2×1.5 mL). The combined organic layers were dried over Na₂SO₄, filtered and concentrated. The crude product was purified by column chromatography (0-30% EtOAc in hexanes over 20 minutes) to yield Compound 1 (33.8 mg, 69% yield) as a clear oil.

(1) →

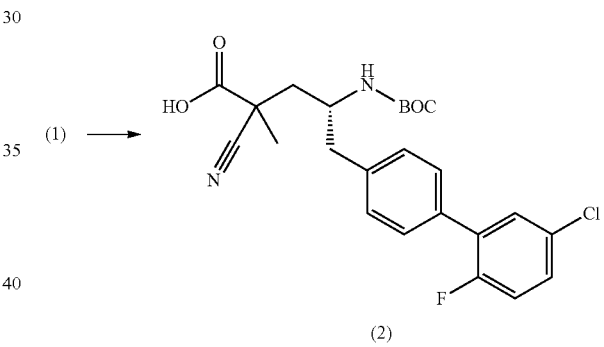

(2)

To a solution of Compound 1 (33.8 mg, 69 μmol) in EtOH (690 μL) was added NaOH (553 μL, 553 μmol). The solution was stirred at room temperature for 2 hours and then concentrated in vacuo to yield Compound 2, which was used without further purification.

(2) →

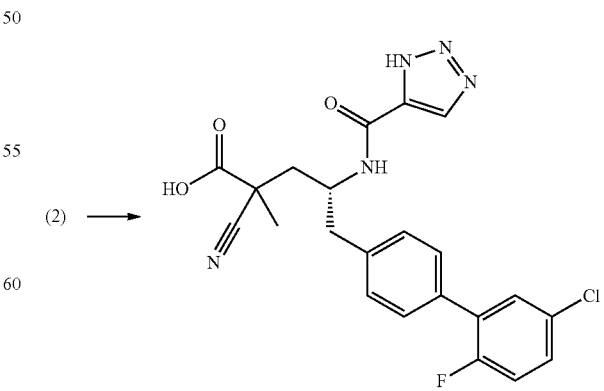

A solution of Compound 2 (31.8 mg, 69 μmol) in HCl (345 μL, 1.4 mmol) was stirred at room temperature for 1 hour. Once the BOC group had been cleaved, the reaction mixture was concentrated in vacuo. A solution of 3H-[1,2,3]triazole-4-carboxylic acid (9.4 mg, 83 μmol) and HATU (31.5 mg, 83 μmol) in DMF (690 μL) were stirred at room temperature for 30 minutes. After this time, a solution of the crude amine in DMF (690 μL) was added, followed by DIPEA (36 μL, 207 μmol). After stirring at room temperature for 2 hours, the solution was concentrated in vacuo. The crude residue was purified by preparative HPLC to yield the title compound isomer a (1.6 mg; purity 82%) and isomer b (0.7 mg; purity 100%). MS m/z [M+H]$^+$ calc'd for $C_{22}H_{19}ClFN_5O_3$, 456.12. found 456.2.

Example 13

(R)-5-(5'-Chloro-2'-fluorobiphenyl-4-yl)-2-cyano-2-methyl-4-[(3H-[1,2,3]triazole-4-carbonyl)amino]pentanoic Acid Ethyl Ester (isomers a, b, and c)

Compound 1 was prepared as described herein.

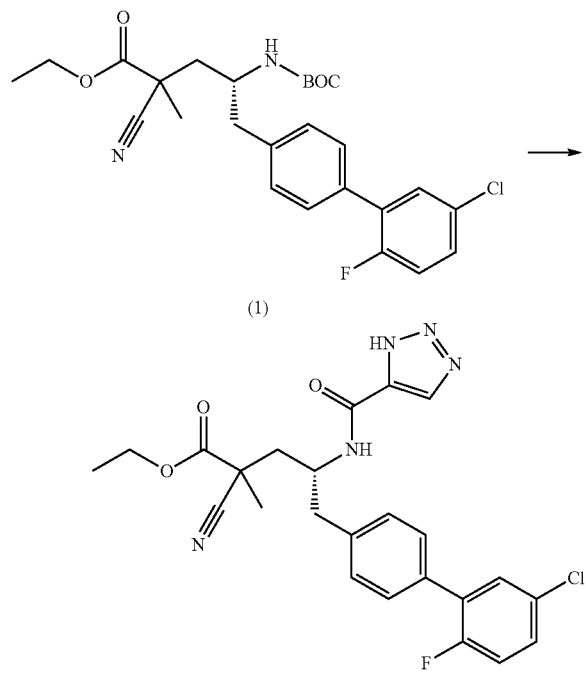

A solution of Compound 1 (18.1 mg, 37 μmol) in HCl (185 μL, 740 μmol) was stirred at room temperature for 30 minutes. After this time, LCMS indicated that the boc group had been cleaved so the solution was concentrated in vacuo. A solution of 3H-[1,2,3]triazole-4-carboxylic acid (5.0 mg, 44 μmol) and HATU (17 mg, 44 μmol) in DMF (370 μL) was stirred at room temperature for 30 minutes. After this time, a solution of the crude amine in DMF (370 μL) was added, followed by DIPEA (19 μL, 111 μmol). The resulting mixture was stirred at room temperature for 1 hour, and then concentrated in vacuo. The crude residue was purified by preparative HPLC to yield 3 products with identical masses (2 of which are diastereomers): isomer a (3.5 mg; purity 97%), isomer b (1.2 mg; purity 100%), and isomer c (1.1 mg; purity 100%). MS m/z [M+H]$^+$ calc'd for $C_{24}H_{23}ClFN_5O_{33}$, 484.15. found 484.2.

Example 14

(R)-5-(5'-Chloro-2'-fluorobiphenyl-4-yl)-2-ethyl-2-hydroxymethyl-4-[(3H-[1,2,3]triazole-4-carbonyl)amino]pentanoic Acid (isomers a and b)

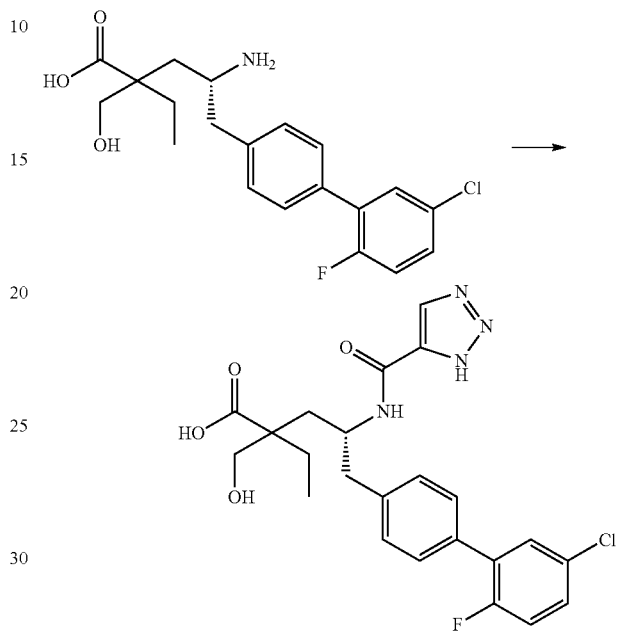

(R)-4-Amino-5-(5'-chloro-2'-fluorobiphenyl-4-yl)-2-ethyl-2-hydroxymethylpentanoic acid (isomer a; 85 mg, 190 μmol, 1.0 eq.) and DIPEA (250 μL, 1.4 mmol, 7.5 eq.) were dissolved in DMF (800 μL). 1H-1,2,3-triazole-4-carboxylic acid (32 mg, 290 μmol, 1.5 eq.), HATU (70 mg, 184 μmol, 1.0 eq.), and DIPEA (100 μL, 572 μmol, 7.5 eq.) were dissolved in DMF (500 μL) and stirred at room temperature for 15 minutes. The solutions were then combined and the resulting mixture stirred at room temperature for 20 minutes and when the reaction was complete (as determined by LC/MS analysis), the mixture was concentrated in vacuo and purified by preparative HPLC to yield the title compound (isomer a; 21.9 mg). LCMS (ESI): calc. $C_{23}H_{24}ClFN_4O_4$=474; obs. M+H=475.1. Retention time: 4.75 min.

(R)-4-Amino-5-(5'-chloro-2'-fluorobiphenyl-4-yl)-2-ethyl-2-hydroxymethylpentanoic acid (isomer b; 85 mg, 190 μmol, 1.0 eq.) and DIPEA (250 μL, 1430 μmol, 7.5 eq.) were dissolved in DMF (800 μL). 1H-1,2,3-triazole-4-carboxylic acid (32 mg, 290 μmol, 1.5 eq.), HATU (70 mg, 184 μmol, 1.0 eq.), and DIPEA (100 μL, 572 μmol, 7.5 eq.) were dissolved in DMF (500 μL) and stirred at room temperature for 15 minutes. The solutions were then combined and the resulting mixture stirred at room temperature for 20 minutes and when the reaction was complete (as determined by LC/MS analysis), the mixture was concentrated in vacuo and purified by preparative HPLC to yield the title compound (isomer b; 37.8 mg). LCMS (ESI): calc. $C_{23}H_{24}ClFN_4O_4$=474; obs. M+H=475.0. Retention time: 4.72 min.

LC/MS Method: flow rate: 1.5 mL/min; Buffer A: 0.1% TFA/H$_2$O; Buffer B 0.1% TFA/MeCN; gradient elution from 5%-100% B over 9.6 min, then 100% B for 1.0 minute, detection at 254 nm.

Example 15

(R)-5-(5'-Chloro-2'-fluorobiphenyl-4-O-2-hydroxymethyl-2-propyl-4-[(3H-[1,2,3]triazole-4-carbonyl)amino]pentanoic Acid (isomers a and b)

LC/MS Method: flow rate: 1.5 mL/min; Buffer A: 0.1% TFA/H$_2$O; Buffer B 0.1% TFA/MeCN; gradient elution from 5%-100% B over 9.6 minutes, then 100% B for 1.0 minute, detection at 254 nm.

Example 16

(R)-5-(5'-Chloro-2'-fluorobiphenyl-4-yl)-2-(2-hydroxyethyl)-2-hydroxymethyl-4-[(3H-[1,2,3]triazole-4-carbonyl)amino]pentanoic Acid (isomers a and b)

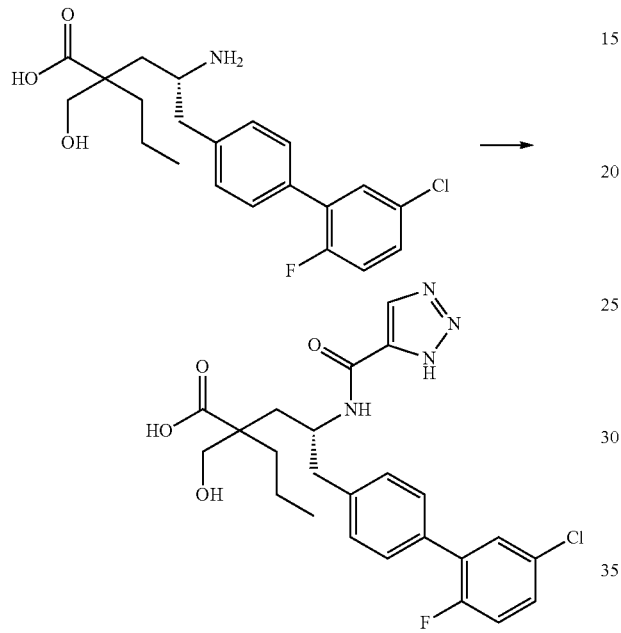

(R)-4-Amino-5-(5'-chloro-2'-fluorobiphenyl-4-yl)-2-hydroxymethyl-2-propylpentanoic acid (isomer a; 40 mg, 90 μmol, 1.0 eq.) and DIPEA (40 μL, 228 μmol, 2.5 eq.) were dissolved in DMF (200 μL). 1H-1,2,3-triazole-4-carboxylic acid (17 mg, 150 μmol, 1.5 eq.), HATU (45 mg, 120 μmol, 1.5 eq.), and DIPEA (40 μL, 228 μmol, 2.5 eq.) were dissolved in DMF (600 μL) and stirred at room temperature for a few minutes. The solutions were then combined and the resulting mixture stirred at room temperature until LC/MS analysis revealed consumption of starting material. The mixture was concentrated in vacuo and purified by preparative HPLC to yield the title compound (isomer a; 15.7 mg). LCMS (ESI): calc. C$_{24}$H$_{26}$ClFN$_4$O$_4$=488; obs. M+H=489.2. Retention time: 5.03 min.

(R)-4-Amino-5-(5'-chloro-2'-fluorobiphenyl-4-yl)-2-hydroxymethyl-2-propylpentanoic acid (isomer b; 60 mg, 140 μmol, 1.0 eq.) and DIPEA (40 μL, 228 μmol, 1.6 eq.) were dissolved in DMF (300 μL). 1H-1,2,3-triazole-4-carboxylic acid (24 mg, 210 μmol, 1.5 eq.), HATU (57 mg, 150 μmol, 1.0 eq.), and DIPEA (80 μL, 456 μmol, 3.2 eq.) were dissolved in DMF (900 μL) and stirred at room temperature for a few minutes. The solutions were then combined and the resulting mixture stirred at room temperature and when the reaction was complete (as determined by LC/MS analysis), the mixture was concentrated in vacuo and purified by preparative HPLC to yield the title compound (isomer b; 33.7 mg). LCMS (ESI): calc. C$_{24}$H$_{26}$ClFN$_4$O$_4$=488; obs. M+H=489.2. Retention time: 4.98 min.

3-[(R)-2-Amino-3-(5'-chloro-2'-fluorobiphenyl-4-yl)-propyl]-3-hydroxymethyl-dihydro-furan-2-one (isomer a; 10 mg, 30 μmol, 1.0 eq.) and DIPEA (30 μL, 170 μmol, 5.6 eq.) were dissolved in DMF (200 μL). 1H-1,2,3-triazole-4-carboxylic acid (10 mg, 90 μmol, 3.0 eq.), DIPEA (60 μL, 340 μmol, 11.2 eq.) and HATU (15 mg, 40 μmol, 1.3 eq.), were dissolved in DMF (600 μL) and stirred at room temperature for a few minutes. The solutions were then combined and the resulting mixture stirred at room temperature and when the reaction was complete (as determined by LC/MS analysis), EtOAc and water were added to the mixture, the organics were then separated and concentrated in vacuo. The crude residue was dissolved in a 1:1 solution of MeOH and aqueous 2N NaOH (4 mL), and stirred at room temperature for 30 minutes and when the reaction was complete (as determined by LC/MS analysis), the mixture was concentrated in vacuo and purified by preparative HPLC to yield the title compound (isomer a; 3 mg). LCMS (ESI): calc. C$_{23}$H$_{24}$ClFN$_4$O$_5$=490; obs. M+H=491.2. Retention time: 2.04 min.

3-[(R)-2-Amino-3-(5'-chloro-2'-fluorobiphenyl-4-yl)-propyl]-3-hydroxymethyl-dihydro-furan-2-one (isomer b; 30 mg, 52 μmol, 1.0 eq.) and DIPEA (50 μL, 291 μmol, 5.6 eq.) were dissolved in DMF (200 μL). 1H-1,2,3-triazole-4-carboxylic acid (17 mg, 156 μmol, 3.0 eq.), DIPEA (100 μL, 582 μmol, 11.2 equiv.) and HATU (25 mg, 68 μmol, 1.3 eq.), were dissolved in DMF (600 μL) and stirred at room temperature for a few minutes. The solutions were then combined and the resulting mixture was stirred at room temperature; when the reaction was complete (as determined by LC/MS analysis), EtOAc and water were added to the mixture. The organic layer was separated, concentrated in vacuo and purified by preparative HPLC to yield the title compound (isomer b; 3.9 mg). LCMS (ESI): calc. $C_{23}H_{24}ClFN_4O_5$=490; obs. M+H=491.2. Retention time: 1.99 min.

LC/MS Method: flow rate: 1.5 mL/min; Buffer A: 0.1% TFA/H$_2$O; Buffer B 0.1% TFA/MeCN; gradient elution from 5-100% B over 3.6 minutes, then 100% B for 1.0 minute, detection at 254 nm.

Example 17

(R)-2-(2-Amino-ethyl)-5-(5'-chloro-2'-fluorobiphenyl-4-yl)-2-hydroxymethyl-4-[(3H-[1,2,3]triazole-4-carbonyl)amino]pentanoic Acid

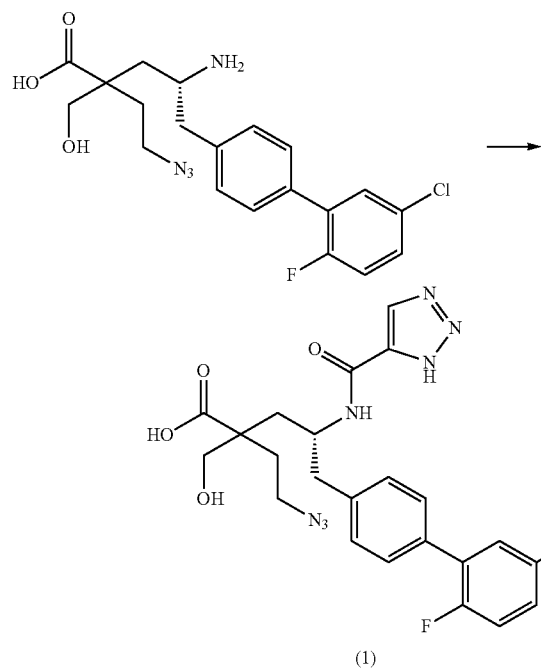

(R)-4-Amino-2-(2-azidoethyl)-5-(5'-chloro-2'-fluorobiphenyl-4-yl)-2-hydroxymethylpentanoic acid (9 mg, 21 µmol, 1.0 eq.) and DIPEA (15 µL, 86 µmol, 4.0 eq.) were dissolved in DMF (0.2 mL). 1H-1,2,3-triazole-4-carboxylic acid (10 mg, 80 µmol, 4 eq.) and DIPEA (30 µL, 172 µmol, 8.1 eq.) were dissolved in DMF (0.5 mL). The solutions were then combined and the resulting mixture stirred at room temperature for 20 minutes; LC/MS analysis revealed a mixture of mono- and bis-acylated products. The mixture was concentrated to an oil and dissolved in a mixture of 2N NaOH (2 mL) and MeOH (1 mL) and stirred for 30 minutes at 60° C.; when the reaction was complete (as determined by LC/MS analysis), the mixture was concentrated in vacuo and acidified to pH 3 with aqueous HCl, and extracted with EtOAc. The organic phase was dried over Na$_2$SO$_4$, filtered, and concentrated in vacuo to yield crude Compound 1 (10 mg). LCMS (ESI): calc. $C_{23}H_{22}ClFN_2O_4$=515; obs. M+H=516.2. Retention time: 4.93 min.

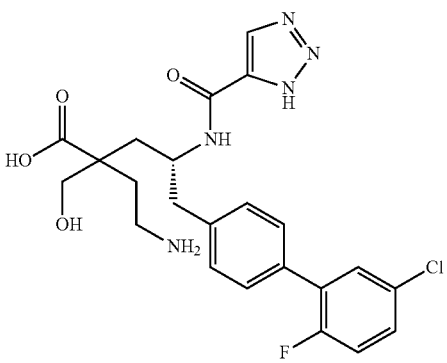

Compound 1 (10 mg) was dissolved in a mixture of EtOAc and isopropanol. Pd/C was added, and the resulting mixture stirred under 1 atmosphere of hydrogen and when the reaction was complete (as determined by LC/MS analysis), the solution was filtered and concentrated, then purified by preparative HPLC to yield the title compound (3.1 mg). LCMS (ESI): calc. $C_{23}H_{25}ClFN_3O_2$=489; obs. M+H=490.3. Retention time: 3.87 min.

LC/MS Method: flow rate: 1.5 mL/min; Buffer A: 0.1% TFA/H$_2$O; Buffer B 0.1% TFA/MeCN; gradient elution from 5%-100% B over 9.6 min, then 100% B for 1.0 minute, detection at 254 nm.

Example 18

(R)-2-(2-Acetylaminoethyl)-5-(5'-chloro-2'-fluorobiphenyl-4-O-2-hydroxymethyl-4-[(3H-[1,2,3]triazole-4-carbonyl)amino]pentanoic Acid

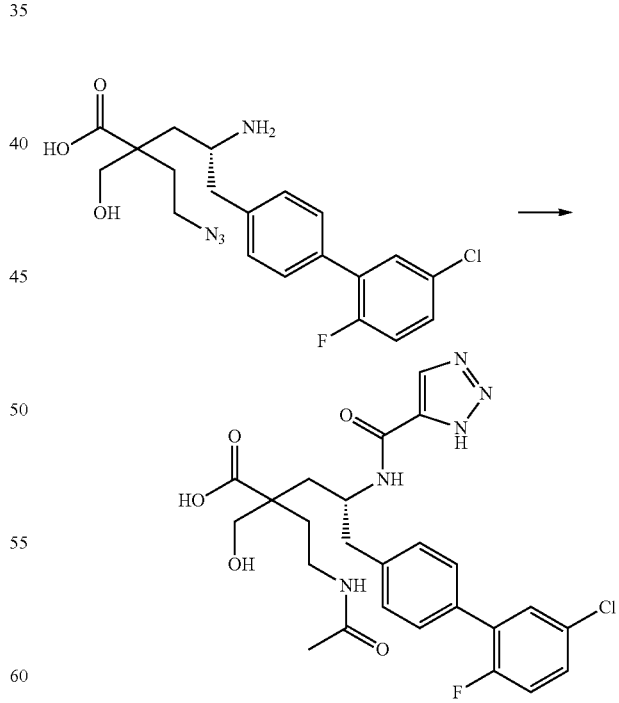

(R)-4-Amino-2-(2-azidoethyl)-5-(5'-chloro-2'-fluorobiphenyl-4-yl)-2-hydroxymethylpentanoic acid (20 mg, 40 µmol, 1.0 eq.) and DIPEA (50 µL, 290 µmol, 7.2 eq.) were dissolved in DMF (200 µL). 1H-1,2,3-triazole-4-carboxylic acid (20 mg, 180 µmol, 4.5 eq.), DIPEA (50 µL, 290 µmol, 7.2 eq.), and HATU (45 mg, 120 μmol, 3.0 eq.) were dissolved in DMF (500 μL) and stirred at room temperature for a few minutes. The solutions were then combined and the resulting mixture stirred at room temperature; when the reaction was complete (as determined by LC/MS analysis), EtOAc and water were added to the mixture; the organics were then separated, concentrated and dissolved in EtOAc (5 mL) and MeOH (1 mL), as well as a few drops of AcOH. Pd/C (10 mg) was added, and the resulting mixture was hydrogenated at 1 atmosphere for two hours and when the reaction was complete (as determined by LC/MS analysis), the mixture was then concentrated and purified by preparative HPLC. The resulting product was treated with acetic anhydride (1.4 μL) in THF (50 μL) and Et$_3$N (50 μL) at 0° C. LC/MS analysis in five minutes showed bis-acylated product. The reaction was quenched with aqueous HCl and stirred overnight at room temperature and when the reaction was complete (as determined by LC/MS analysis), the mixture was purified by preparative HPLC to yield the title compound (1.5 mg). LCMS (ESI): calc. $C_{25}H_{22}ClFN_5O_5$=531; obs. M+H=532.0. Retention time: 2.20 min.

LC/MS Method: flow rate: 1.5 mL/min; Buffer A: 0.1% TFA/H$_2$O; Buffer B 0.1% TFA/MeCN; gradient elution from 5%-100% B over 3.6 minutes, then 100% B for 1.0 minute, detection at 254 nm.

Example 19

2-{(R)-3-(5'-Chloro-2'-fluorobiphenyl-4-yl)-2-[(3H-[1,2,3]triazole-4-carbonyl)amino]propyl}-2-hydroxymethylpent-4-enoic Acid (isomers a and b)

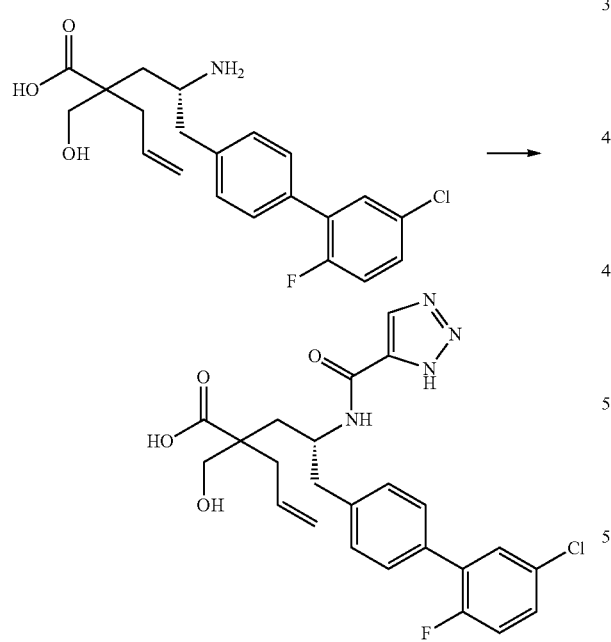

2-[(R)-2-Amino-3-(5'-chloro-2'-fluorobiphenyl-4-yl)propyl]-2-hydroxymethylpent-4-enoic acid (isomer a; 85 mg) was dissolved in DMF. 1H-1,2,3-triazole-4-carboxylic acid (2 eq.), DIPEA (2 eq.) and HATU (1 eq.) were also dissolved in DMF and stirred at room temperature for a few minutes. The solutions were then combined and the resulting mixture stirred at room temperature and when the reaction was complete (as determined by LC/MS analysis), the mixture was concentrated in vacuo and purified by preparative HPLC to yield the title compound (isomer a; 21.9 mg). LCMS (ESI): calc. $C_{24}H_{24}ClFN_4O_4$=486; obs. M+H=487.1. Retention time: 4.87 min.

2-[(R)-2-Amino-3-(5'-chloro-2'-fluorobiphenyl-4-yl)propyl]-2-hydroxymethylpent-4-enoic acid (isomer b; 60 mg) was dissolved in DMF (200 μL). 1H-1,2,3-triazole-4-carboxylic acid (35 mg, 310 μmol, 2.0 eq.), DIPEA (200 μL, 1.2 mmol, 7.6 eq.) and HATU (60 mg, 158 μmol, 1.1 eq.) were also dissolved in DMF (200 μL) and stirred at room temperature for a few minutes. The solutions were then combined and the resulting mixture stirred at room temperature and when the reaction was complete (as determined by LC/MS analysis), the mixture was concentrated in vacuo and purified by preparative HPLC to yield the title compound (isomer b; 24.3 mg). LCMS (ESI): calc. $C_{24}H_{24}ClFN_4O_4$=486; obs. M+H=487.1. Retention time: 4.92 min.

LC/MS Method: flow rate: 1.5 mL/min; Buffer A: 0.1% TFA/H$_2$O; Buffer B 0.1% TFA/MeCN; gradient elution from 5-100% B over 3.6 minutes, then 100% B for 1.0 minute, detection at 254 nm.

Example 20

3-{(R)-3-(5'-Chloro-2'-fluorobiphenyl-4-yl)-2-[(3H-[1,2,3]triazole-4-carbonyl)amino]propyl}tetrahydrofuran-3-carboxylic Acid (isomers a and b)

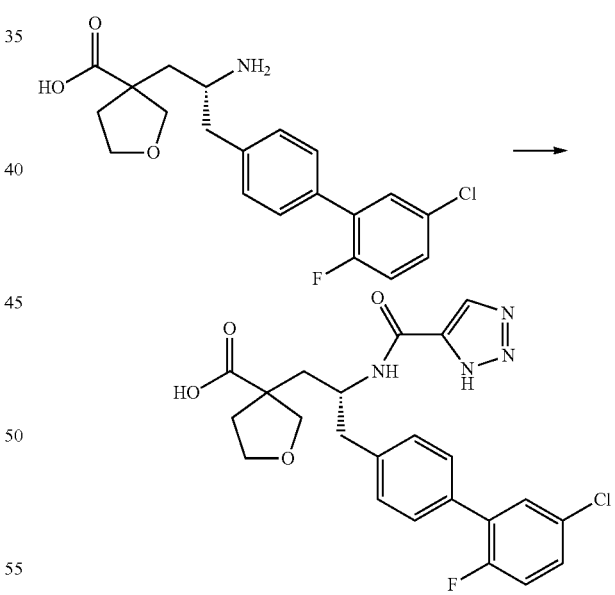

3-[(R)-2-Amino-3-(5'-chloro-2'-fluorobiphenyl-4-yl)propyl]tetrahydrofuran-3-carboxylic acid (isomer a; 10 mg, 24 μmol, 1.0 eq.) and DIPEA (20 μL, 100 μmol, 4.0 eq.) were dissolved in DMF (100 μL). 1H-1,2,3-triazole-4-carboxylic acid (10 mg, 88 μmol, 3.7 eq.), HATU (15 mg, 39 μmol, 1.6 eq.), and DIPEA (40 μL, 200 μmol, 8.0 eq.) were dissolved in DMF (0.5 mL) and stirred at room temperature for ten minutes, then both solutions were combined and stirred at room temperature and when the reaction was complete (as determined by LC/MS analysis), EtOAc and water were added to the mixture; the organics were then separated, concentrated and purified by preparative HPLC to yield the title compound (isomer a; 7.8 mg). LCMS (ESI): calc. $C_{23}H_{22}ClFN_4O_4$=472; obs. M+H=473.0. Retention time: 4.73 min.

3-[(R)-2-Amino-3-(5'-chloro-2'-fluorobiphenyl-4-yl)propyl]tetrahydrofuran-3-carboxylic acid (isomer b; 10 mg, 24 µmol, 1.0 eq.) and DIPEA (20 µL, 100 µmol, 4.0 eq.) were dissolved in DMF (100 µL). 1H-1,2,3-triazole-4-carboxylic acid (10 mg, 88 µmol, 3.7 eq.), HATU (15 mg, 39 µmol, 1.6 eq.), and DIPEA (40 µL, 200 µmol, 8.0 eq.) were dissolved in DMF (0.5 mL) and stirred at room temperature for ten minutes, then both solutions were combined and stirred at room temperature. When the reaction was complete (as determined by LC/MS analysis), EtOAc and water were added to the mixture; the organics were then separated, concentrated and purified by preparative HPLC to yield the title compound (isomer b; 2.9 mg). LCMS (ESI): calc. $C_{23}H_{22}ClFN_4O_4$=472; obs. M+H=472.9. Retention time: 4.77 min.

LC/MS Method: flow rate: 1.5 mL/min; Buffer A: 0.1% TFA/H$_2$O; Buffer B 0.1% TFA/MeCN; gradient elution from 5-100% B over 9.6 min, then 100% B for 1.0 minute, detection at 254 nm.

Example 21

3-{(R)-3-(5'-Chloro-2'-fluorobiphenyl-4-yl)-2-[(3H-[1,2,3]triazole-4-carbonyl)amino]propyl}pyrrolidine-3-carboxylic Acid (isomers a and b)

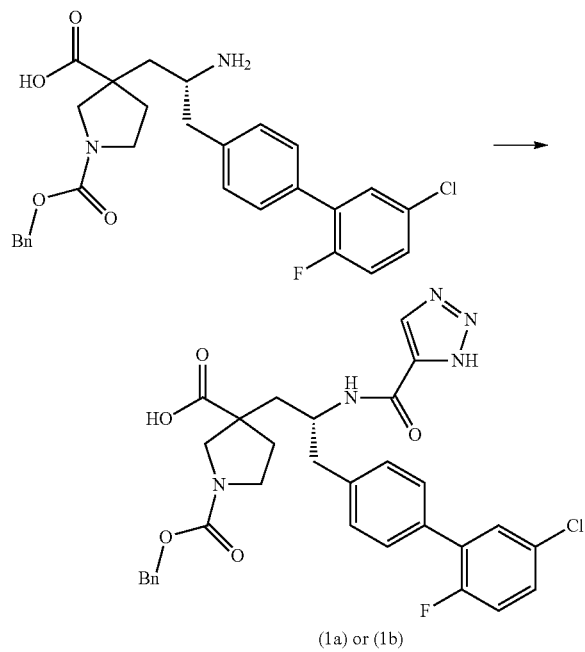

3-[(R)-2-Amino-3-(5'-chloro-2'-fluorobiphenyl-4-yl)-propyl]pyrrolidine-1,3-dicarboxylic acid 1-benzyl ester (isomer a; 14 mg, 35 µmol, 1.0 eq.) was dissolved in DMF. 1H-1,2,3-triazole-4-carboxylic acid (2 eq.), DIPEA (2 eq.), and HATU (1 eq.) were also dissolved in DMF and stirred at room temperature for a few minutes. The solutions were then combined and the resulting mixture stirred at room temperature and when the reaction was complete (as determined by LC/MS analysis), the mixture was concentrated in vacuo to yield crude Compound 1a. LCMS (ESI): calc. $C_{31}H_{29}ClFN_5O_5$=605; obs. M+H=606.1. Retention time: 5.82 min. (LC/MS Method 1)

3-[(R)-2-Amino-3-(5'-chloro-2'-fluorobiphenyl-4-yl)-propyl]pyrrolidine-1,3-dicarboxylic acid 1-benzyl ester (isomer b; 170 mg, 320 µmol, 1.0 eq.) and DIPEA (200 µL, 1150 µmol, 3.6 eq.) were dissolved in DMF (1 mL). 1H-1,2,3-triazole-4-carboxylic acid (100 mg, 880 µmol, 2.8 eq.), DIPEA (200 µL, 1150 µmol, 3.6 eq.) and HATU (200 mg, 530 µmol, 1.6 eq.) were dissolved in DMF (3 mL) and stirred at room temperature for a few minutes. The solutions were then combined and the resulting mixture stirred at room temperature and when the reaction was complete (as determined by LC/MS analysis), the mixture was concentrated in vacuo to yield crude Compound 1b. LCMS (ESI): calc. $C_{31}H_{22}ClFN_5O_4$=605; obs. M+H=606.2. Retention time: 5.73 min. (LC/MS Method 1).

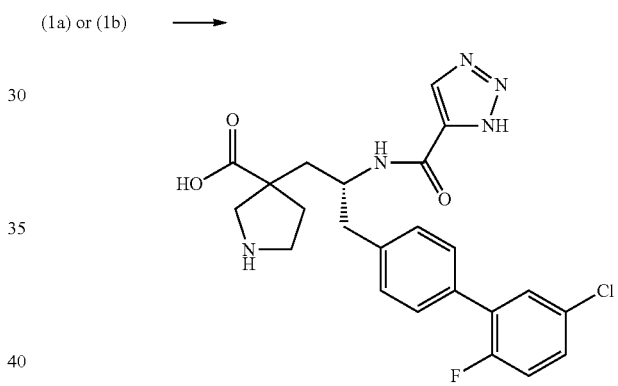

Compound 1a was dissolved in 1:1 6M aqueous HCl/p-dioxane (1 mL) and stirred at 100° C. and when the reaction was complete (as determined by LC/MS analysis), the mixture was concentrated in vacuo and purified by preparative HPLC to yield the title compound (isomer a; 6.9 mg). LCMS (ESI): calc. $C_{23}H_{23}ClFN_5O_3$=471; obs. M+H=472.1. Retention time: 4.14 min. (LC/MS Method 1)

Compound 1b was dissolved in 1:1 6M aqueous HCl/p-dioxane (6 mL) and stirred at 100° C. for one hour and when the reaction was complete (as determined by LC/MS analysis), the mixture was concentrated in vacuo and purified by preparative HPLC to yield the title compound (isomer b; 34 mg). LCMS (ESI): calc. $C_{23}H_{23}ClFN_5O_3$=471; obs. M+H=472.3. Retention time: 2.06 min. (LC/MS Method 2).

LC/MS Method 1: flow rate: 1.5 mL/min; Buffer A: 0.1% TFA/H$_2$O; Buffer B 0.1% TFA/MeCN; gradient elution from 5-100% B over 9.6 min, then 100% B for 1.0 minute, detection at 254 nm.

LC/MS Method 2: flow rate: 1.5 mL/min; Buffer A: 0.1% TFA/H$_2$O; Buffer B 0.1% TFA/MeCN; gradient elution from 5-100% B over 3.6 minutes, then 100% B for 1.0 minute, detection at 254 nm.

Example 22

1-Acetyl-3-{(R)-3-(5'-chloro-2'-fluorobiphenyl-4-yl)-2-[(3H-[1,2,3]triazole-4-carbonyl)amino]propyl}pyrrolidine-3-carboxylic Acid (isomers a and b)

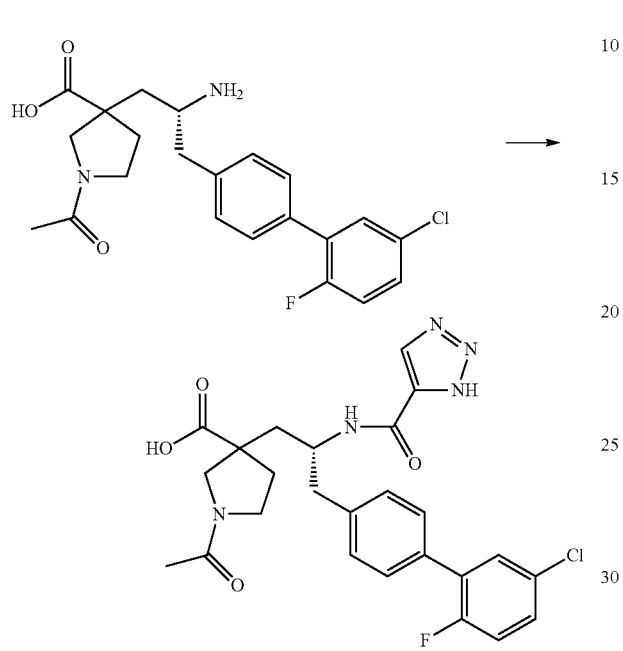

1-Acetyl-3-[(R)-2-amino-3-(5'-chloro-2'-fluorobiphenyl-4-yl)propyl]pyrrolidine-3-carboxylic Acid (isomer a; 10 mg) dissolved in DMF. 1H-1,2,3-triazole-4-carboxylic acid (2 eq.), DIPEA (2 equiv.), and HATU (1 equiv.) were also dissolved in DMF and stirred at room temperature for a few minutes. The solutions were then combined and the resulting mixture stirred at room temperature until the reaction was complete (as seen by LCMS). The mixture was concentrated in vacuo and purified by preparative HPLC to yield the title compound (isomer a; 4.1 mg). LCMS (ESI): calc. $C_{25}H_{25}ClFN_5O_4$=513; obs. M+H=514.3. Retention time: 2.24 min.

1-Acetyl-3-[(R)-2-amino-3-(5'-chloro-2'-fluorobiphenyl-4-yl)propyl]pyrrolidine-3-carboxylic Acid (isomer b; 40 mg, 88 µmol, 1.0 eq.) and DIPEA (50 µL, 170 µmol, 2.0 eq.) were dissolved in DMF (0.2 mL). 1H-1,2,3-triazole-4-carboxylic acid (30 mg, 260 µmol, 3.0 eq.), DIPEA (90 µL, 340 µmol, 4.0 eq.) and HATU (65 mg, 170 µmol, 1.9 eq.), were dissolved in DMF (0.6 mL) and stirred at room temperature for 30 minutes. The solutions were then combined and the resulting mixture stirred at room temperature for ten minutes. The mixture was stirred for 20 minutes with an excess of 2N NaOH in MeOH and concentrated to dryness. It was then acidified to pH 3 with HCl and extracted with EtOAc. The organic phase was concentrated in vacuo and purified by preparative HPLC to yield the title compound (isomer b; 30 mg). LCMS (ESI): calc. $C_{25}H_{25}ClFN_5O_4$=513; obs. M+H=514.3. Retention time: 2.24 min.

LC/MS Method: flow rate: 1.5 mL/min; Buffer A: 0.1% TFA/H$_2$O; Buffer B 0.1% TFA/MeCN; gradient elution from 5-100% B over 3.6 minutes, then 100% B for 1.0 minute, detection at 254 nm.

Example 23

(R)-5-(5'-Chloro-2'-fluorobiphenyl-4-yl)-2-cyano-2-ethyl-4-[(3H-[1,2,3]triazole-4-carbonyl)amino]pentanoic Acid (isomers a and b)

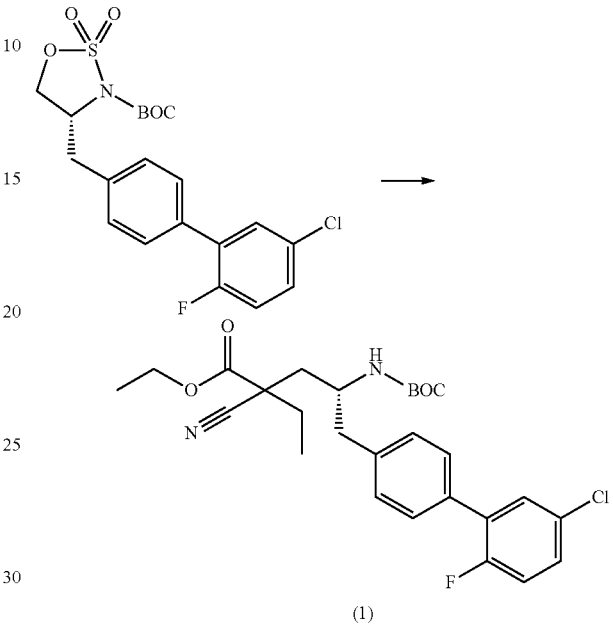

To a solution of ethyl 2-cyanobutanoate (141 µL, 1.0 mmol), (R)-t-butyl 4-((5'-chloro-2'-fluoro-[1,1'-biphenyl]-4-yl)methyl)-1,2,3-oxathiazolidine-3-carboxylate 2,2-dioxide (464 mg, 1.1 mmol) and tetrabutylammonium bromide (32 mg, 100 µmol) in xylene (5.0 mL) was added Cs$_2$CO$_3$ (489 mg, 1.5 mmol). The resulting mixture was stirred at room temperature overnight. 1N HCl (5.0 mL) was added and the solution was stirred at room temperature for 10 minutes. DCM (7.5 mL) was added and the layers were separated and the aqueous layer was extracted with DCM (2×7.5 mL). The combined organic layers were dried over Na$_2$SO$_4$, filtered and concentrated. The crude product was purified by column chromatography (0-30% EtOAc in hexanes over 20 minutes) to yield Compound 1 (20.8 mg) as a clear oil.

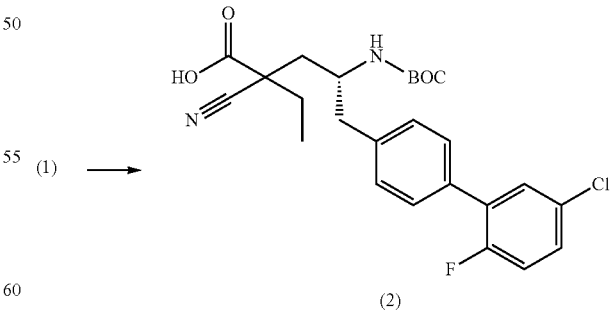

To a solution of Compound 1 ((20.8 mg, 41 µmol) in EtOH (410 µL) was added NaOH (331 µL, 331 µmol). The solution was stirred at room temperature for 2 hours and then concentrated in vacuo to yield Compound 2, which was used without further purification.

(2) →

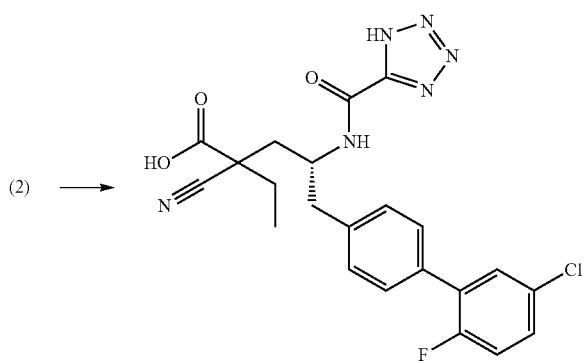 [SMILES: CCC(C#N)(C[C@@H](Cc1ccc(-c2cc(Cl)ccc2F)cc1)NC(=O)c1nnn[nH]1)C(=O)O]

A solution of Compound 2 (19.9 mg, 42 μmol) in HCl (209 μL, 838 μmol) was stirred at room temperature for 1 hour, then concentrated in vacuo. A solution of 3H-[1,2,3]triazole-4-carboxylic acid (5.7 mg, 50 μmol) and HATU (19 mg, 50 μmol) in DMF (420 μL) were stirred at room temperature for 30 minutes. After this time, a solution of the crude amine in DMF (0.2 mL) was added, followed by DIPEA (22 μL, 126 μmol). After stirring at room temperature overnight, the solution was concentrated in vacuo. The crude residue was dissolved in a 50% aqueous AcOH solution (1.5 mL) and purified by preparative HPLC. The 2 diastereomers were separated by preparative HPLC to yield the title compound isomer a (2.3 mg; purity 100%) and isomer b (3.7 mg; purity 100%). MS m/z $[M+H]^+$ calc'd for $C_{23}H_{21}ClFN_5O_3$, 470.13. found 470.2.

Assay 1

In Vitro Assays for the Quantitation of Inhibitor Potencies at Human and Rat NEP, and Human ACE The inhibitory activities of compounds at human and rat neprilysin (EC 3.4.24.11; NEP) and human angiotensin converting enzyme (ACE) were determined using in vitro assays as described below.

Extraction of NEP Activity from Rat Kidneys

Rat NEP was prepared from the kidneys of adult Sprague Dawley rats. Whole kidneys were washed in cold phosphate buffered saline (PBS) and brought up in ice-cold lysis buffer (1% Triton X-114, 150 mM NaCl, 50 mM tris(hydroxymethyl)aminomethane (Tris) pH 7.5; Bordier (1981) *J. Biol. Chem.* 256: 1604-1607) in a ratio of 5 mL of buffer for every gram of kidney. Samples were homogenized on ice using a polytron hand held tissue grinder. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with bovine serum albumin (BSA) as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) and Abz-Phe-Arg-Lys(Dnp)-Pro-OH (Araujo et al. (2000) *Biochemistry* 39:8519-8525; Bachem, Torrance, Calif.) were used in the NEP and ACE assays respectively.

The assays were performed in 384-well white opaque plates at 37° C. using the fluorogenic peptide substrates at a concentration of 10 μM in Assay Buffer (NEP: 50 mM HEPES, pH 7.5, 100 mM NaCl, 0.01% polyethylene glycol sorbitan monolaurate (Tween-20), 10 μM $ZnSO_4$; ACE: 50 mM HEPES, pH 7.5, 100 mM NaCl, 0.01% Tween-20, $ZnSO_4$). The respective enzymes were used at concentrations that resulted in quantitative proteolysis of 1 μM of substrate after 20 minutes at 37° C.

Test compounds were assayed over the range of concentrations from 10 pM to 20 μM. Test compounds were added to the enzymes and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm and 405 nm, respectively Inhibition constants were obtained by nonlinear regression of the data using the equation (GraphPad Software, Inc., San Diego, Calif.):

$$v = v_0/[1+(I/K')]$$

where v is the reaction rate, $v_0$ is the uninhibited reaction rate, I is the inhibitor concentration and K' is the apparent inhibition constant.

Compounds of the invention were tested in this assay and found to have $pK_i$ values at human NEP as follows. In some instances, prodrug compounds did not inhibit the enzyme in this in vitro assay, or the prodrugs (the term "prodrug" is intended to mean an inactive or significantly less active precursor of a drug that is converted into its active form in the body under physiological conditions, for example, by normal metabolic processes; such compounds may not necessarily possess pharmacological activity at NEP, but may be administered orally or parenterally and thereafter metabolized in the body to form compounds that are pharmacologically active at NEP) were not tested (n.d.) since activity would not be expected.

| Ex. | $pK_i$ |
| --- | --- |
| 1a | 8.0-8.4 |
| 1b | 8.0-8.4 |
| 2 | ≥9.0 |
| 3 | 8.5-8.9 |
| 4-1 | 8.0-8.4 |
| 4-2 | 8.5-8.9 |
| 5 | ≥9.0 |
| 6 | ≥9.0 |
| 7 | ≥9.0 |
| 8-1 | ≥9.0 |
| 8-2 | 8.5-8.9 |
| 8-3 | 8.5-8.9 |
| 8-4 | ≥9.0 |
| 8-5 | ≥9.0 |
| 8-6 | ≥9.0 |

-continued

| Ex. | pK$_i$ |
|---|---|
| 8-7 | 8.5-8.9 |
| 8-8 | ≥9.0 |
| 8-9 | 8.5-8.9 |
| 8-10 | 8.5-8.9 |
| 9 | ≥9.0 |
| 10 | 8.5-8.9 |
| 11-1 | 8.5-8.9 |
| 11-2 | ≥9.0 |
| 11-3 | 8.5-8.9 |
| 11-4 | 8.5-8.9 |
| 12a | 7.0-7.4 |
| 12b | ≥9.0 |
| 13a | n.d. |
| 13b | n.d. |
| 13c | n.d. |
| 14a | ≥9.0 |
| 14b | ≥9.0 |
| 15a | ≥9.0 |
| 15b | ≥9.0 |
| 16a | 8.5-8.9 |
| 16b | 7.5-7.9 |
| 17 | 8.5-8.9 |
| 18 | ≥9.0 |
| 19a | ≥9.0 |
| 19b | ≥9.0 |
| 20a | ≥9.0 |
| 20b | ≥9.0 |
| 21a | ≥9.0 |
| 21b | ≥9.0 |
| 22a | ≥9.0 |
| 22b | ≥9.0 |
| 23a | ≥9.0 |
| 23b | 6.5-6.9 |

Assay 2

Pharmacodynamic (PD) assay for ACE and NEP Activity in Anesthetized Rats

Male, Sprague Dawley, normotensive rats are anesthetized with 120 mg/kg (i.p.) of inactin. Once anesthetized, the jugular vein, carotid artery (PE 50 tubing) and bladder (flared PE 50 tubing) catheters are cannulated and a tracheotomy is performed (Teflon Needle, size 14 gauge) to facilitate spontaneous respiration. The animals are then allowed a 60 minute stabilization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of AngI (1.0 µg/kg, for ACE inhibitor activity) at 15 minutes apart. At 15 minutes post-second dose of AngI, the animals are treated with vehicle or test compound. Five minutes later, the animals are additionally treated with a bolus i.v. injection of atrial natriuretic peptide (ANP; 30 µg/kg). Urine collection (into pre-weighted eppendorf tubes) is started immediately after the ANP treatment and continued for 60 minutes. At 30 and 60 minutes into urine collection, the animals are re-challenged with AngI. Blood pressure measurements are done using the Notocord system (Kalamazoo, Mich.). Urine samples are frozen at −20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition is assessed by quantifying the % inhibition of pressor response to AngI. NEP inhibition is assessed by quantifying the potentiation of ANP-induced elevation in urinary cGMP output.

Assay 3

In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site with free access to food and water. For blood pressure recording, these animals are surgically implanted with small rodent radiotransmitters (telemetry unit; DSI Models TA11PA-C40 or C50-PXT, Data Science Inc., USA). The tip of the catheter connected to the transmitter is inserted into the descending aorta above the iliac bifurcation and secured in place with tissue adhesive. The transmitter is kept intraperitoneally and secured to the abdominal wall while closing of the abdominal incision with a non-absorbable suture. The outer skin is closed with suture and staples. The animals are allowed to recover with appropriate post-operative care. On the day of the experiment, the animals in their cages are placed on top of the telemetry receiver units to acclimate to the testing environment and baseline recording. After at least of 2 hours baseline measurement is taken, the animals are then dosed with vehicle or test compound and followed out to 24 hours post-dose blood pressure measurement. Data is recorded continuously for the duration of the study using Notocord software (Kalamazoo, Mich.) and stored as electronic digital signals. Parameters measured are blood pressure (systolic, diastolic and mean arterial pressure) and heart rate.

Assay 4

In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet. One week after the start of the high salt diet (8% in food or 1% NaCl in drinking water), a deoxycorticosterone acetate (DOCA) pellet (100 mg, 90 days release time, Innovative Research of America, Sarasota, Fla.) is implanted subcutaneously and unilateral nephrectomy is performed. At this time, the animals are also surgically implanted with small rodent radiotransmitters for blood pressure measurement (see Assay 3 for details). The animals are allowed to recover with appropriate post-operative care. Study design, data recording, and parameters measured is similar to that described for Assay 3.

Assay 5

In Vivo Evaluation of Antihypertensive Effects in the Conscious Dahl/SS Rat Model of Hypertension Male, Dahl salt sensitive rats (Dahl/SS, 6-7 weeks of age from Charles River Laboratory, USA) are allowed at least 48 hours of acclimation upon arrival at the testing site before they were placed on a 8% NaCl high salt diet (TD.92012, Harlan, USA) then surgically implanted with small rodent radiotransmitters for blood pressure measurement (see Assay 3 for details). The animals are allowed to recover with appropriate post-operative care. At approximately 4 to 5 weeks from the start of high salt diet, these animals are expected to become hypertensive. Once the hypertension level is confirmed, these animals are used for the study while continued with the high salt diet to maintain their hypertension level. Study design, data recording, and parameters measured is similar to that described in Assay 3.

Assay 6

Rat PO Cassette Assay

Oral bioavailability, or % F, is a measure of the percentage of a drug in an oral dose that actually reaches the systemic circulation. Compound losses can occur due to incomplete formulation dissolution, incomplete absorption due to compound insolubility or instability along the GI, or metabolism in the gut or across the gut wall. The fraction of the dose which reaches the hepatic portal vein must also then pass through the liver before reaching the systemic circulation. Compound metabolism, or "first-pass extraction," can occur during this initial passage through the liver, and this is an additional potential source of compound loss. Oral bioavailability is calculated as the dose-normalized ratio of drug exposure after an oral dose to that after an intravenous dose, wherein the entire dose is delivered directly to the systemic circulation.

Each cassette study begins with 10 mM DMSO stock solutions of up to 5 different compounds. Typically, compounds are selected such no two compounds dosed in the same cassette have a molecular weight within 5 Da of each other. This simplifies subsequent bioanalysis. Appropriate volumes of each DMSO stock are added into a volume of vehicle (5% sodium bicarbonate, 5% dextrose in $H_2O$) such that the final concentration of each compound is 0.25 mg/mL. Intravenous dosing solutions are sterile-filtered (0.2 µm) prior to dosing.

Pre-cannulated male Sprague-Dawley rats (3 per cassette per route) between 8 and 10 weeks of age were obtained from Harlan Laboratories (Indianapolis, Ind.). Rats received either a single oral gavage or a single intravenous (via lateral tail vein) dose (2 mL/kg) of the dosing solution. The final dose was 0.5 mg/kg. Serial blood samples were harvested via jugular vein cannula at 3 minutes, 15 minutes, 30 minutes, 1 hours, 2 hours, 4 hours, 6 hours, and 24 hours post-dose. Sampling was performed either manually or using automated blood samplers. Samples were collected into microtainer tubes containing EDTA as the anticoagulant and are processed to plasma by refrigerated centrifugation.

Plasma samples were extracted with 3 volumes of MeCN containing a suitable internal standard. Extracts were reconstituted into 3 volumes of water containing 1% formic acid, and analyzed via HPLC-coupled MS/MS. Plasma concentration-time data were analyzed using the Phoenix software (Pharsight Corp., St. Louis, Mo.) to calculate pharmacokinetic parameters.

Compounds of the invention of particular interest were those having a % F>10%, when tested in this assay. These include the following compounds:

| Ex. |
|---|
| 9 |
| 11-4 |
| 14a |
| 14b |

-continued

| Ex. |
|---|
| 15a |
| 15b |
| 20a |
| 20b |

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:
1. A compound of formula I:

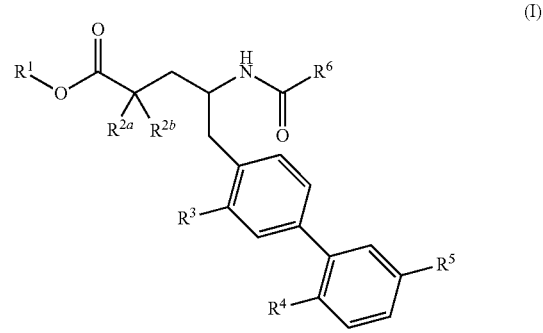

where:
$R^1$ is H, —$C_{1-8}$alkyl, —CH(CH$_3$)OC(O)—O-cyclohexyl, —(CH$_2$)$_2$-morpholinyl, or —CH$_2$-5-methyl-[1,3]dioxol-2-one;
$R^{2a}$ is —$C_{1-2}$alkyl and $R^{2b}$ is —$C_{0-2}$alkylene-NH$_2$, —C(O)NH$_2$, —COOH, —CH$_2$—O—$C_{1-6}$alkyl, —CN, or pyridine; or $R^{2a}$ is —CH$_2$OH and $R^{2b}$ is —CH$_2$CH$_3$, —(CH$_2$)$_2$CH$_3$, —$C_{1-2}$alkylene-OH, —(CH$_2$)$_2$NH$_2$, —(CH$_2$)$_2$—NHC(O)CH$_3$, or —CH$_2$CH=CH$_2$; or $R^{2a}$ and $R^{2b}$ are taken together to form —O—(CH$_2$)$_2$—, —(CH$_2$)$_2$—O—CH$_2$—, —CH$_2$—NH—CH$_2$—, —NH—(CH$_2$)$_2$—, —(CH$_2$)—NH—(CH$_2$)$_2$—, or —(CH$_2$)—N[C(O)CH$_3$]—(CH$_2$)$_2$—;
$R^3$, $R^4$ and $R^5$ are independently H or halo;
$R^6$ is a heterocycle selected from the group consisting of 3H-oxazol-2-one, [1,2,4]oxadiazol-5-one, [1,2,3,5]oxatriazole, [1,2,4]triazolo[1,5-α]pyridine, triazole, pyrazole, imidazole, oxazole, isoxazole, isothiazole, pyridine, oxadiazole, and pyrimidine; the heterocycle is attached at a carbon atom; and each nitrogen atom in the heterocycle is unsubstituted or substituted with an $R^{60}$ group selected from the group consisting of —OH, —(CH$_2$)$_2$OH, —$C_{0-2}$alkylene-O—$C_{1-6}$alkyl, —$C_{1-6}$alkyl, —CHF$_2$, and —CF$_3$; and each carbon atom in the heterocycle is unsubstituted or substituted with an $R^{61}$ group independently selected from the group consisting of halo, —OH, —$C_{1-6}$alkyl, —$C_{0-2}$alkylene-O—C$_{1-6}$alkyl, —C(O)CH$_3$, —C(O)NH(CH$_3$), —C(O)N(CH$_3$)$_2$, —C$_{3-6}$cycloalkyl, —CF$_3$, —CH$_2$SO$_2$CH$_3$, —NH$_2$, —CH$_2$NH$_2$, —CH$_2$N(CH$_3$)$_2$, and phenyl substituted with methyl or halo; with the proviso that when R$^{2a}$ is —CH$_3$ and R$^{2b}$ is —CH$_2$—O—C$_{1-6}$alkyl, then R$^6$ is not unsubstituted 3H-oxazol-2-one; unsubstituted [1,2,3]triazole; [1,2,3]triazole substituted with an R$^{60}$ group selected from the group consisting of —OH, —C$_{0-2}$alkylene-O—C$_{1-6}$alkyl, and —C$_{1-6}$alkyl; [1,2,4]triazole substituted with an R$^{61}$ group selected from the group consisting of halo and —OH; pyrazole substituted with an R$^{60}$ group that is —C$_{1-6}$alkyl; pyrazole substituted with an R$^{61}$ group selected from the group consisting of —OH, —C$_{1-6}$alkyl, —C$_{0-2}$alkylene-O—C$_{1-6}$alkyl, and —C(O)CH$_3$; or isoxazole substituted with an R$^{61}$ group selected from the group consisting of —OH, —C$_{1-6}$alkyl, and —C$_{0-2}$alkylene-O—C$_{1-6}$alkyl;

or a pharmaceutically acceptable salt thereof.

2. The compound of claim 1, where R$^1$ is H, —CH$_2$CH$_3$, —CH(CH$_3$)$_2$, —(CH$_2$)$_3$CH$_3$, or —(CH$_2$)$_5$CH$_3$.

3. The compound of claim 2, where R$^1$ is H or —CH$_2$CH$_3$.

4. The compound of claim 1, where R$^{2a}$ is —C$_{1-2}$alkyl and R$^{2b}$ is —NH$_2$, —CH$_2$NH$_2$, —C(O)NH$_2$, —COOH, —CH$_2$—O—CH$_3$, —CH$_2$—O—CH$_2$CH$_3$, or —CN; or R$^{2a}$ is —CH$_2$OH and R$^{2b}$ is —CH$_2$CH$_3$, —(CH$_2$)$_2$CH$_3$, —(CH$_2$)$_2$—OH, —(CH$_2$)$_2$NH$_2$, —(CH$_2$)$_2$—NHC(O)CH$_3$, or —CH$_2$CH=CH$_2$; or R$^{2a}$ and R$^{2b}$ are taken together to form —O—(CH$_2$)$_2$—, —(CH$_2$)$_2$—O—CH$_2$—, —CH$_2$—NH—CH$_2$—, —NH—(CH$_2$)$_2$—, —(CH$_2$)—NH—(CH$_2$)$_2$—, or —(CH$_2$)—N[C(O)CH$_3$]—(CH$_2$)$_2$—.

5. The compound of claim 4, where R$^{2a}$ is —CH$_3$ and R$^{2b}$ is —NH$_2$, —CH$_2$NH$_2$, —C(O)NH$_2$, —COOH, —CH$_2$—O—CH$_3$, —CH$_2$—O—CH$_2$CH$_3$, or —CN; or R$^{2a}$ is —CH$_2$CH$_3$ and R$^{2b}$ is —CN; or R$^{2a}$ is —CH$_2$OH and R$^{2b}$ is —CH$_2$CH$_3$, —(CH$_2$)$_2$CH$_3$, —(CH$_2$)$_2$—OH, —(CH$_2$)$_2$NH$_2$, —(CH$_2$)$_2$—NHC(O)CH$_3$, or —CH$_2$CH=CH$_2$; or R$^{2a}$ and R$^{2b}$ are taken together to form —(CH$_2$)$_2$—O—CH$_2$—, —(CH$_2$)—NH—(CH$_2$)$_2$—, or —(CH$_2$)—N[C(O)CH$_3$]—(CH$_2$)$_2$—.

6. The compound of claim 1, where R$^3$ is H.

7. The compound of claim 1, where R$^4$ is F.

8. The compound of claim 1, where R$^5$ is Cl.

9. The compound of claim 1, where R$^3$ is H, R$^4$ is F, and R$^5$ is Cl; or R$^3$ and R$^4$ are H and R$^5$ is Br or Cl; or R$^3$, R$^4$, and R$^5$ are H; or R$^3$ is Cl, R$^4$ is F, and R$^5$ is Cl; or R$^3$ is H, R$^4$ is F, and R$^5$ is H.

10. The compound of claim 9, where R$^3$ is H, R$^4$ is F, and R$^5$ is Cl; or R$^3$ and R$^4$ are H and R$^5$ is Cl.

11. The compound of claim 1, where R$^6$ is 3H-oxazol-2-one, 4H-[1,2,4]oxadiazol-5-one, [1,2,3,5]oxatriazole, [1,2,4]triazolo[1,5-α]pyridine, [1,2,3]triazole, [1,2,4]triazole, pyrazole, imidazole, oxazole, isoxazole, isothiazole, pyridine, oxadiazole, or pyrimidine.

12. The compound of claim 11, where R$^6$ is 4H-[1,2,4]oxadiazol-5-one, [1,2,3]triazole, [1,2,4]triazole, pyrazole, oxazole, pyridine, or pyrimidine.

13. The compound of claim 1, where the nitrogen atoms in the heterocycle are unsubstituted.

14. The compound of claim 1, where R$^{60}$ is —OH, —(CH$_2$)$_2$OH, —OCH$_3$, —OCH$_2$CH$_3$, —CH$_3$, —CHF$_2$, or —CF$_3$.

15. The compound of claim 14, where R$^{60}$ is —(CH$_2$)$_2$OH, —OCH$_3$, —OCH$_2$CH$_3$, or —CHF$_2$.

16. The compound of claim 1, where the carbon atoms in the heterocycle are unsubstituted.

17. The compound of claim 1, where R$^{61}$ is chloro, —OH, —CH$_3$, —CH$_2$CH$_3$, —(CH$_2$)$_2$CH$_3$, —CH(CH$_3$)$_2$, —OCH$_3$, —OCH$_2$CH$_3$, —CH$_2$—OCH$_3$, —C(O)CH$_3$, —C(O)NH(CH$_3$), —C(O)N(CH$_3$)$_2$, cyclopropyl, —CF$_3$, —CH$_2$SO$_2$CH$_3$, —NH$_2$, —CH$_2$NH$_2$, —CH$_2$N(CH$_3$)$_2$, or phenyl substituted with methyl or halo.

18. The compound of claim 17, where R$^{61}$ is chloro, —CH$_3$, —C(O)CH$_3$, cyclopropyl, or —CF$_3$.

19. The compound of claim 1, where a first carbon atom in the heterocycle is substituted with an R$^{61}$ group selected from the group consisting of fluoro, —OH, —CH$_3$, —C$_{0-2}$alkylene-O—C$_{1-6}$alkyl, —C(O)CH$_3$, —C$_{3-6}$cycloalkyl, —CF$_3$, —CH$_2$SO$_2$CH$_3$, —NH$_2$, and —CH$_2$N(CH$_3$)$_2$; and a second carbon atom in the heterocycle is substituted with an R$^{61}$ group selected from the group consisting of halo, —OH, —C$_{1-6}$alkyl, —O—CH$_2$CH$_3$, —C(O)CH$_3$, cyclopropyl, —CF$_3$, —CH$_2$SO$_2$CH$_3$, —NH$_2$, and —CH$_2$N(CH$_3$)$_2$.

20. A process for preparing the compound of claim 1, comprising the step of coupling a compound of formula 1 with a compound of formula 2:

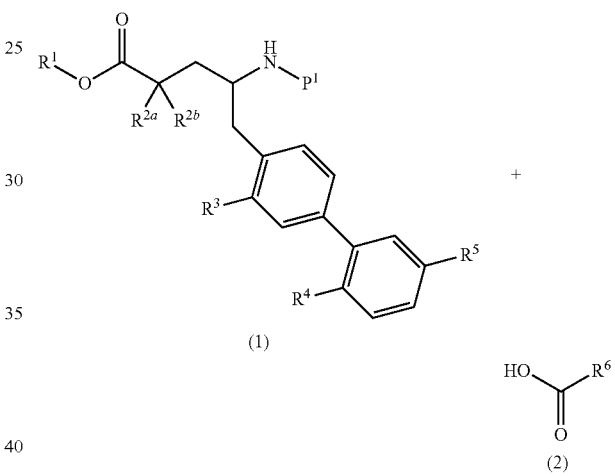

to produce a compound of formula I; where P$^1$ is H or an amino-protecting group selected from t-butoxycarbonyl, trityl, benzyloxycarbonyl, 9-fluorenylmethoxycarbonyl, formyl, trimethylsilyl, and t-butyldimethylsilyl; and where the process further comprises deprotecting the compound of formula 1 when P$^1$ is an amino protecting group.

21. A compound of formula 5:

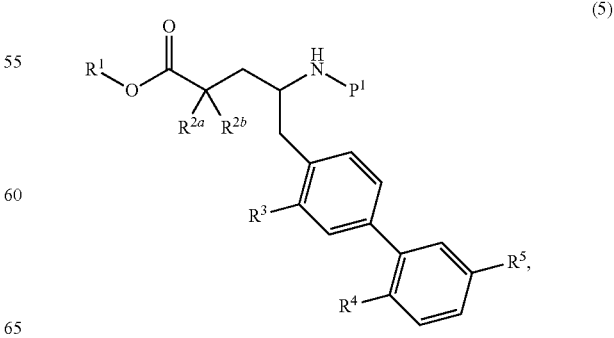

where:
- $R^1$ is H, —$C_{1-8}$alkyl, —CH(CH$_3$)OC(O)—O-cyclohexyl, —(CH$_2$)$_2$-morpholinyl, or —CH$_2$-5-methyl-[1,3]dioxol-2-one;
- $R^{2a}$ is —$C_{1-2}$alkyl and $R^{2b}$ is —$C_{0-2}$alkylene-NH$_2$, —C(O)NH$_2$, —COOH, —CN, or pyridine; or $R^{2a}$ is —CH$_2$OH and $R^{2b}$ is —CH$_2$CH$_3$, —(CH$_2$)$_2$CH$_3$, —$C_{1-2}$alkylene-OH, —(CH$_2$)$_2$NH$_2$, —(CH$_2$)$_2$—NHC(O)CH$_3$, or —CH$_2$CH=CH$_2$; or $R^{2a}$ and $R^{2b}$ are taken together to form —O—(CH$_2$)$_2$—, —(CH$_2$)$_2$—O—CH$_2$—, —CH$_2$—NH—CH$_2$—, —NH—(CH$_2$)$_2$—, —(CH$_2$)—NH—(CH$_2$)$_2$—, or —(CH$_2$)—N[C(O)CH$_3$]—(CH$_2$)$_2$—;
- $P^1$ is H or an amino-protecting group selected from the group consisting of t-butoxycarbonyl, trityl, benzyloxycarbonyl, 9-fluorenylmethoxycarbonyl, formyl, trimethylsilyl, and t-butyldimethylsilyl; or a salt thereof.

22. A pharmaceutical composition comprising a pharmaceutically acceptable carrier and the compound of claim 1.

23. The pharmaceutical composition of claim 22, further comprising a therapeutic agent selected from the group consisting of adenosine receptor antagonists, α-adrenergic receptor antagonists, β$_1$-adrenergic receptor antagonists, β$_2$-adrenergic receptor agonists, dual-acting β-adrenergic receptor antagonist/α$_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, antidiabetic agents, antidiarrheal agents, anti-glaucoma agents, anti-lipid agents, antinociceptive agents, anti-thrombotic agents, AT$_1$ receptor antagonists and dual-acting AT$_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof.

24. The pharmaceutical composition of claim 23, wherein the therapeutic agent is an AT$_1$ receptor antagonist.

* * * * *